(12) United States Patent
Duggan et al.

(10) Patent No.: US 6,410,526 B1
(45) Date of Patent: Jun. 25, 2002

(54) αV INTEGRIN RECEPTOR ANTAGONISTS

(75) Inventors: Mark E. Duggan, Schwenksville; George D. Hartman, Lansdale; Robert S. Meissner, Schwenksville; James J. Perkins, Churchville, all of PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/583,522

(22) Filed: May 31, 2000

Related U.S. Application Data

(60) Provisional application No. 60/137,101, filed on Jun. 2, 1999, and provisional application No. 60/179,216, filed on Jan. 31, 2000.

(51) Int. Cl.$^7$ ................ A61K 31/55; C07D 487/02; A61P 19/10
(52) U.S. Cl. ............... 514/212.02; 514/212.06; 514/215; 540/521; 540/543; 540/577; 540/580
(58) Field of Search ............... 514/212.02, 212.06, 514/215; 540/521, 543, 577, 580

(56) References Cited

U.S. PATENT DOCUMENTS

| | | | |
|---|---|---|---|
| 3,843,798 A | 10/1974 | Cook et al. | 424/319 |
| 5,025,025 A | 6/1991 | Bhagwat et al. | 514/340 |
| 5,352,667 A | 10/1994 | Lider et al. | 514/19 |
| 5,455,243 A | 10/1995 | Duggan et al. | 514/218 |
| 5,668,159 A | 9/1997 | Jin et al. | 514/363 |
| 6,017,926 A | 1/2000 | Askew et al. | 514/300 |
| 6,048,861 A | 4/2000 | Askew et al. | 514/256 |

FOREIGN PATENT DOCUMENTS

| | | |
|---|---|---|
| EP | 0 796 855 A1 | 9/1997 |
| WO | WO 94/08577 | 4/1994 |
| WO | WO 95/32710 | 12/1995 |
| WO | WO 97/26250 | 7/1997 |
| WO | WO 97/37655 | 10/1997 |
| WO | WO 98/08840 | 3/1998 |
| WO | WO 98/18460 | 5/1998 |
| WO | WO 98/18461 | 5/1998 |
| WO | WO 98/31359 | 7/1998 |
| WO | WO 99/30709 | 6/1999 |
| WO | WO 99/30713 | 6/1999 |
| WO | WO 99/31061 | 6/1999 |
| WO | WO 99/31099 | 6/1999 |

OTHER PUBLICATIONS

Miller et al., Discovery of Orally Active Nonpeptide Vitronectin Receptor Antagonists Based on a 2–Benzazepine Gly–Asp Mimetic, Journal of Medicinal Chemistry, vol. 43, No. 1, pp. 22–26, 2000.*

Kerr, J. S., et al., "Small Molecule alphaV Integrin Antagonists: Novel Anticancer Agents," *Exp. Opin. Invest. Drugs*, vol. 9 (6), pp. 1271–1279 (2000).

* cited by examiner

*Primary Examiner*—Brenda Coleman
(74) *Attorney, Agent, or Firm*—Philippe L. Durette; Melvin Winokur

(57) ABSTRACT

The present invention relates to novel nonanoic acid derivatives, their synthesis, and their use as αv integrin receptor antagonists. More particularly, the compounds of the present invention are antagonists of the integrin receptors αvβ3 and αvβ5 and are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, cancer, and metastatic tumor growth.

28 Claims, No Drawings

αV INTEGRIN RECEPTOR ANTAGONISTS

CROSS-REFERENCE TO RELATED APPLICATIONS

The present invention is related to U.S. provisional applications Serial No. 60/137,101, filed Jun. 2, 1999, and 60/179,216, filed Jan. 31, 2000; the contents of both of which are hereby incorporated by reference.

FIELD OF THE INVENTION

The present invention relates to nonanoic acid derivatives, their synthesis, and their use as αv integrin receptor antagonists. More particularly, the compounds of the present invention are antagonists of the integrin receptors αvβ3, αvβ5, and αv integrin receptors associated with other β-subunits, and are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, cancer, and metastatic tumor growth.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts," *Journal of Endocrinology*, 154: S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin on osteoclasts, e.g., on rat, chicken, mouse and human osteoclasts, is an integrin receptor known as αvβ3, which is thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration, and angiogenesis (i.e. formation of new blood vessels), and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, αvβ3 antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Evidence has also been presented suggesting that angiogenesis is a central factor in the initiation and persistence of arthritic disease, and that the vascular integrin αvβ3 may be a preferred target in inflammatory arthritis. Therefore, αvβ3 antagonists which inhibit angiogenesis may represent a novel therapeutic approach to the treatment of arthritic disease, such as rheumatoid arthritis (see C. M. Storgard, et al., "Decreased angiogenesis and arthritic disease in rabbits treated with an αvβ3 antagonist," *J. Clin. Invest.*, 103: 47–54 (1999), which is incorporated by reference herein in its entirety).

Moreover, compounds of this invention can also inhibit neovascularization by acting as antagonists of the integrin receptor, αvβ5. A monoclonal antibody for αvβ5 has been shown to inhibit VEGF-induced angiogenesis in rabbit cornea and the chick chorioallantoic membrane model (See M. C. Friedlander, et.al., *Science* 270: 1500–1502 (1995), which is incorporated by reference herein in its entirety). Thus, compounds that antagonize αvβ5 are useful for treating and preventing macular degeneration, diabetic retinopathy, viral disease, cancer, and metastatic tumor growth.

Additionally, compounds of the instant invention can inhibit angiogenesis and inflammation by acting as antagonists of αv integrin receptors associated with other β subunits, suh as αvβ6 and αvβ8. (see, for example, Melpo Christofidou-Solomidou, et al., "Expression and Function of Endothelial Cell αv Integrin Receptors in Wound-Induced Human Angiogenesis in Human Skin/SCID Mice Chimeras," *American Journal of Pathology*, 151: 975–83 (1997) and Xiao-Zhu Huang, et al., "Inactivation of the Integrin β6 Subunit Gene Reveals a Role of Epithelial Integrins in Regulating Inflammation in the Lungs and Skin, *Journal of Cell Biology*," 133: 921–28 (1996), which are incorporated by reference herein in their entirety).

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammation, cancer, and metastatic tumor growth.

Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 99/31061; WO 00/06169; EP 853084; EP 854140; EP 854145; U.S. Pat. No. 5,780,426; and U.S. Pat. No. 6,048,861. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption in Vitro and Prevents Osteoporosis in Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," *Bone* 23: S219 (1998)).

The αvβ3 integrin receptor recognizes the Arg-Gly-Asp (RGD) tripeptide sequence in its cognate matrix and cell surface glycoproteins (see J. Samanen, et al., "Vascular Indications for Integrin αv Antagonists," *Curr. Pharmaceut. Design* 3: 545–584 (1997)). A benzazepine nucleus has been employed among others by Genentech and SmithKline Beecham as a conformationally constrained Gly-Asp mimetic to elaborate nonpeptide αvβ3 integrin receptor antagonists substituted at the N-terminus with heterocyclic arginine mimetics (see R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Patents assigned to SmithKline Beecham that disclose such benzazepine, as well as related benzodiazepine and benzocycloheptene, αvβ3 integrin receptor antagonists include WO 96/00574, WO 96/00730, WO 96/06087, WO 96/26190, WO 97/24119, WO 97/24122, WO 97/24124, WO 98/15278, WO 99/05107, WO 99/06049, WO 99/15170, and WO 99/15178, and to Genentech include WO 97/34865. The dibenzocycloheptene, as well as dibenzoxazepine, nucleus has also been employed as a Gly-Asp mimetic to afford αvβ3 antagonists (see WO 97/01540, WO 98/30542, WO 99/11626, and WO 99/15508 all assigned to SmithKline Beecham).

Other integrin receptor antagonists featuring backbone conformational ring constraints have been described in WO 98/08840; WO 99/30709; WO 99/30713; WO 99/31099; WO 00/09503; U.S. Pat. No. 5,919,792; U.S. Pat. No. 5,925,655; U.S. Pat. No. 5,981,546; and U.S. Pat. No. 6,017,926.

However, there still remains a need for small-molecule, non-peptidic selective αv integrin receptor antagonists that display improved potency, pharmacodynamic, and pharmacokinetic properties, such as oral bioavailability and duration of action, over already described compounds. Such compounds would prove to be useful for the treatment, prevention, or suppression of various pathologies enumerated above that are mediated by αv integrin receptor binding and cell adhesion and activation.

In U.S. Pat. No. 6,048,861 (Apr. 11, 2000), we disclosed, inter alia, a series of 3-substituted nonanoic acid derivatives which are potent αvβ3 integrin receptor antagonists. In the present invention, we describe analogous alkanoic acid derivatives which are substituted at the C-5 or C-7 position of the aliphatic chain with an oxygen functionality, such as hydroxy and keto, and at C-3 with an optionally substituted aryl group. When compared to the parent compounds, the chain-oxygenated compounds of the instant invention are less hydrophobic, show decreased binding to plasma proteins, and exhibit superior in vivo pharmacokinetic and/or pharmacodynamic properties.

It is therefore an object of the present invention to provide novel nonanoic acid derivatives oxygenated at the C-5 or C-7 position of the aliphatic chain which are useful as αv integrin receptor antagonists.

It is another object of the present invention to provide novel nonanoic acid derivatives oxygenated at the C-5 or C-7 position of the aliphatic chain which are useful as αvβ3 receptor antagonists.

It is another object of the present invention to provide novel nonanoic acid derivatives oxygenated at the C-5 or C-7 position of the aliphatic chain which are useful as αvβ5 receptor antagonists.

It is another object of the present invention to provide novel nonanoic acid derivatives oxygenated at the C-5 or C-7 position of the aliphatic chain which are useful as dual αvβ3/αvβ5 receptor antagonists.

It is another object of the present invention to provide pharmaceutical compositions comprising integrin receptor antagonists.

It is another object of the present invention to provide methods for making the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammation, inflammatory arthritis, viral disease, diabetic retinopathy, macular degeneration, angiogenesis, cancer, and metastatic tumor growth.

It is another object of the present invention to provide compounds and pharmaceutical compositions useful for treating osteoporosis.

It is another object of the present invention to provide methods for inhibiting bone resorption, restenosis, atherosclerosis, inflammation, inflammatory arthritis, viral disease, diabetic retinopathy, macular degeneration, angiogenesis, cancer, and metastatic tumor growth.

It is another object of the present invention to provide methods for treating osteoporosis.

These and other objects will become readily apparent from the detailed description which follows.

SUMMARY OF THE INVENTION

The present invention relates to novel compounds represented by structural formula (I):

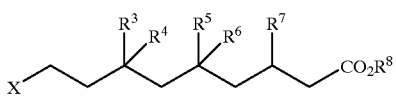

(I)

wherein:

X is selected from the group consisting of

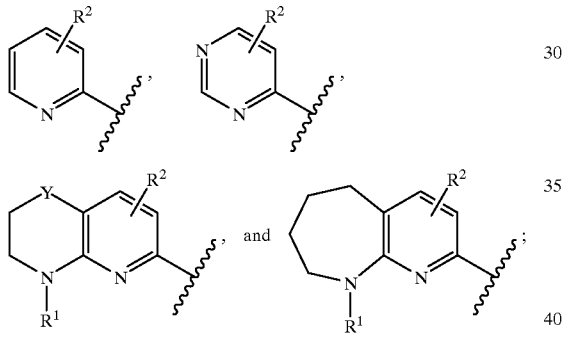

Y is $CH_2$; O; or $NR^1$;

each $R^1$ is independently hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of
halogen, $C_{1-8}$ alkyl, $C_{3-8}$ cycloalkyl,
$C_{3-8}$ cycloheteroalkyl, $C_{3-8}$ cycloalkyl-$C_{1-6}$ alkyl,
$C_{3-8}$ cycloheteroalkyl-$C_{1-6}$ alkyl, aryl, aryl-$C_{1-6}$ alkyl, amino,
amino-$C_{1-6}$ alkyl, $C_{1-3}$ acylamino, $C_{1-3}$ acylamino-$C_{1-6}$ alkyl,
$(C_{1-6}$ alkyl$)_{1-2}$ amino, $C_{3-6}$ cycloalkyl-$C_{0-2}$ amino,
$(C_{1-6}$ alkyl$)_{1-2}$ amino-$C_{1-6}$ alkyl, $C_{1-6}$ alkoxy, $C_{1-4}$ alkoxy-$C_{1-6}$ alkyl,
hydroxycarbonyl, hydroxycarbonyl-$C_{1-6}$ alkyl, $C_{1-3}$ alkoxycarbonyl,
$C_{1-3}$ alkoxycarbonyl-$C_{1-6}$ alkyl, hydroxy, hydroxy-$C_{1-6}$ alkyl,
nitro, cyano, trifluoromethyl, trifluoromethoxy, trifluoroethoxy,
$C_{1-8}$ alkyl-$S(O)_{0-2}$, $(C_{1-8}$ alkyl$)_{0-2}$ aminocarbonyl,
$C_{1-8}$ alkyloxycarbonylamino, $(C_{1-8}$ alkyl$)_{1-2}$ aminocarbonyloxy,
(aryl $C_{1-3}$ alkyl$)_{1-2}$ amino, (aryl$)_{1-2}$ amino,
aryl-$C_{1-3}$ alkylsulfonylamino, and $C_{1-8}$ alkylsulfonylamino;
or two $R^2$ substituents, when on the same non-aromatic carbon atom, are taken together with the carbon atom to which they are attached to form a carbonyl group, or two $R^2$ substituents, together with the carbon atoms to which they are attached, join to form a 4- to 6-membered saturated or unsaturated carbocyclic ring;

$R^3$ and $R^5$ are each independently hydrogen, hydroxy, or $C_{1-6}$ alkoxy;

$R^4$ and $R^6$ are each independently hydrogen or $C_{1-3}$ alkyl; or $R^3$ and $R^4$ taken together or $R^5$ and $R^6$ taken together are carbonyl oxygen, with the proviso that both $R^3$ and $R^5$ are not simultaneously hydrogen;

$R^7$ is aryl wherein the aryl group is selected from the group consisting of
(1) phenyl,
(2) naphthyl,
(3) pyridyl,
(4) furyl,
(5) thienyl,
(6) pyrrolyl,
(7) oxazolyl,
(8) thiazolyl,
(9) imidazolyl,
(10) pyrazolyl,
(11) isoxazolyl,
(12) isothiazolyl,
(13) pyrimidinyl,
(14) pyrazinyl,
(15) pyridazinyl,
(16) tetrazolyl,
(17) quinolyl,
(18) isoquinolyl,
(19) benzimidazolyl,
(20) benzofuryl,
(21) benzothienyl,
(22) indolyl,
(23) benzthiazolyl,
(24) benzoxazolyl,
(25) dihydrobenzofuryl,
(26) benzo(1,3)dioxolanyl,
(27) benzo(1,4)dioxanyl,
(28) quinazolyl,
(29) quinoxalyl, and
(30) 3,4-dihydro-2H-1,4-dioxa-5-aza-naphthalenyl;

wherein the aryl group as defined above in items (1) to (30) is unsubstituted or substituted with one to three substituents independently selected from hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di$(C_{1-6})$alkylamino, $C_{1-6}$ alkylamino-$C_{1-6}$ alkyl, di$(C_{1-6})$ alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; with the proviso that if X is 5,6,7,8-tetrahydro-[1,8]naphthyridin-2-yl, $R^2$ is hydrogen, and aryl is 6-substituted-pyridin-3-yl, then the 6-substituent on the pyridin-3-yl ring is other than methoxy; and $R^8$ is hydrogen or $C_{1-3}$ alkyl;

or a pharmaceutically acceptable salt thereof.

The compounds of the present invention are useful as αv integrin receptor antagonists.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an αv integrin receptor antagonizing effect in a mammal in need thereof by administering the compounds and pharmaceutical compositions of the present invention.

The present invention also relates to methods for inhibiting bone resorption, restenosis, atherosclerosis, inflammation, inflammatory arthritis, viral disease, diabetic retinopathy, macular degeneration, angiogenesis, cancer, and metastatic tumor growth by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention is directed to novel nonanoic acid derivatives described by the structural formula (I)

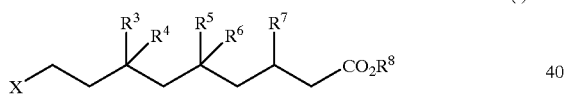

(I)

or a pharmaceutically acceptable salt thereof, wherein:

X is selected from the group consisting of

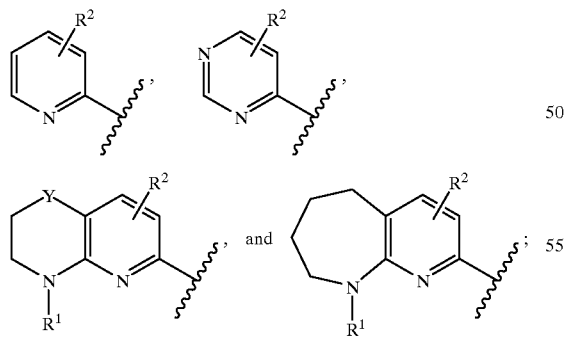

Y is $CH_2$; O; or $NR^1$;

each $R^1$ is independently hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of halogen, $C_{1-8}$ alkyl, $C_{3-8}$ cycloalkyl,
$C_{3-8}$ cycloheteroalkyl, $C_{3-8}$ cycloalkyl-$C_{1-6}$ alkyl,
$C_{3-8}$ cycloheteroalkyl-$C_{1-6}$ alkyl, aryl, aryl-$C_{1-6}$ alkyl, amino,
amino-$C_{1-6}$ alkyl, $C_{1-3}$ acylamino, $C_{1-3}$ acylamino-$C_{1-6}$ alkyl,
$(C_{1-6}$ alkyl$)_{1-2}$ amino, $C_{3-6}$ cycloalkyl-$C_{0-2}$ amino,
$(C_{1-6}$ alkyl$)_{1-2}$ amino-$C_{1-6}$ alkyl, $C_{1-6}$ alkoxy, $C_{1-4}$ alkoxy-$C_{1-6}$ alkyl,
hydroxycarbonyl, hydroxycarbonyl-$C_{1-6}$ alkyl, $C_{1-3}$ alkoxycarbonyl,
$C_{1-3}$ alkoxycarbonyl-$C_{1-6}$ alkyl, hydroxy, hydroxy-$C_{1-6}$ alkyl,
nitro, cyano, trifluoromethyl, trifluoromethoxy, trifluoroethoxy,
$C_{1-8}$ alkyl-S(O)$_{0-2}$, $(C_{1-8}$ alkyl$)_{0-2}$ aminocarbonyl,
$C_{1-8}$ alkyloxycarbonylamino, $(C_{1-8}$ alkyl$)_{1-2}$ aminocarbonyloxy,
(aryl $C_{1-3}$ alkyl)$_{1-2}$ amino, (aryl)$_{1-2}$ amino,
aryl-$C_{1-3}$ alkylsulfonylamino, and $C_{1-8}$ alkylsulfonylamino;

or two $R^2$ substituents, when on the same non-aromatic carbon atom, are taken together with the carbon atom to which they are attached to form a carbonyl group, or two $R^2$ substituents, together with the carbon atoms to which they are attached, join to form a 4- to 6-membered saturated or unsaturated carbocyclic ring;

$R^3$ and $R^5$ are each independently hydrogen, hydroxy, or $C_{1-6}$ alkoxy;

$R^4$ and $R^6$ are each independently hydrogen or $C_{1-3}$ alkyl; or $R^3$ and $R^4$ taken together or $R^5$ and $R^6$ taken together are carbonyl oxygen, with the proviso that both $R^3$ and $R^5$ are not simultaneously hydrogen;

$R^7$ is aryl wherein the aryl group is selected from the group consisting of (1) phenyl,
(2) naphthyl,
(3) pyridyl,
(4) furyl,
(5) thienyl,
(6) pyrrolyl,
(7) oxazolyl,
(8) thiazolyl,
(9) irnidazolyl,
(10) pyrazolyl,
(11) isoxazolyl,
(12) isothiazolyl,
(13) pyrimidinyl,
(14) pyrazinyl,
(15) pyridazinyl,
(16) tetrazolyl,
(17) quinolyl,
(18) isoquinolyl,
(19) benzimidazolyl,
(20) benzofuryl,
(21) benzothienyl,
(22) indolyl,
(23) benzthiazolyl,
(24) benzoxazolyl,
(25) dihydrobenzofuryl,
(26) benzo(1,3)dioxolanyl,
(27) benzo(1,4)dioxanyl,
(28) quinazolyl,
(29) quinoxalyl, and
(30) 3,4-dihydro-2H-1,4-dioxa-5-aza-naphthalenyl;

wherein the aryl group as defined above in items (1) to (30) is unsubstituted or substituted with one to three substituents independently selected from hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; with the proviso that if X is 5,6,7,8-tetrahydro-[1,8]naphthyridin-2-yl, $R^2$ is hydrogen, and aryl is 6-substituted-pyridin-3-yl, then the 6-substituent on the pyridin-3-yl ring is other than methoxy; and $R^8$ is hydrogen or $C_{1-3}$ alkyl.

One embodiment of the present invention is directed to compounds of structural formula (I),

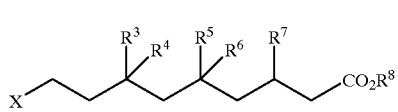

(I)

or a pharmaceutically acceptable salt thereof, wherein X is

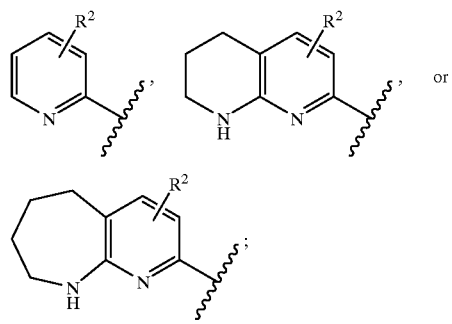

$R^3$ is hydroxy and $R^5$ is hydrogen or $R^5$ is hydroxy and $R^3$ is hydrogen, or $R^3$ and $R^4$ taken together or $R^5$ and $R^6$ taken together are carbonyl oxygen, with the proviso that both $R^3$ and $R^5$ are not simultaneously hydrogen; $R^4$ and $R^6$ are each independently hydrogen or methyl; and $R^2$, $R^7$, and $R^8$ are as defined above.

In one class of this embodiment, $R^7$ is aryl wherein the aryl group is selected from the group consisting of phenyl, pyridyl, quinolyl, pyrimidinyl, pyrazinyl, pyridazinyl, pyrazolyl, benzofuryl, dihydrobenzofuryl, and 3,4-dihydro-2H-1,4-dioxa-5-aza-naphthalenyl, wherein the aryl group is unsubstitued or substituted with one to two substituents as defined above, with the proviso that if X is 5,6,7,8-tetrahydro-[1,8]naphthyridin-2-yl, $R^2$ is hydrogen, and $R^7$ is 6-substituted-pyridin-3-yl, then the 6-substituent on the pyridin-3-yl ring is other than methoxy.

In another class of this embodiment, $R^7$ is quinolyl, pyridyl, or pyrimidinyl, unsubstituted or substituted with one to two substituents independently selected from halogen, phenyl, $C_{1-4}$ alkyl, $C_{3-6}$ cycloalkyl, $C_{1-3}$ alkoxy, amino, $C_{1-3}$ alkylarnino, di($C_{1-3}$) alkylamino, hydroxy, cyano, trifluoromethyl, 1,1,1-trifluoroethyl, trifluoromethoxy, and trifluoroethoxy, with the proviso that if X is 5,6,7,8-tetrahydro-[1,8]naphthyridin-2-yl, $R^2$ is hydrogen, and $R^7$ is 6-substituted-pyridin-3-yl, then the 6-substituent on the pyridin-3-yl ring is other than methoxy.

In a subclass of this class of this embodiment, $R^2$ is selected from the group consisting of hydrogen, halogen, amino, $C_{1-4}$ alkylamino, $C_{3-6}$ cycloalkyl-$C_{0-2}$ alkylamino cyano, $C_{1-4}$ alkyl, cyclopropyl, aryl $C_{1-3}$ alkyl, $C_{1-4}$ acylamino, $C_{1-4}$ alkoxy, $C_{1-4}$ alkylthio, aminocarbonyl, ($C_{1-6}$ alkyl)$_{1-2}$ aminocarbonyl, $C_{1-4}$ alkoxycarbonyl, trifluoromethyl, and trifluoromethoxy.

In a further subclass of this class, $R^2$ is selected from the group consisting of hydrogen, halogen, amino, $C_{1-3}$ alkylamino, $C_{3-6}$ cycloalkylmethylamino, $C_{1-4}$ alkyl, cyclopropyl, trifluoromethyl, and trifluoromethoxy.

Another class of this embodiment is directed to compounds of structural formula (II), or a pharmaceutically acceptable salt thereof,

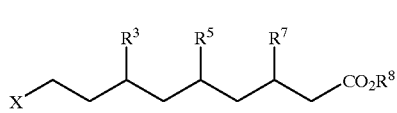

(II)

wherein X is

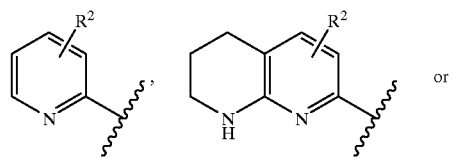

-continued

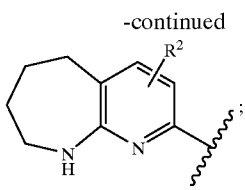

R³ is hydroxy and R⁵ is hydrogen or R⁵ is hydroxy and R³ is hydrogen, with the proviso that both R³ and R⁵ are not simultaneously hydrogen; R² is hydrogen, $C_{1-4}$ alkyl, cyclopropyl, amino, $C_{1-3}$ alkylamino, or cyclopropylmethylamino;

R⁷ is quinolyl, pyridyl, or pyrimidinyl, unsubstituted or substituted with one substituent selected from $C_{1-4}$ alkyl, $C_{3-6}$ cycloalkyl, $C_{1-3}$ alkoxy, amino, $C_{1-3}$ alkylamino, di($C_{1-3}$) alkylamino, cyano, trifluoromethyl, and trifluoromethoxy, with the proviso that if X is 5,6,7,8-tetrahydro[1,8]naphthyridin-2-yl, R² is hydrogen, and R⁷ is 6-substituted-pyridin-3-yl, then the 6-substituent on the pyridin-3-yl ring is other than methoxy; and R⁸ is hydrogen or $C_{1-3}$ alkyl.

A second embodiment of the present invention is directed to compounds of structural formula (III),

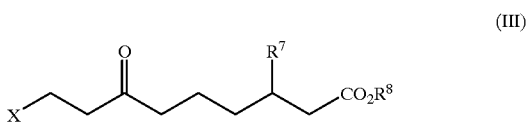

(III)

or a pharmaceutically acceptable salt thereof, wherein X is

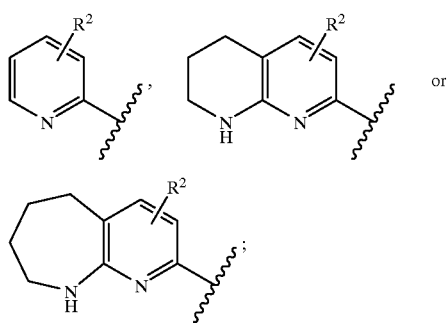

and R², R⁷, and R⁸ are as defined above.

In one class of this embodiment, R⁷ is aryl wherein the aryl group is selected from the group consisting of phenyl, pyridyl, quinolyl, pyrimidinyl, pyrazinyl, pyridazinyl, pyrazolyl, benzofuryl, dihydrobenzofuryl, and 3,4-dihydro-2H-1,4-dioxa-5-aza-naphthalenyl, wherein the aryl group is unsubstituted or substituted with one to two substituents as defined above, with the proviso that if X is 5,6,7,8-tetrahydro-[1,8]naphthyridin-2-yl, R² is hydrogen, and R⁷ is 6-substituted-pyridin-3-yl, then the 6-substituent on the pyridin-3-yl ring is other than methoxy.

In another class of this embodiment, R⁷ is quinolyl, pyridyl, or pyrimidinyl, unsubstituted or substituted with one to two substituents independently selected from halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, and trifluoroethoxy, with the proviso that if X is 5,6,7,8-tetrahydro-[1,8]naphthyridin-2-yl, R² is hydrogen, and R⁷ is 6-substituted-pyridin-3-yl, then the 6-substituent on the pyridin-3-yl ring is other than methoxy.

In a subclass of this class, R² is selected from the group consisting of
hydrogen,
halogen,
amino,
$C_{1-4}$ alkylamino,
$C_{3-6}$ cycloalkyl-$C_{1-2}$ alkylamino cyano,
$C_{1-4}$ alkyl,
cyclopropyl,
aryl $C_{1-3}$ alkyl,
$C_{1-4}$ acylamino,
$C_{1-4}$ alkoxy,
$C_{1-4}$ alkylthio,
aminocarbonyl,
($C_{1-6}$ alkyl)$_{1-2}$ aminocarbonyl,
$C_{1-4}$ alkoxycarbonyl,
trifluoromethyl, and
trifluoromethoxy.

In a further subclass of this class, R² is selected from the group consisting of
hydrogen,
halogen,
amino,
$C_{1-3}$ alkylamino,
$C_{3-6}$ cycloalkylmethylamino,
$C_{1-4}$ alkyl,
cyclopropyl,
trifluoromethyl, and
trifluoromethoxy.

Another class of this second embodiment is directed to compounds of structural formula (III),

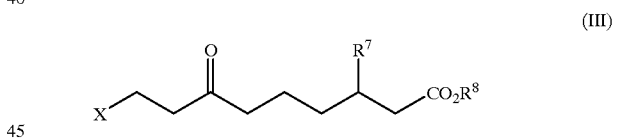

(III)

or a pharmaceutically acceptable salt thereof, wherein X is

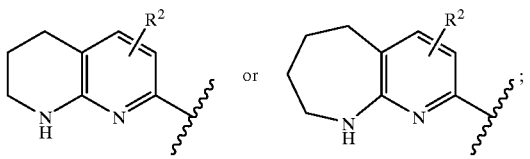

R² is hydrogen, $C_{1-4}$ alkyl, or cyclopropyl;

R⁷ is quinolyl, pyridyl, or pyrimidinyl, unsubstituted or substituted with one substituent selected from $C_{1-4}$ alkyl, $C_{3-6}$ cycloalkyl, $C_{1-3}$ alkoxy, amino, $C_{1-3}$ alkylamino, di($C_{1-3}$) alkylamino, cyano, trifluoromethyl, and trifluoromethoxy, with the proviso that if X is 5,6,7,8-tetrahydro[1,8]naphthyridin-2-yl, R² is hydrogen, and R⁷ is 6-substituted-pyridin-3-yl, then the 6-substituent on the pyridin-3-yl ring is other than methoxy; and R⁸ is hydrogen or $C_{1-3}$ alkyl.

A third embodiment of the present invention is directed to compounds of structural formula (IV):

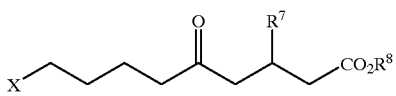
(IV)

or a pharmaceutically acceptable salt thereof, wherein X is

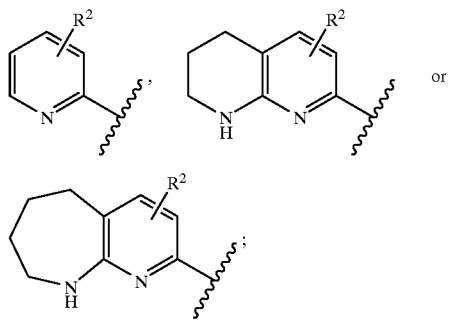

and $R^2$, $R^7$, and $R^8$ are as defined above.

In one class of this embodiment, $R^7$ is aryl wherein the aryl group is selected from the group consisting of phenyl, pyridyl, quinolyl, pyrimidinyl, pyrazinyl, pyridazinyl, pyrazolyl, benzofuryl, dihydrobenzofuryl, and 3,4-dihydro-2H-1,4-dioxa-5-aza-naphthalenyl, wherein the aryl group is unsubstituted or substituted with one to two substituents as defined above, with the proviso that if X is 5,6,7,8-tetrahydro-[1,8]naphthyridin-2-yl, $R^2$ is hydrogen, and $R^7$ is 6-substituted-pyridin-3-yl, then the 6-substituent on the pyridin-3-yl ring is other than methoxy.

In another class of this embodiment, $R^7$ is quinolyl, pyridyl, or pyrimidinyl, unsubstituted or substituted with one to two substituents independently selected from halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, and trifluoroethoxy, with the proviso that if X is 5,6,7,8-tetrahydro-[1,8]naphthyridin-2-yl, $R^2$ is hydrogen, and $R^7$ is 6-substituted-pyridin-3-yl, then the 6-substituent on the pyridin-3-yl ring is other than methoxy.

In a subclass of this class, $R^2$ is selected from the group consisting of
hydrogen,
halogen,
amino,
$C_{1-4}$ alkylamino,
$C_{3-6}$ cycloalkyl-$C_{0-2}$ alkylamino cyano,
$C_{1-4}$ alkyl,
cyclopropyl,
aryl $C_{1-3}$ alkyl,
$C_{1-4}$ acylamino,
$C_{1-4}$ alkoxy,
$C_{1-4}$ alkylthio,
aminocarbonyl,
($C_{1-6}$ alkyl)$_{1-2}$ aminocarbonyl,
$C_{1-4}$ alkoxycarbonyl,
trifluoromethyl, and
trifluoromethoxy.

In a further subclass of this class, $R^2$ is selected from the group consisting of
hydrogen,
halogen,
amino,
$C_{1-3}$ alkylamino,
$C_{3-6}$ cycloalkylmethylamino,
$C_{1-4}$ alkyl,
cyclopropyl,
trifluoromethyl, and
trifluoromethoxy.

Another class of this third embodiment is directed to compounds of structural formula (IV):

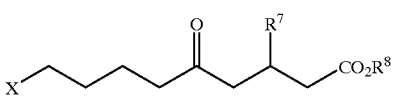
(IV)

or a pharmaceutically acceptable salt thereof, wherein X is:

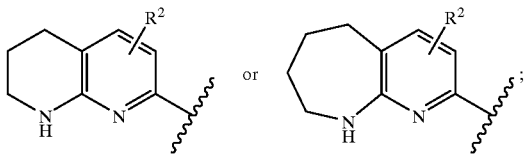

$R^2$ is hydrogen, $C_{1-4}$ alkyl, or cyclopropyl;
$R^7$ is quinolyl, pyridyl, or pyrimidinyl, unsubstituted or substituted with one substituent selected from $C_{1-4}$ alkyl, $C_{3-6}$ cycloalkyl, $C_{1-3}$ alkoxy, amino, $C_{1-3}$ alkylamino, di($C_{1-3}$) alkylamino, cyano, trifluoromethyl, or trifluoromethoxy, with the proviso that if X is 5,6,7,8-tetrahydro[1,8]naphthyridin-2-yl, $R^2$ is hydrogen, and $R^7$ is 6-substituted-pyridin-3-yl, then the 6-substituent on the pyridin-3-yl ring is other than methoxy; and
$R^8$ is hydrogen or $C_{1-3}$ alkyl.

Additional embodiments of the present invention are directed to compounds of formulae I–IV wherein $R^8$ is hydrogen.

The compounds of the present invention of structural formula (I) wherein $R^3$ is hydrogen, $R^5$ is hydroxy, and $R^8$ is hydrogen, such as in structural formula (V), can also exist in the ring-closed δ-lactone form of structural formula (VI).

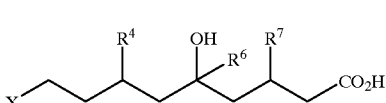
(V)

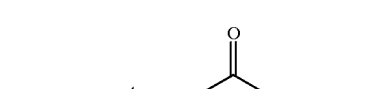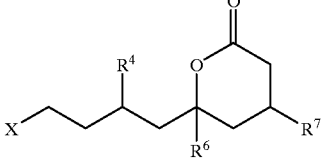
(VI)

Illustrative but nonlimiting examples of compounds of the present invention that are useful as αv integrin receptor antagonists are the following:

3-(Pyrimidin-5-yl)-5-oxo-9-(5,6,7,8-tetrahydro-[1,8]-naphthyridin-2-yl)-nonanoic acid;

3(R)-(Pyrimidin-5-yl)-5-oxo-9-(5,6,7,8-tetrahydro-[1,8]-naphthyridin-2-yl)-nonanoic acid;

3(S)-(Pyrimidin-5-yl)-5-oxo-9-(5,6,7,8-tetrahydro-[1,8]-naphthyridin-2-yl)-nonanoic acid;

3-(2-Methyl-pyrimidin-5-yl)-5-oxo-9-(5,6,7,8-tetrahydro-[1,8]-naphthyridin-2-yl)-nonanoic acid;

3(R)-(2-Methyl-pyrimidin-5-yl)-5-oXo-9-(5,6,7,8-tetrahydro-[1,8]-naphthyridin-2-yl)-nonanoic acid;

3(S)-(2-Methyl-pyrimidin-5-yl)-5-oxo-9-(5,6,7,8-tetrahydro-[1,8]-naphthyridin-2-yl)-nonanoic acid;

3-(2-Cyclopropyl-pyrimidin-5-yl)-5-oxo-9-(5,6,7,8-tetrahydro-[1,8]-naphthyridin-2-yl)-nonanoic acid;

3(R)-(2-Cyclopropyl-pyrimidin-5-yl)-5-oxo-9-(5,6,7,8-tetrahydro-[1,8]-naphthyridin-2-yl)-nonanoic acid;

3(S)-(2-Cyclopropyl-pyrimidin-5-yl)-5-oxo-9-(5,6,7,8-tetrahydro-[1,8]-naphthyridin-2-yl)-nonanoic acid;

3-(2-Methyl-pyrimidin-5-yl)-5-hydroxy-9-(5,6,7,8-tetrahydro-[1,8]-naphthyridin-2-yl)-nonanoic acid;

3(R)-(2-Methyl-pyrimidin-5-yl)-5-hydroxy-9-(5,6,7,8-tetrahydro-[1,8]-naphthyridin-2-yl)-nonanoic acid;

3(S)-(2-Methyl-pyrimidin-5-yl)-5-hydroxy-9-(5,6,7,8-tetrahydro-[1,8]-naphthyridin-2-yl)-nonanoic acid;

3-(2-Methyl-pyrimidin-5-yl)-5-oxo-9-(3-methyl-5,6,7,8-tetrahydro-[1,8]-naphthyridin-2-yl)-nonanoic acid;

3(R)-(2-Methyl-pyrimidin-5-yl)-5-oxo-9-(3-methyl-5,6,7,8-tetrahydro-[1,8]-naphthyridin-2-yl)-nonanoic acid;

3(S)-(2-Methyl-pyrimidin-5-yl)-5-oxo-9-(3-methyl-5,6,7,8-tetrahydro-[1,8]-naphthyridin-2-yl)-nonanoic acid;

3-(2-Methyl-pyrimidin-5-yl)-7-oxo-9-(5,6,7,8-tetrahydro-[1,8]-naphthyridin-2-yl)-nonanoic acid;

3(R)-(2-Methyl-pyrimidin-5-yl)-7-oxo-9-(5,6,7,8-tetrahydro-[1,8]-naphthyridin-2-yl)-nonanoic acid;

3(S)-(2-Methyl-pyrimidin-5-yl)-7-oxo-9-(5,6,7,8-tetrahydro-[1,8]-naphthyridin-2-yl)-nonanoic acid;

3-(Quinolin-3-yl)-5-oxo-9-(5,6,7,8-tetrahydro-[1,8]-naphthyridin-2-yl)-nonanoic acid;

3(R)-(Quinolin-3-yl)-5-oxo-9-(5,6,7,8-tetrahydro-[1,8]-naphthyridin-2-yl)-nonanoic acid;

3(S)-(Quinolin-3-yl)-5-oxo-9-(5,6,7,8-tetrahydro-[1,8]-naphthyridin-2-yl)-nonanoic acid;

3-(Quinolin-3-yl)-5-hydroxy-9-(5,6,7,8-tetrahydro-[1,8]-naphthyridin-2-yl)-nonanoic acid;

3(R)-(Quinolin-3-yl)-5-hydroxy-9-(5,6,7,8-tetrahydro-[1,8]-naphthyridin-2-yl)-nonanoic acid;

3(S)-(Quinolin-3-yl)-5-hydroxy-9-(5,6,7,8-tetrahydro-[1,8]-naphthyridin-2-yl)-nonanoic acid;

3-(6-Ethoxy-pyridin-3-yl)-5-oxo-9-(5,6,7,8-tetrahydro-[1,8]-naphthyridin-2-yl)-nonanoic acid;

3(R)-(6-Ethoxy-pyridin-3-yl)-5-oxo-9-(5,6,7,8-tetrahydro-[1,8]-naphthyridin-2-yl)-nonanoic acid;

3(S)-(6-Ethoxy-pyridin-3-yl)-5-oxo-9-(5,6,7,8-tetrahydro-[1,8]-naphthyridin-2-yl)-nonanoic acid;

3-(6-Methoxy-pyridin-3-yl)-5-oxo-9-(3-methyl-5,6,7,8-tetrahydro-[1,8]-naphthyridin-2-yl)-nonanoic acid;

3(R)-(6-Methoxy-pyridin-3-yl)-5-oxo-9-(3-methyl-5,6,7,8-tetrahydro-[1,8]-naphthyridin-2-yl)-nonanoic acid;

3(S)-(6-Methoxy-pyridin-3-yl)-5-oxo-9-(3-methyl-5,6,7,8-tetrahydro-[1,8]-naphthyridin-2-yl)-nonanoic acid;

3-(2-Methyl-p din-5-yl)-5-oxo-9-(3-cyclopropyl-5,6,7,8-tetrahydro-[1,8]-naphthyridin-2-yl)-nonanoic acid;

3(R)-(2-Methyl-pyrimidin-5-yl)-5-oxo-9-(3-cyclopropyl-5,6,7,8-tetrahydro-[1,8]-naphthyridin-2-yl)-nonanoic acid;

3(S)-(2-Methyl-pyrimidin-5-yl)-5-oxo-9-(3-cyclopropyl-5,6,7,8-tetrahydro-[1,8]-naphthyridin-2-yl)-nonanoic acid;

3-(2-Methoxy-pyrimidin-5-yl)-5-oxo-9-(3-cyclopropyl-5,6,7,8-tetrahydro-[1,8]-naphthyridin-2-yl)-nonanoic acid;

3(R)-(2-Methoxy-pyrimidin-5-yl)-5-oxo-9-(3-cyclopropyl-5,6,7,8-tetrahydro-[1,8]-naphthyridin-2-yl)-nonanoic acid;

3(S)-(2-Methoxy-pyrinidin-5-yl)-5-oxo-9-(3-cyclopropyl-5,6,7,8-tetrahydro-[1,8]-naphthyridin-2-yl)-nonanoic acid;

3-(2-Isopropyl-pyrimidin-5-yl)-5-oxo-9-(5,6,7,8-tetrahydro[1,8]naphthyridin-2-yl)-nonanoic acid;

3(R)-(2-Isopropyl-pyrimidin-5-yl)-5-oxo-9-(5,6,7,8-tetrahydro[1,8]naphthyridin-2-yl)-nonanoic acid;

3(S)-(2-Isopropyl-pyrimidin-5-yl)-5-oxo-9-(5,6,7,8-tetrahydro[1,8]naphthyridin-2-yl)-nonanoic acid;

3-(2-tert-Butyl-pyrimidin-5-yl)-5-oxo-9-(5,6,7,8-tetrahydro[1,8]naphthyridin-2-yl)-nonanoic acid;

3(R)-(2-tert-Butyl-pyrimidin-5-yl)-5-oxo-9-(5,6,7,8-tetrahydro[1,8]naphthyridin-2-yl)-nonanoic acid;

3(S)-(2-tert-Butyl-pyrimidin-5-yl)-5-oxo-9-(5,6,7,8-tetrahydro[1, 8]naphthyridin-2-yl)-nonanoic acid;

3-(2-Ethoxy-pyrimidin-5-yl)-5-oxo-9-(5,6,7,8tetrahydro[[1,8]naphthyridin-2-yl)-nonanoic acid;

3(R)-(2-Ethoxy-pyrimidin-5-yl)-5-oxo-9-(5 ,6 ,7,8-tetrahydro[1,8]naphthyiidin-2-yl)-nonanoic acid;

3(S)-(2-Ethoxy-pyrimidin-5-yl)-5-oxo-9-(5,6,7 ,8-tetrahydro[1,8]naphthyridin-2-yl)-nonanoic acid;

3-(2-Methoxy-pyrimidin-5-yl)-5-oxo-9-(5,6,7,8-tetrahydro[1,8]naphthyridin-2-yl)-nonanoic acid;

3(R)-(2-Methoxy-pyrimidin-5-yl)-5-oxo-9-(5,6,7,8-tetrahydro[1,8]naphthyridin-2-yl)-nonanoic acid;

3(S)-(2-Methoxy-pyrimidin-5-yl)-5-oxo-9-(5,6,7,8-tetrahydro[1,8]naphthyridin-2-yl)-nonanoic acid;

3-(Quinoxalin-2-yl)-5-oxo-9-(5,6,7,8-tetrahydro[1,8]naphthyridin-2-yl)-nonanoic acid;

3(R)-(Quinoxalin-2-yl)-5-oxo-9-(5,6,7,8-tetrahydro [1,8]naphthyridin-2-yl)-nonanoic acid;

3-(2-Methyl-pyrimidin-5-yl)-5-oxo-9-(6,7,8,9-tetrahydro-5H-pyrido[2,3-b]azepin-2-yl acid;

3(R)-(2-Methyl-pyrimidin-5-yl)-5-oxo-9-(6,7,8,9-tetrahydro-5H-pyrido[2,3-b]azepin-2-yl)-nonanoic acid;

3(S)-(2-Methyl-pyrimidin-5-yl)-5-oxo-9-(6,7,8,9-tetrahydro-5H-pyrido[2,3-b]azepin-2-yl)-nonanoic acid;

3-(2-Methoxy-pyrimidin-5-yl)-5-oxo-9-(6,7,8,9-tetrahydro-5H-pyrido[2,3-b]azepin-2-yl)-nonanoic acid;

3(R)-(2-Methoxy-pyrimidin-5-yl)-5-oxo-9-(6,7,8,9-tetrahydro-5H-pyrido[2,3-b]azepin-2-yl)-nonanoic acid;

3(S)-(2-Methoxy-pyrimidin-5-yl)-5-oxo-9-(6,7,8,9-tetrahydro-5H-pyrido[2,3-b]azepin-2-yl)-nonanoic acid;

3-(2,3-Dihydro-benzofuran-6-yl)-5-oxo-9-(5,6,7,8-tetrahydro-[I,8]naphthyridin-2-yl)-nonanoic acid;

3(R)-(2,3-Dihydro-benzofuran-6-yl)-5-oxo-9-(5,6,7,8-tetrahydro-[1,8]naphthyridin-2-yl)-nonanoic acid;

3(S)-(2,3-Dihydro-benzofuran-6-yl)-5-oxo-9-(5,6,7,8-tetrahydro-[1,8]naphthyridin-2-yl)-nonanoic acid;

9-(6-Methylarnino-pyridin-2-yl)-5-oxo-3-(pyrinidin-5-yl)-nonanoic acid;

3(R)-9-(6-Methylamino-pyridin-2-yl)-5-oxo-3-(pyrimidin-5-yl)-nonanoic acid;

3(S)-9-(6-Methylamino-pyridin-2-yl)-5-oxo-3-(pyrimidin-5-yl)-nonanoic acid;

9-(2-Arnino-3,5-dimethylpyridin-6-yl)-3-(2-methoxypyrirnidin-5-yl)-5-oxo-nonanoic acid;

9-(2,4-Diaminopyrimidin-6-yl)-3-(2-methyl-pyrimidin-5-yl)-5-oxo-nonanoic acid;

3-(2-Ethoxy-pyrimdin-5-yl)-5-oxo-9-(6,7,8,9-tetrahydro-5H-pyrido[2,3-b]azepin-2-yl)-nonanoic acid;

3(R)-(2-Ethoxy-pyrimidin-5-yl)-5-oxo-9-(6,7,8,9-tetrahydro-5H-pyrido[2,3-b]azepin-2-yl)-nonanoic acid;

3(S)-(2-Ethoxy-pyrimidin-5-yl)-5-oxo-9-(6,7,8,9-tetrahydro-5H-pyrido[2,3-b]azepin-2-yl)-nonanoic acid;

3-(Pyrazin-2-yl)-5-oxo-9-(5,6,7,8-tetrahydro-[1,8]naphthyridin-2-yl)-nonanoic acid;

3(R)-(Pyrazin-2-yl)-5-oxo-9-(5,6,7,8-tetrahydro-[1,8]naphthyridin-2-yl)-nonanoic acid;

3(S)-(Pyrazin-2-yl)-5-oxo-9-(5,6,7,8-tetrahydro-[1,8]naphthyridin-2-yl)-nonanoic acid;

3-(2-Methyl-pyrazin-5-yl)-5-oxo-9-(5 ,6,7,8-tetrahydro-[I ,8]naphthyridin-2-yl)-nonanoic acid;

3(R)-(2-Methyl-pyrazin-5-yl)-5-oxo-9-(5,6,7,8-tetrahydro-[1,8]naphthyridin-2-yl)-nonanoic acid;

3(S)-(2-Methyl-pyrazin-5-yl)-5-oxo-9-(5,6,7,8-tetrahydro-[1,8]naphthyridin-2-yl)-nonanoic acid;

3-(6-Methoxy-pyridazin-3-yl)-5-oxo-9-(5,6,7,8-tetrahydro-[1,8]naphthyridin-2-yl)-nonanoic acid;

3(R)-(6-Methoxy-pyridazin-3-yl)-5-oxo-9-(5,6,7,8-tetrahydro-[,8]naphthyridin-2-yl)-nonanoic acid;

3(S)-(6-Methoxy-pyridazin-3-yl)-5-oxo-9-(5,6,7,8-tetrahydro-[1,8]naphthyridin-2-yl)-nonanoic acid;

3-(2-Methylamino-pyrimidin-5-yl)-5-oxo-9-(5,6,7,8-tetrahydro-[1,8]naphthyridin-2-yl)-nonanoic acid;

3(R)-(2-Methylamino-pyrimidin-5-yl)-5-oxo-9-(5,6,7,8-tetrahydro-[1,8]naphthyridin-2-yl)-nonanoic acid;

3(S)-(2-Methylaniino-pyrimidin-5-yl)-5-oxo-9-(5,6,7,8-tetrahydro-[1,8]naphthyridin-2-yl)-nonanoic acid;

3-(3,4-Dihydro-2H-1,4-dioxa-5-aza-naphthalen-7-yl)-5-oxo-9-(5,6,7,8-tetrahydro-[1,8]naphthyridin-2-yl)-nonanoic acid;

3(R)-(3,4-Dihydro-2H-1,4-dioxa-5-aza-naphthalen-7-yl)-5-oxo-9-(5,6,7,8-tetrahydro-[1,8]naphthyridin-2-yl)-nonanoic acid;

3(S)-(3,4-Dihydro-2H-1,4-dioxa-5-aza-naphthalen-7-yl)-5-oxo-9-(5,6,7,8-tetrahydro-[1,8]naphthyridin-2-yl)-nonanoic acid;

3-(2-Methyl-pyrimidin-5-yl)-5-oxo-9-(6-methyl-5,6,7,8-tetrahydro-[1,8]naphthyridin-2-yl)-nonanoic acid;

3(R)-(2-Methyl-pyrimidin-5-yl)-5-oxo-9-(6-methyl-5,6,7,8-tetrahydro-[1,8]naphthyridin-2-yl)-nonanoic acid;

3(S)-(2-Methyl-pyrimidin-5-yl)-5-oxo-9-(6-methyl-5,6,7,8-tetrahydro-[1,8]naphthyridin-2-yl)-nonanoic acid;

3-(Benzofuran-6-yl)-5-oxo-9-(5,6,7,8-tetrahydro-[1,8]naphthyridin-2-yl)-nonanoic acid;

3(R)-(Benzofuran-6-yl)-5-oxo-9-(5,6,7,8-tetrahydro-[1,8]naphthyridin-2-yl)-nonanoic acid;

3(S)-(Benzofuran-6-yl)-5-oxo-9-(5,6,7,8-tetrahydro-[1,8]naphthyridin-2-yl)-nonanoic acid;

3-(5-Methoxy-pyridin-3-yl)-5-oxo-9-(5,6,7,8-tetrahydro-[1,8]naphthyridin-2-yl)-nonanoic acid;

3(R)-(5-Methoxy-pyridin-3-yl)-5-oxo-9-(5,6,7,8-tetrahydro-[1,8]naphthyridin-2-yl)-nonanoic acid;

3(S)-(5-Methoxy-pyridin-3-yl)-5-oxo-9-(5,6,7,8-tetrahydro-[1,8]naphthyridin-2-yl)-nonanoic acid;

3-(2-Ethoxy-pyrimidin-5-yl)-5-oxo-9-(5,6,7,8-tetrahydro-5H-pyrido[2,3-b]azepin-2-yl)-nonanoic acid;

3(R)-(2-Ethoxy-pyrimidin-5-yl)-5-oxo-9-(5 ,6,7,8-tetrahydro-5H-pyrido[2,3-b]azepin-2-yl)-nonanoic acid;

3(S)-(2-Ethoxy-pyrimidin-5-yl)-5-oxo-9-(5,6,7,8-tetrahydro-5H-pyrido[2,3-b]azepin-2-yl)-nonanoic acid;

3-(2-Methyl-pyrimidin-5-yl)-5-oxo-9-(3-vinyl-5,6,7,8-tetrahydro-[1,8]naphthynidin-2-yl)-nonanoic acid;

3(R)-(2-Methyl-pyrimidin-5-yl)-5-oxo-9-(3-vinyl-5,6,7,8-tetrahydro-[1,8]naphthyridin-2-yl)-nonanoic acid;

3(S)-(2-Methyl-pyrimidin-5-yl)-5-oxo-9-(3-vinyl-5,6,7,8-tetrahydro-[1,8]naphthyridin-2-yl)-nonanoic acid;

3-(2-Methyl-pyrimidin-5-yl)-5-oxo-9-(3-chloro-5,6,7,8-tetrahydro-[1,8]naphthyridin-2-yl)-nonanoic acid;

3(R)-(2-Methyl-pyrimidin-5-yl)-5-oxo-9-(3-chloro-5,6,7,8-tetrahydro-[1,8]naphthyridin-2-yl)-nonanoic acid;

3(S)-(2-Methyl-pyrimidin-5-yl)-5-oxo-9-(3-chloro-5,6,7,8-tetrahydro-[1,8]naphthyridin-2-yl)-nonanoic acid;

3-(2-Methyl-pyrimidin-5-yl)-5-oxo-9-(3-bromo-5,6,7,8-tetrahydro-[1,8]naphthyridin-2-yl)-nonanoic acid;

3(R)-(2-Methyl-pyrimidin-5-yl)-5-oxo-9-(3-bromo-5,6,7,8-tetrahydro-[1,8]naphthyridin-2-yl)-nonanoic acid;

3(S)-(2-Methyl-pyrimidin-5-yl)-5-oxo-9-(3-bromo-5,6,7,8-tetrahydro-[1,8]naphthyridin-2-yl)-nonanoic acid;

3-(2-Methoxy-pyrimidin-5-yl)-5-oxo-9-(3-methyl-5,6,7,8-tetrahydro-[1,8]naphthyridin-2-yl)-nonanoic acid;

3(R)-(2-Methoxy-pyrimidin-5-yl)-5-oxo-9-(3-methyl-5,6,7,8-tetrahydro-[1,8]naphthyridin-2-yl)-nonanoic acid;

3(S)-(2-Methoxy-pyrimidin-5 -yl)-5-oxo-9-(3methyl-5,6,7,8-tetrahydro-[1,8]naphthyridin-2-yl)-nonanoic acid;

3-(Quinolin-3-yl)-5-oxo-9-(3-methyl-5,6,7,8-tetrahydro-[1,8]naphthyridin-2-yl)-nonanoic acid;

3(R)-(Quinolin-3-yl)-5-oxo-9-(3-methyl-5,6,7,8-tetrahydro-[1,8]naphthyridin-2-yl)-nonanoic acid;

3(S)-(Quinolin-3-yl)-5-oxo-9-(3-methyl-5,6,7,8-tetrahydro-[1,8]naphthyridin-2-yl)-nonanoic acid;

3-(2-Methyl-pyrimidin-5-yl)-5-oxo-7,7-dimethyl-9-(5,6,7,8-tetrahydro-[1,8]naphthyridin-2-yl)-nonanoic acid;

3(R)-(2-Methyl-pyrimidin-5-yl)-5-oxo-7,7-dimethyl-9-(5,6,7,8-tetrahydro-[1,8]naphthyridin-2-yl)-nonanoic acid;

3(S)-(2-Methyl-pyrimidin-5-yl)-5-oxo-7,7-dimethyl-9-(5,6,7,8-tetrahydro-[1,8]naphthyridin-2-yl)-nonanoic acid;

3-(2-Ethoxy-pyrimidin-5-yl)-5-oxo-9-(3-cyclopropyl-5,6,7,8-tetrahydro-[1,8]naphthyridin-2-yl)-nonanoic acid;

3(R)-(2-Ethoxy-pyrimidin-5-yl)-5-oxo-9-(3-cyclopropyl-5,6,7,8-tetrahydro-[1,8]naphthyridin-2-yl)-nonanoic acid;

3(S)-(2-Ethoxy-pyrimidin-5-yl)-5-oxo-9-(3-cyclopropyl-5,6,7,8-tetrahydro-[1,8]naphthyridin-2-yl)-nonanoic acid;

3-(6-Methoxy-pyridin-3-yl)-5-oxo-9-(3-cyclopropyl-5,6,7,8-tetrahydro-[1,8]naphthyridin-2-yl)-nonanoic acid;

3(R)-(6-Methoxy-pyridin-3-yl)-5-oxo-9-(3-cyclopropyl-5,6,7,8-tetrahydro-[1,8]naphthyridin-2-yl)-nonanoic acid;

3(S)-(6-Methoxy-pyridin-3-yl)-5-oxo-9-(3-cyclopropyl-5,6,7,8-tetrahydro-[1,8]naphthyridin-2-yl)-nonanoic acid;

3-(2-Dimethylamino-pyrimidin-5-yl)-5-oxo-9-(5,6,7,8-tetrahydro-[1,8]naphthyridin-2-yl)-nonanoic acid;

3(R)-(2-Dimethylamino-pyrimidin-5-yl)-5-oxo-9-(5,6,7,8-tetrahydro-[1,8]naphthyridin-2-yl)-nonanoic acid; and 3(S)-(2-Dimethylamino-pyrimidin-5-yl)-5-oxo-9-(5,6,7,8-tetrahydro-[1,8]naphthyridin-2-yl)-nonanoic acid;

or a pharmaceutically acceptable salt thereof.

Further illustrative of the present invention are compounds selected from the group consisting of:

3(R)-(Pyrimidin-5-yl)-5-oxo-9-(5,6,7,8-tetrahydro-[1,8]-naphthyridin-2-yl)-nonanoic acid;

3(S)-(Pyrimidin-5-yl)-5-oxo-9-(5,6,7,8-tetrahydro-[1,8]-naphthyridin-2-yl)-nonanoic acid;

3(R)-(2-Methyl-pyrimidin-5-yl)-5-oxo-9-(5,6,7,8-tetrahydro-[1,8]-naphthyridin-2-yl)-nonanoic acid;

3(S)-(2-Methyl-pyrimidin-5-yl)-5-oxo-9-(5,6,7,8-tetrahydro-[1,8]-naphthyridin-2-yl)-nonanoic acid;

3(R)-(2-Cyclopropyl-pyrimidin-5-yl)-5-oxo-9-(5,6,7,8-tetrahydro-[1,8]-naphthyridin-2-yl)-nonanoic acid;

3(S)-(2-Cyclopropyl-pyrimidin-5-yl)-5-oxo-9-(5,6,7,8-tetrahydro-[1,8]-naphthyridin-2-yl)-nonanoic acid;

3(R)-(2-Methyl-pyrimidin-5-yl)-5-hydroxy-9-(5,6,7,8-tetrahydro-[8]-naphthyridin-2-yl)-nonanoic acid;

3(S)-(2-Methyl-pyrimidin-5-yl)-5-hydroxy-9-(5,6,7,8-tetrahydro-[1,8]-naphthyridin-2-yl)-nonanoic acid;

3(R)-(2-Methyl-pyrimidin-5-yl)-5-oxo-9-(3-methyl-5,6,7,8-tetrahydro-[1,8]-naphthyridin-2-yl)-nonanoic acid;

3(S)-(2-Methyl-pyrimidin-5-yl)-5-oxo-9-(3-methyl-5,6,7,8-tetrahydro-[1,8]-naphthyridin-2-yl)-nonanoic acid;

3(R)-(2-Methyl-pyrimidin-5-yl)-7-oxo-9-(5,6,7,8-tetrahydro-[1,8]-naphthyridin-2-yl)-nonanoic acid;

3(S)-(2-Methyl-pyrimidin-5-yl)-7-oxo-9-(5,6,7,8-tetrahydro-[1,8]-naphthyridin-2-yl)-nonanoic acid;

3(R)-(Quinolin-3-yl)-5-oxo-9-(5,6,7,8-tetrahydro-[1,8]-naphthyridin-2-yl)-nonanoic acid;

3(S)-(Quinolin-3-yl)-5-oxo-9-(5,6,7,8-tetrahydro-[1,8]-naphthyridin-2-yl)-nonanoic acid;

3(R)-(Quinolin-3-yl)-5-hydroxy-9-(5,6,7,8-tetrahydro-[1,8]-naphthyridin-2-yl)-nonanoic acid;

3(S)-(Quinolin-3-yl)-5-hydroxy-9-(5,6,7,8-tetrahydro-[1,8]-naphthyridin-2-yl)-nonanoic acid;

3(R)-(6-Ethoxy-pyridin-3-yl)-5-oxo-9-(5,6,7,8-tetrahydro-[1,8]-naphthyridin-2-yl)-nonanoic acid;

3(S)-(6-Ethoxy-pyridin-3-yl)-5-oxo-9-(5,6,7,8-tetrahydro-[1,8]-naphthyridin-2-yl)-nonanoic acid;

3(R)-(6-Methoxy-pyridin-3-yl)-5-oxo-9-(3-methyl-5,6,7,8-tetrahydro-[1,8]-naphthyridin-2-yl)-nonanoic acid;

3(S)-(6-Methoxy-pyridin-3-yl)-5-oxo-9-(3-methyl-5,6,7,8-tetrahydro-[1,8]-naphthyridin-2-yl)-nonanoic acid;

3(R)-(2-Methyl-pyrimidin-5-yl)-5-oxo-9-(3-cyclopropyl-5,6,7,8-tetrahydro [1,8]naphthyridin-2-yl)-nonanoic acid;

3(S)-(2-Methyl-pyrimidin-5-yl)-5-oxo-9-(3-cyclopropyl-5,6,7,8-tetrahydro [1,8]naphthyridin-2-yl)-nonanoic acid;

3(R)-(2-Methoxy-pyrimidin-5-yl)-5-oxo-9-(3-cyclopropyl-5,6,7,8-tetrahydro-[1,8]naphthyridin-2-yl)-nonanoic acid;

3(S)-(2-Methoxy-pyrimidin-5-yl)-5-oxo-9-(3-cyclopropyl-5,6,7,8-tetrahydro-[1,8]naphthyridin-2-yl)-nonanoic acid;

3(R)-(2-Isopropyl-pyrimidin-5-yl)-5-oxo-9-(5,6,7,8-tetrahydro[1,8]naphthyridin-2-yl)-nonanoic acid;

3(S)-(2-Isopropyl-pyrimidin-5-yl)-5-oxo-9-(5,6,7,8-tetrahydro[1,8]naphthyridin-2-yl)-nonanoic acid;

3(R)-(2-tert-Butyl-pyrimidin-5-yl)-5-oxo-9-(5,6,7,8tetrahydro[1,8]naphthytidin-2-yl)-nonanoic acid;

3(S)-(2-tert-Butyl-pyrimidin-5-yl)-5-oxo-9-(5,6,7,8-tetrahydro[1,8]naphthyridin-2-yl)-nonanoic acid;

3(R)-(2-Ethoxy-pyrimidin-5-yl)-5-oxo-9-(5,6,7,8-tetrahydro[1,8]naphthyridin-2-yl)-nonanoic acid;

3(S)-(2-Ethoxy-pyrimidin-5-yl)-5-oxo-9-(5,6,7,8-tetrahydro[1,8]naphthyridin-2-yl)-nonanoic acid;

3(R)-(2-Methoxy-pyrimidin-5-yl)-5-oxo-9-(5,6,7,8-tetrahydro[1,8]naphthyridin-2-yl)-nonanoic acid;

3(S)-(2-Methoxy-pyrimidin-5-yl)-5-oxo-9-(5,6,7,8-tetrahydro[1,8]naphthyridin-2-yl)-nanoanoic acid;

3(S)-(2-Methoxy-pyrimidin-5-yl)-5-oxo-9-(5,6,7,8-tetrahydro[1,8]naphthyridin-2-yl)-nonanoic acid;

3(R)-(Quinoxalin-2-yl)-5-oxo-9-(5,6,7,8-tetrahydro[1,8]naphthyridin-2-yl)-nonanoic acid;

3(S)-(Quinoxalin-2-yl)-5-oxo-9-(5,6,7,8-tetrahydro[1,8]naphthyridin-2-yl)-nonanoic acid;

3(R)-(2-Methyl-pyrimidin-5-yl)-5-oxo-9-(6,7,8,9-tetrahydro-5H-pyrido[2,3-b]azepin-2-yl)-nonanoic acid;

3(S)-(2-Methyl-pyrimidin-5-yl)-5-oxo-9-(6,7,8,9-tetrahydro-5H-pyrido[2,3-b]azepin-2-yl)-nonanoic acid;

3(R)-(2-Methoxy-pyrimidin-5-yl)-5-oxo-9-(6,7,8,9-tetrahydro-5H-pyrido[2,3-b]azepin-2-yl)-nonanoic acid;

3(S)-(2-Methoxy-pyrimidin-5-yl)-5-oxo-9-(6,7,8,9-tetrahydro-5H-pyrido[2,3-b]azepin-2-yl)-nonanoic acid;

3(R)-(2,3-Dihydro-benzofuran-6-yl)-5-oxo-9-(5,6,7,8-tetrahydro-[1,8]naphthyridin-2-yl)-nonanoic acid;

3(S)-(2,3-Dihydro-benzofuran-6-yl)-5-oxo-9-(5,6,7,8-tetrahydro-[1,8]naphthyridin-2-yl)-nonanoic acid;

3(R)-9-(6-Methylamino-pyridin-2-yl)-5-oxo-3-(pyrimidin-5-yl)-nonanoic acid;

3(S)-9-(6-Methylamino-pyridin-2-yl)-5-oxo-3-(pyrimidin-5-yl)-nonanoic acid;

3(R)-(2-Ethoxy-pyrimidin-5-yl)-5-oxo-9-(6,7,8,9-tetrahydro-5H-pyrido[2,3-b]azepin-2-yl)-nonanoic acid;

3(S)-(2-Ethoxy-pyrimidin-5-yl)-5-oxo-9-(6,7,8,9-tetrahydro-5H-pyrido[2,3-b]azepin-2-yl)-nonanoic acid;

3(R)-(Pyrazin-2-yl)-5-oxo-9-(5,6,7,8-tetrahydro-[1,8]naphthyridin-2-yl)-nonanoic acid;

3(S)-(Pyrazin-2-yl)-5-oxo-9-(5,6,7,8-tetrahydro-[1,8]naphthyridin-2-yl)-nonanoic acid;

3(R)-(2-Methyl-pyrazin-5-yl)-5-oxo-9-(5,6,7,8-tetrahydro-[1,8]naphthyridin-2-yl)-nonanoic acid;

3(S)-(2-Methyl-pyrazin-5-yl)-5-oxo-9-(5,6,7,8-tetrahydro-[1,8]naphthyridin-2-yl)-nonanoic acid;

3(R)-(6-Methoxy-pyridazin-3-yl)-5-oxo-9-(5,6,7,8-tetrahydro-[1,8]naphthyridin-2-yl)-nonanoic acid;

3(S)-(6-Methoxy-pyridazin-3-yl)-5-oxo-9-(5,6,7,8-tetrahydro-[1,8]naphthyridin-2-yl)-nonanoic acid;

3(R)-(2-Methylamino-pyrimidin-5-yl)-5-oxo-9-(5,6,7,8-tetrahydro-[1,8]naphthyridin-2-yl)-nonanoic acid;

3(S)-(2-Methylamino-pyrimidin-5-yl)-5-oxo-9-(5,6,7,8-tetrahydro-[1,8]naphthyridin-2-yl)-nonanoic acid;

3(R)-(3,4-Dihydro-2H-1,4-dioxa-5-aza-naphthalen-7-yl)-5-oxo-9-(5,6,7,8-tetrahydro-[1,8]naphthyridin-2-yl)-nonanoic acid;

3(S)-(3,4-Dihydro-2H-1,4-dioxa-5-aza-naphthalen-7-yl)-5-oxo-9-(5,6,7,8-tetrahydro-[1,8]naphthyridin-2-yl)-nonanoic acid;

3(R)-(2-Methyl-pyrimidin-5-yl)-5-oxo-9-(6-methyl-5,6,7,8-tetrahydro-[1,8]naphthyridin-2-yl)-nonanoic acid;

3(S)-(2-Methyl-pyrimidin-5-yl)-5-oxo-9-(6-methyl-5,6,7,8-tetrahydro-[1,8]naphthyridin-2-yl)-nonanoic acid;

3(R)-(Benzofuran-6-yl)-5-oxo-9-(5,6,7,8-tetrahydro-[1,8]naphthyridin-2-yl)-nonanoic acid;

3(S)-(Benzofuran-6-yl)-5-oxo-9-(5,6,7,8-tetrahydro-[1,8]naphthyridin-2-yl)-nonanoic acid;

3(R)-(5-Methoxy-pyridin-3-yl)-5-oxo-9-(5,6,7,8-tetrahydro-[1,8]naphthyridin-2-yl)-nonanoic acid;

3(S)-(5-Methoxy-pyridin-3-yl)-5-oxo-9-(5,6,7,8-tetrahydro-[1,8]naphthyridin-2-yl)-nonanoic acid;

3(R)-(2-Ethoxy-pyrimidin-5-yl)-5-oxo-9-(5,6,7,8-tetrahydro-5H-pyrido[2,3-b]azepin-2-yl)-nonanoic acid;

3(S)-(2-Ethoxy-pyrimidin-5-yl)-5-oxo-9-(5,6,7,8-tetrahydro-5H-pyrido[2,3-b]azepin-2-yl)-nonanoic acid;

3(R)-(2-Methyl-pyrimidin-5-yl)-5-oxo-9-(3-vinyl-5,6,7,8-tetrahydro-[1,8]naphthyridin-2-yl)-nonanoic acid;

3(S)-(2-Methyl-pyrimidin-5-yl)-5-oxo-9-(3-vinyl-5,6,7,8-tetrahydro-[1,8]naphthyridin-2-yl)-nonanoic acid;

3(R)-(2-Methyl-pyrimidin-5-yl)-5-oxo-9-(3-chloro-5,6,7,8-tetrahydro-[1,8]naphthyridin-2-yl)-nonanoic acid;

3(S)-(2-Methyl-pyrimidin-5-yl)-5-oxo-9-(3-chloro-5,6,7,8-tetrahydro-[1,8]naphthyridin-2-yl)-nonanoic acid;

3(R)-(2-Methyl-pyrimidin-5-yl)-5-oxo-9-(3-bromo-5,6,7,8-tetrahydro-[1,8]naphthyridin-2-yl)-nonanoic acid;

3(S)-(2-Methyl-pyrimidin-5-yl)-5-oxo-9-(3-bromo-5,6,7,8-tetrahydro-[1,8]naphthyridin-2-yl)-nonanoic acid;

3(R)-(2-Methoxy-pyrimidin-5-yl)-5-oxo-9-(3-methyl-5,6,7,8-tetrahydro-[1,8]naphthyridin-2-yl)-nonanoic acid;

3(S)-(2-Methoxy-pyrimidin-5-yl)-5-oxo-9-(3-methyl-5,6,7,8-tetrahydro-[1,8]naphthyridin-2-yl)-nonanoic acid;

3(R)-(Quinolin-3-yl)-5-oxo-9-(3-methyl-5,6,7,8-tetrahydro-[1,8]naphthyridin-2-yl)-nonanoic acid;

3(S)-(Quinolin-3-yl)-5-oxo-9-(3-methyl-5,6,7,8-tetrahydro-[1,8]naphthyridin-2-yl)-nonanoic acid;

3(R)-(2-Methyl-pyrimidin-5-yl)-5-oxo-7,7-dimethyl-9-(5,6,7,8-tetrahydro-[1,8]naphthyridin-2-yl)-nonanoic acid;

3(S)-(2-Methyl-pyrimidin-5-yl)-5-oxo-7,7-dimethyl-9-(5,6,7,8-tetrahydro-[1,8]naphthyridin-2-yl)-nonanoic acid;

3(R)-(2-Ethoxy-pyrimidin-5-yl)-5-oxo-9-(3-cyclopropyl-5,6,7,8-tetrahydro-[1,8]naphthyridin-2-yl)-nonanoic acid;

3(S)-(2-Ethoxy-pyrimidin-5-yl)-5-oxo-9-(3-cyclopropyl-5,6,7,8-tetrahydro-[1,8]naphthyridin-2-yl)-nonanoic acid;

3(R)-(6-Methoxy-pyridin-3-yl)-5-oxo-9-(3-cyclopropyl-5,6,7,8-tetrahydro-[1,8]naphthyridin-2-yl)-nonanoic acid;

3(S)-(6-Methoxy-pyridin-3-yl)-5-oxo-9-(3-cyclopropyl-5,6,7,8-tetrahydro-[1,8]naphthyridin-2-yl)-nonanoic acid;

3(R)-(2-Dimethylamino-pyrimidin-5-yl)-5-oxo-9-(5,6,7,8-tetrahydro-[1,8]naphthyridin-2-yl)-nonanoic acid; and 3(S)-(2-Dimethylamino-pyrimidin-5-yl)-5-oxo-9-(5,6,7,8-tetrahydro-[1,8]naphthyridin-2-yl)-nonanoic acid;

or a pharmaceutically acceptable salt thereof.

Even further illustrative of the compounds of the present invention are the following:

3(S)-(2-Methyl-pyrimidin-5-yl)-5-oxo-9-(5,6,7,8-tetrahydro-[1,8]-naphthyridin-2-yl)-nonanoic acid;

3(S)-(2-Methyl-pyrimidin-5-yl)-5-oxo-9-(3-cyclopropyl-5,6,7,8-tetrahydro[1,8]-naphthyridin-2-yl)-nonanoic acid;

3(S)-(2-Ethoxy-pyrimidin-5-yl)-5-oxo-9-(5,6,7,8-tetrahydro[1,8]naphthyridin-2-yl)-nonanoic acid;

3(S)-(2-Methoxy-pyrimidin-5-yl)-5-oxo-9-(5,6,7,8-tetrahydro [1,8]naphthyridin-2-yl)-nonanoic acid;

3(S)-(2-Methoxy-pyrimidin-5-yl)-5-oxo-9-(6,7,8,9-tetrahydro-5H-pyrido[2,3-b]azepin-2-yl)-nonanoic acid; and 3(S)-(2-Methoxy-pyrimidin-5-yl)-5-oxo-9-(6,7,8,9-tetrahydro-5H-pyrido[2,3-b]azepin-2-yl)-nonanoic acid; and 3(S)-(2,3-Dihydro-benzofuran-6-yl)-5-oxo-9-(5,6,7,8-tetrahydro-[1,8]naphthyridin-2-yl)-nonanoic acid;

or a pharmaceutically acceptable salt thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by HPLC using a chiral stationary phase. Alternatively, any enantiomer of a compound of the present invention may be obtained by stereospecific synthesis using optically pure starting materials or reagents of known configuration.

Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the $\alpha v \beta 3$ receptor or the $\alpha v \beta 5$ receptor, or a compound which binds to and antagonizes a combination of these receptors (for example, a dual $\alpha v \beta 3 / \alpha v \beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The termr "aryl," as used herein, refers to a monocyclic or bicyclic system comprising at least one aromatic ring, wherein the monocylic or bicyclic system contains 0, 1, 2, 3, or 4 heteroatoms chosen from N, O, or S, and wherein the monocylic or bicylic system is either unsubstituted or substituted with one or more groups independently selected from halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylarnino, $C_{1-6}$ alkyamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo, and $C_{1-5}$ alkylcarbonyloxy. Examples of aryl include, but are not limnited to, phenyl, naphthyl, pyridyl, pyrrolyl, pyrazolyl, pyrazinyl, pyrimidinyl, imidazolyl, benzimidazolyl, benzthiazolyl, benzoxazolyl, quinolyl, isoquinolyl, quinazolyl, quinoxalyl, indolyl, thienyl, furyl, benzofuryl, dihydrobenzofuryl, benzothienyl, benzo(1,3)dioxolanyl, benzo(1,4)dioxanyl, oxazolyl, isoxazolyl, thiazolyl, isothiazolyl, and tetrazolyl, which are either unsubstituted or substituted with one or more groups independently selected from halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo, and $C_{1-5}$ alkylcarbonyloxy. Preferably, the aryl group is unsubstituted, mono-, di-, or tri-substituted with one to three of the above-named substituents; more preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{1-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^2$ substituents, when on the same carbon atom, can be taken together with the carbon atom to which they are attached to form a carbonyl group.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

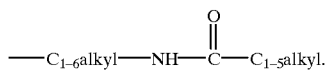

In choosing compounds of the present invention, one of ordinary skill in the art will recognize that the various substituents, i.e. X, $R^1$, $R^2$, $R^3$, $R^4$, $R^5$, $R^6$, $R^7$, and $R^8$, are to be chosen in conformity with well-known principles of chemical structure connectivity.

Representative compounds of the present invention typically display submicromolar affinity for the αv integrin receptors, particularly the αvβ3 and αvβ5 receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Illustrating the invention is the method wherein the αv integrin receptor antagonizing effect is an αvβ3 antagonizing effect. More particularly, the αvβ3 antagonizing effect is selected from inhibition of: bone resorption, restenosis, angiogenesis, diabetic retinopathy, macular degeneration, inflammation, inflammatory arthritis, viral disease, cancer, and metastatic tumor growth. In one embodiment of the method, the αvβ3 antagonizing effect is the inhibition of bone resorption.

Another example of the invention is the method wherein the αv integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, cancer, and metastatic tumor growth.

Further illustrating the invention is the method wherein the aXv integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammation, viral disease, cancer, and metastatic tumor growth.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an αv integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, inflammatory arthritis, viral disease, cancer, tumor growth, and metastasis. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of viral disease, and inhibition of cancer or metastatic tumor growth. Most preferably, the αvβ3 antagonizing effect is inhibition of bone resorption. Alternatively, the integrin antagonizing effect is an αvβ5 antagonizing effect or a dual αvβ3/αvβ5 antagonizing effect. Examples of αvβ5 antagonizing effects are inhibition of restenosis, atherosclerosis, angiogenesis, diabetic retinopathy, macular degeneration, inflammation, viral disease, and metastatic tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, tumor growth, cancer, restenosis, atherosclerosis, diabetic retinopathy, macular degeneration, inflammation, inflammatory arthritis, viral disease, and/or angiogenesis.

Also exemplifying the invention are compositions further comprising an active ingredient selected from the group consisting of:

a) an organic bisphosphonate or a pharmaceutically acceptable salt or ester thereof,
b) an estrogen receptor modulator,
c) an androgen receptor modulator,
d) a cytotoxic/antiproliferative agent,
e) a matrix metalloproteinase inhibitor,
f) an inhibitor of epidermal-derived, fibroblast-derived, or platelet-derived growth factors,
g) an inhibitor of VEGF,
h) an antibody to a growth factor or to a growth factor receptor,
i) an inhibitor of Flk-1/KDR, Flt-1, Tck/Tie-2, or Tie-1,
j) a cathepsin K inhibitor,
k) a growth hormone secretagogue,
l) an inhibitor of osteoclast proton ATPase,
m) an inhibitor of urokinase plasminogen activator (u-PA),
n) a tumor-specific antibody-interleukin-2 fusion protein,
o) an inhibitor of HMG-CoA reductase, and
p) a prenylation inhibitor, such as a farnesyl transferase inhibitor or a geranylgeranyl transferase inhibitor or a dual farnesyl/geranylgeranyl transferase inhibitor;
and mixtures thereof.

(See, B. Millauer et al., "Dominant-Negative Inhibition of Flk-1 Suppresses the Growth of Many Tumor Types in Vivo", *Cancer Research*, 56, 1615–1620 (1996), which is incorporated by reference herein in its entirety).

Preferably, the active ingredient is selected from the group consisting of:

a) an organic bisphosphonate or a pharmaceutically acceptable salt or ester thereof,
b) an estrogen receptor modulator,
c) an androgen receptor modulator,
d) an inhibitor of osteoclast proton ATPase,
e) an inhibitor of HMG-CoA reductase, and
f) a cathepsin K inhibitor;
and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see *The Wall Street Journal*, Friday, Dec. 3, 1999, page B 1). Therefore, the statins hold promise for the treatment of bone resorption. Nonlimiting examples of statins are lovastatin, simvastatin, atorvastatin, and pravastatin.

Evidence for a crucial role of the urokinase-urokinase receptor (u-PA-u-PAR) in angiogenesis, tumor invasion, inflammation, and matrix remodeling during wound healing and development has been presented [see Y. Koshelnick et al., "Mechanisms of signaling through Urokinase Receptor and the Cellular Response," *Thrombosis and Haemostasis* 82: 305–311 (1999) and F. Blasi, "Proteolysis, Cell Adhesion, Chemotaxis, and Invasiveness Are Regulated by the u-PA-u-PAR-PAI-I System," *Thrombosis and Haemostasis* 82: 298–304 (1999)]. Thus, specific antagonists of the binding of u-PA to u-PAR have been found to inhibit cell-surface plasminogen activation, tumor growth, and angiogenesis in both in vitro and in vivo models.

H. N. Lode and coworkers in *PNAS USA* 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," *DDT*, 4: 163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.*, 69: 177–184 (1999) and K. A. Hansen and S. P. T. Tho, "Androgens and Bone Health," *Seminars in Reproductive Endocrinology*," 16: 129–134 (1998). Thus, androgen receptor modulators may have utility in the treatment and prevention of bone loss in women.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology*, 140: 5060–5065 (1999) point to a local mechanism on bone marrow cells as well as a systemic one on glucose metabolism. Nonlimiting examples of PPARγ activators include troglitazone, pioglitazone, rosiglitazone, and BRL 49653.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a growth hormone secretagogue, a cathepsin K inhibitor, an HMG-CoA reductase inhibitor, a PPARγ activator, or an inhibitor of the osteoclast proton ATPase.

Additional illustrations of the invention are methods of treating tumor growth or metastasis in a manmmal in need thereof, comprising administering to the mammal a therapeutically effective amount of a compound described above and one or more agents known to be cytotoxiclantiproliferative. Also, the compounds of the present invention can be administered in combination with radiation therapy for treating cancer and metastatic tumor growth.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamnide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the Schemes and Examples below, various reagent symbols and abbreviations have the following meanings:
AcOH: Acetic acid
BH$_3$.DMS: Borane.dimethylsulfide
BOC(Boc): t-Butyloxycarbonyl
BOP: Benzotriazol-1-yloxytris(dimethylamino)-phosphonium hexafluorophosphate
CBZ(Cbz): Carbobenzyloxy or benzyloxycarbonyl
CDI: Carbonyldiimidazole
CH$_2$Cl$_2$: Methylene chloride
CH$_3$CN: Acetonitrile
CHCl$_3$: Chloroform
DEAD: Diethyl azodicarboxylate
DIAD: Diisopropyl azodicarboxylate
DIBAH or
DIBAL-H: Diisobutylaluminum hydride
DIPEA: Diisopropylethylamine
DMAP: 4-Dimethylaminopyridine
DME: 1,2-Dimethoxyethane
DMF: N,N-Dimethylformamide
DMSO: Dimethylsulfoxide
DPFN: 3,5-Dimethyl-1-pyrazolylformrnamidine nitrate
EDC: 1-(3-Dimethylaminopropyl)-3-ethylcarbodiimide.HCl
EtOAc: Ethyl acetate
EtOH: Ethanol
HOAc: Acetic acid
HOAT: 1-Hydroxy-7-azabenzotriazole
HOBT: 1-Hydroxybenzotriazole
HPLC: High-performance liquid chromatography
IBCF: Isobutylchloroformate
LDA: Lithium diisopropylamide
MeOH: Methanol
MNNG: 1,1-methyl-3-nitro-1-nitrosoguanidine
NEt$_3$: Triethylamine
NMM: N-methylmorpholine
PCA.HCl: Pyrazole carboxamidine hydrochloride
Pd/C: Palladium on activated carbon catalyst
Ph: Phenyl
pTSA p-Toluenesulfonic acid
TEA: Triethylamine
TFA: Trifluoroacetic acid
THF: Tetrahydrofuran
TLC: Thin Layer Chromatography
TMEDA: N,N,N',N'-Tetramethylethylenediamine
TMS: Trimethylsilyl The novel compounds of the present invention can be prepared according to the procedures of the following reaction Schemes and Examples, or modifications thereof, using readily available starting materials, reagents, and, where appropriate, conventional synthetic procedures. In these procedures, it is also possible to make use of variants which are themselves known to those of ordinary skill in the organic synthetic arts, but are not mentioned in greater detail. For example, replacing 5-formyl-2-methyl-pyrimidine (1-6a) in Scheme 1 with the appropriately substituted aryl-CHO affords the corresponding compound wherein the aryl group R$^7$ is other than 2-methyl-pyrimidin-5-yl. Resolution of the racemic mixture of (R) and (S) keto diesters 1-8 can be accomplished by HPLC chromatography on a chiral solid support, such as Chiralcel AD or Chiralcel OD columns. In this fashion are isolated the individual (E)- and (S)-enantiomers, such as 1-8a and 1-8b, substantially free of the other enantiomer. The final resolved 3(R) and 3(S) products, such as 1-11a and 1-11b, are derived from the keto diester precursors in a three-step sequence of hydrolysis, decarboxylation, and hydrolysis.

The C-5 and C-7 alcohol derivatives of the compounds of the present invention can be prepared by reduction of the corresponding 5- and 7-keto intermediates, respectively, whose preparation is described in the Schemes and Examples below. The reduction can be effected with a metal hydride, such as sodium or lithium borohydride, in a suitable solvent, such as methylene chloride, tetrahydrofuran, ethanol, or methanol. Reduction of the keto group to generate the alcohol derivatives may also carried out in an enantio- or diastereo-selective fashion using chiral reducing agents, such as (R)- or (S)-2-methyl-CBS-oxazaborolidine, in a suitable solvent, such as toluene, hexane, diethyl ether, methylene chloride, or tetrahydrofuran.

The following Examples are illustrative of the more preferred compounds of the present invention. They are not, however, to be construed as forming the only genus that is considered as the invention. The Examples further illustrate details for preparation of the compounds of the present invention. Those skilled in the art will readily understand that known variations of the conditions and processes of the following preparative procedures can be used to prepare these compounds. Unless stated otherwise, all operations were carried out at room or ambient temperature, and all temperatures are degrees Celsius.

SCHEME 1

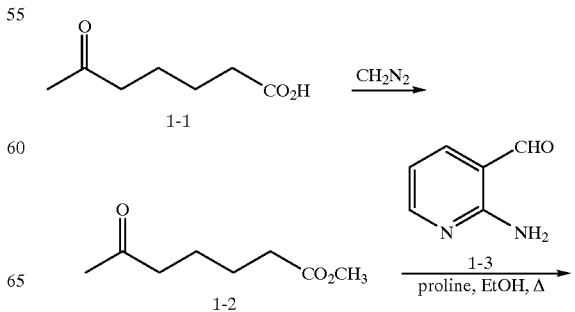

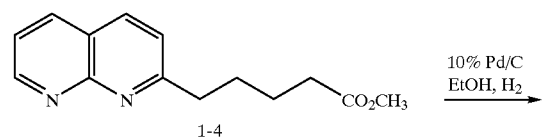

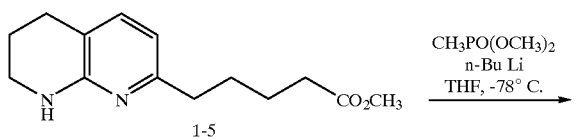

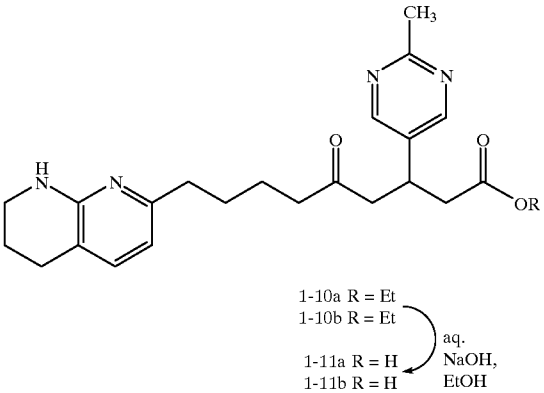

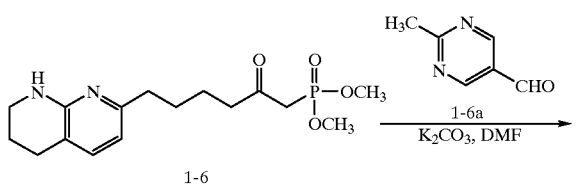

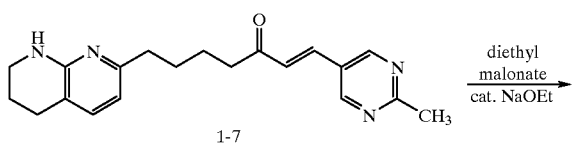

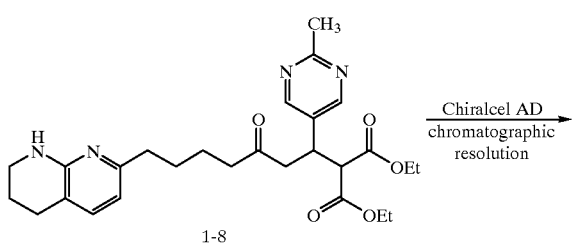

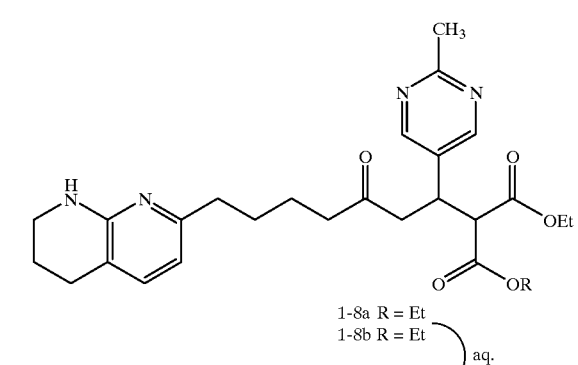

EXAMPLE 1

3(S or R)-(2-Methyl-pyrimidin-5-yl)-5-oxo-9-(5,6,7,8-tetrahydro-[1,8]naphthyridin-2-yl)-nonanoic Acid (1-11a)

Step A: 6-Oxo-heptanoic Acid Methyl Ester (1-2)

To a rapidly stirred mixture of diethyl ether (175 ml) and 40% KOH (52 ml) at 0° C. was added MNNG (15.4 g, 105 mmol). The mixture was stirred for 10 minutes. The ethereal layer was transferred to a solution of 6-oxo-heptanoic acid 1-1 (5.0 g, 34.68 mmol) and $CH_2Cl_2$ at 0° C. The solution was purged with argon for 30 minutes and then concentrated. Flash chromatography (silica, 30% to 50% EtOAc/hexanes) gave ester 1-2 as a clear oil.

TLC $R_f$=0.88 (silica, EtOAc).

$^1$H NMR (300 MHz, $CDCl_3$) δ 3.67 (s, 3H), 2.46 (m,2H), 2.33 (m, 2H), 2.14 (s, 3H), 1.62 (m, 4H).

Step B: 5-[1,8]-Naphthyridin-2-yl-pentanoic Acid Methyl Ester (1-4)

A mixture of 1-2 (1.4 g, 9.04 mmol), 1-3, 2-amino-3-formylpyridine (552 mg, 4.52 mmol) (for preparation, see: J. Org. Chem., 1983, 48, 3401), and proline (260 mg, 2.26 mmol) in absolute ethanol (23 mL) was heated at reflux for 18 h. Following evaporative removal of the solvent, the residue was chromatog,raphed (silica gel, 80% ethyl acetate/hexane, then ethyl acetate) to give ester 1-4 as a white solid.

TLC $R_f$=0.38 (silica, EtOAc). $^1$H NMR (300 MHz, $CDCl_{13}$) δ 8 9.08 (m, 1H), 8.16 (d, J=8.0 Hz, 1H), 8.10 (d, J=8.3 Hz, 1H), 7.45 (m, 1H), 7.39 (d, J=8.3 Hz, 1H), 3.66 (s, 3H), 3.08 (t, J=7.6 Hz,2H), 2.39 (t, J=7.6 Hz, 2H), 1.94 (m,2H), 1.78 (m, 2H).

Step C: 5-(5,6,7,8-Tetrahydro-[1,8]naphthyridin-2-yl)-pentanoic Acid Methyl Ester (1-5)

A mixture of 1-4 (630 mg, 2.58 mmol) and 10% Pd/carbon (95 mg) in EtOH (25 mL) was stirred under a balloon of hydrogen for 72 h. Following filtration and evaporative removal of the solvent, the residue was chromatographed (silica gel, 70% ethyl acetate/hexanes) to give 1-5 as a colorless oil.

TLC $R_f$=0.58 (silica, ethyl acetate). $^1$H NMR (300 MHz, $CDCl_3$) δ 7.05 (d, J=7.3 Hz, 1H), 6.34 (d, J=7.3 Hz, 1H), 4.72 (s, 1H), 3.66 (s, 3H), 3.40 (m, 2H), 2.69 (t, J=6.3 Hz, 2H), 2.53 (m, 2H), 2.33 (m, 2H), 1.90 (m, 2H), 1.66 (m, 4H).

Step D: 2-Oxo-6-(5,6,7,8-tetrahydro-[1,8]-naphthyridin-2-yl)-hexyl-phosphonic Acid Dimethyl Ester (1-6)

A solution of dimethyl methylphosphonate (13.20 g, 106.5 mmol) in anhydrous THF (165 mL) was cooled to −78° and treated dropwise with 2.5 M n-BuLi (42.3 mL). After stirring at −78° for 45 min, a solution of ester 1-5 (6.6 g, 26.6 mmol) in THF (35 mL) was added dropwise and the resulting solution stirred for 30 min at −78°, quenched with sat. NH₄Cl (100 mL), then extracted with ethyl acetate (3×150 mL). The combined organic extracts were dried (MgSO₄), filtered, and concentrated to afford a yellow oil. Chromatography on silica gel (5% MeOH/CH₂Cl₂) afforded 1-6 as a yellow oil.

$R_f$(silica, 5% MeOH/CH$_2$Cl$_2$)=0.20. $^1$H NMR (300 MHz, CDCl$_3$) δ 7.05 (d, J=7.3 Hz, 1H), 6.34 (d, J=7.32 Hz, 1H), 4.80 (br, s, 1H), 3.81 (s, 3H), 3.75 (s, 3H), 3.4 (m, 2H), 3.08 (d, J=22.7 Hz), 2.7–2.5 (m, 6H), 1.91 (m, 2H), 1.68 (m, 4H).

Step E: 1-(2-Methyl-pyrimidin-5-yl)-7-(5,6,7,8-tetrahydro-[1,8]naphthyridin-2-yl)-hept-1-en-3-one (1-7)

To a solution of 1-6 (5.5 g, 16.2 mmol), 5-formyl-2-methylpyrimidine (1-6a, 1.8 g, 14.7 mmol; for preparation, see *J. Heterocyclic Chem.*, 28, 1281 (1991)) in 40 mL DMF was added K$_2$CO$_3$(4.07 g, 32 mmol). The mixture was stirred at ambient temperature for 15 hr, and concentrated to a paste. The residue was diluted with water, extracted with ethyl acetate, and dried over magnesium sulfate. Following concentration, the residue was chromatographed on silica gel (70 chloroform/25 ethyl acetate/5 methanol) to give 1-7 as a white solid.

$R_f$=0.20 (silica, 70 chloroform/20 ethyl acetate/10 methanol). $^1$H NMR (400 MHz, CDCl$_3$) δ 8.80 (s, 2H), 7.44 (d, 1H, J=16 Hz), 7.05 (d, 1H, J=7 Hz), 6.81 (d, 1H, J=16 Hz), 6.35 (d, 1H, J=7 Hz), 4.72 (br s, 1H), 3.39 (m, 2H), 2.69 (s, 3H), 2.64 (m, 4H), 2.58 (m, 2H), 1.91 (m, 2H), 1.74 (m, 4H).

Step F: 2-[1(S or R)-(2-Methyl-pyrimidin-5-yl)-3-oxo-7-(5,6,7,8-tetrahydro-[1,8]naphthyridin-2-yl)-heptyl]-malonic Acid Diethyl Ester (1-8a)

To a solution of 1-7 (1.0 g, 2.97 mmol) and diethyl malonate (0.717 ml, 4.5 mmol) in ethanol (20 mL) and THF (20 mL) was added sodium ethoxide (0.1 mL of a 30% w/w solution in ethanol). After 4 hr, the mixture (1-8) was concentrated, and the residue purified on a 5×50 cm Chiralcel AD column (flow=80 mL/min, A:B=30:70) (A=0.1% diethylamine/hexane, B=2-propanol). Product 1-8a eluted at 15 minutes; its enantiomer, 1-8b, eluted at 26 minutes.

$^1$H NMR (400 MHz, CDCl$_3$) δ 8. 53 (s, 2H), 7.02 (d, 1H, J=7 Hz), 6.28 (d, 1H, J=7 Hz), 4.07 (br s, 1H), 4.18 (m, 2H), 4.02 (m, 2H), 3.92 (m, 1H), 3.72 (m, 2H), 3.39 (m, 2H), 2.94 (m, 2H), 2.64 (s, 3H), 2.42 (m, 2H), 2.33 (m, 2H), 1.89 (m, 2H), 1.60 (m, 4H), 1.26 (m, 4H), 1.19 (t, 3H, J=3 Hz).

Step G: 3(S or R)-(2-Methyl-pyrimidin-5-yl)-5-oxo-9-(5,6,7,8-tetrahydro-[1,8]naphthyridin-2-yl)-nonanoic Acid Ethyl Ester (1-10a)

To a solution of 1-8a (0.530 g, 1.07 mmol) in ethanol (5 mL) was added NaOH (1.12 mL of 1N solution in water, 1.12 mmol). After stirring at 40° C. for 30 minutes, the mixture was treated with HCl (1.12 mL of 1N solution in water, 1.12 mmol) and concentrated. The residue was suspended in toluene (20 mL) and heated at reflux. After 1 h, evaporation of the solvents gave 1-10a as a yellow oil.

$R_f$=0.32 (silica, 70 chloroform/20 ethyl acetate/10 methanol). $^1$H NMR (400 MHz, CDCl$_3$) δ 8.54 (s, 2H), 7.04 (d, 1H, J=7 Hz), 6.31 (d, 1H, J=7 Hz), 4.86 (br s, 1H), 4.04 (q, 2H, J=3 Hz), 3.63 (m, 1H), 3.40 (m, 2H), 2.94–2.48 (m, 9H), 2.37 (m, 4H), 1.89 (m, 2H), 1.57 (m, 4H), 1.19 (t, 3H, J=3 Hz).

Step H: 3(S or R)-(2-Methyl-pyrimidin-5-yl)-5-oxo-9-(5,6,7,8-tetrahydro-[1,8]naphthyridin-2-yl)-nonanoic Acid (1-11a)

To a solution of 1-10a (0.15 g, 0.353 mmol) in ethanol (1 mL) was added NaOH (0.39 mL of 1N solution in water, 0.39 mmol). After 30 minutes, the mixture was concentrated, and the residue chromatographed on silica gel (20:10:1:1 to 10:10:1:1 ethyl acetate/ethanol/NH₄OH/water) to give 1-11a as a white solid.

$R_f$=0.21 (silica, 10:10:1:1 ethyl acetate/ethanol/NH₄OH/water). $^1$H NMR (400 MHz, CH$_3$OD) δ 8.62 (s, 2H), 7.43 (d, 1H, J=7 Hz), 3.68 (m, 1H), 3.43 (m, 2H), 3.02 (m, 2H), 2.80 (m, 3H), 2.59 (m, 10H), 1.91 (m, 2H), 1.60 (m, 3H).

EXAMPLE 2

3(R or S)-(2-Methyl-pyrimidin-5-yl)-5-oxo-9-(5,6,7,8-tetrahydro-[1,8]naphthyridin-2-5-yl)-nonanoic Acid (1-11b)

Enantiomer 1-11b was obtained from 1-8b utilizing the same methods described for the preparation of 1-11a above. Its 400 MHz NMR spectrum in CD$_3$OD was identical to that of its enantiomer 1-11a. High resolution mass spectrum: calculated: 397.2234; found: 397.2232.

SCHEME 2

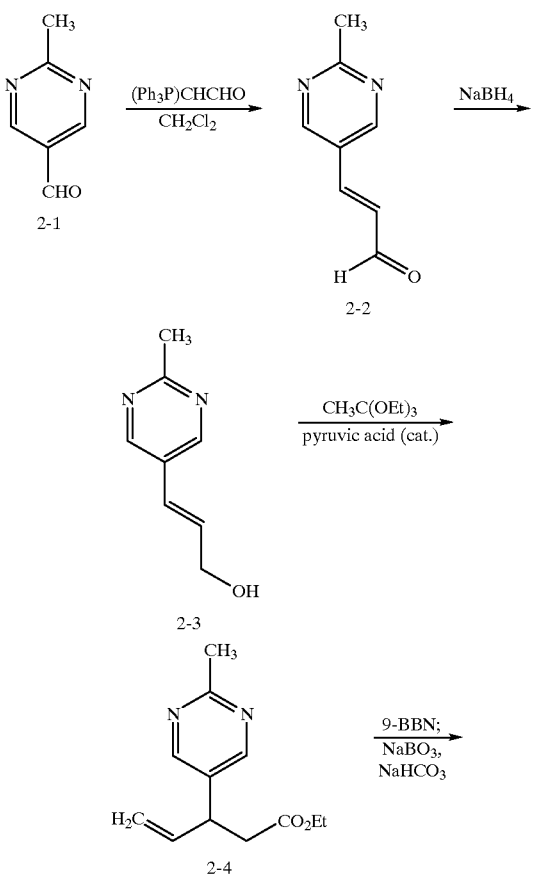

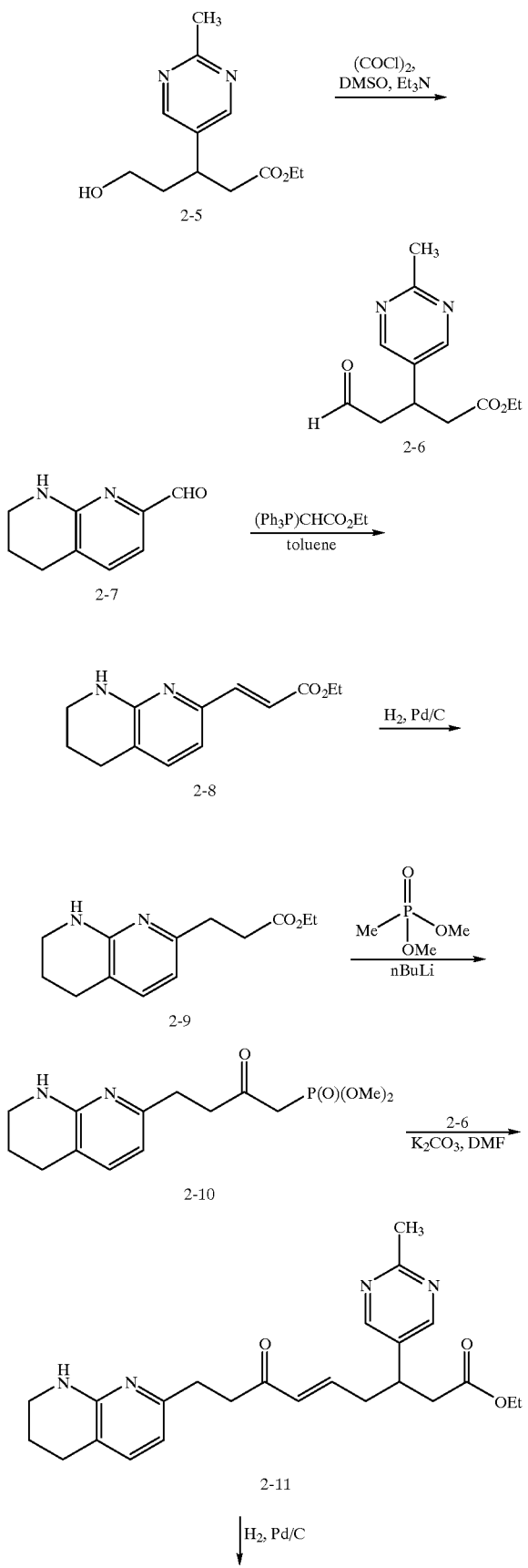

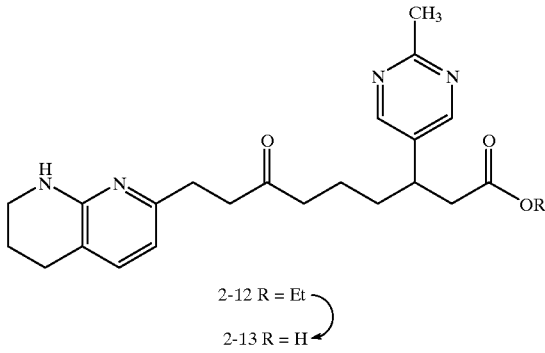

2-12 R = Et
2-13 R = H

EXAMPLE 3

3-(2-Methyl-pyrimidin-5-yl)-7-oxo-9-(5,6,7,8-tetrahydro-[1,8]naphthyridin-2-yl)-nonanoic Acid (2-13)

Step A: 3-(2-Methyl-pyrimidin-5-yl)-propenal (2-2)

To a solution of 4-formyl-2-methylpyrimidine [2-1, 2 g, 16.4 mmol; for preparation, see Smith, S. Q. et al, *J. Heterocyclic Chem.* 28: 1281 (1991)] in methylene chloride (15 mL) was added (formylmethylene)triphenylphosphorane (5.98g, 19.6 mmol). The solution was heated at reflux for 4 h, cooled to room temperature, and solvents evaporated. The residue was chromatographed on silica gel (30% EtOAc/chloroform to 50 EtOAc/50 chloroform/5 methanol) to give the aldehyde 2-2 as a yellow solid.

TLC Rf=0.39 (70 chloroform/25 EtOAc/5 MeOH). $^1$H NMR (400 MHz, CDCl$_3$) δ 9.74 (d, 1H, J=7 Hz), 8.83 (s, 2H), 7.41 (d, 1H, J=7 Hz), 6.81 (dd, 1H, S=6 Hz, 15 Hz), 2.77 (s, 3H).

Step B: 3-(2-Methyl-pyrimidin-5-yl)-prop-2-en-1-ol (2-3)

To a suspension of 2-2 (0.5 g, 3.7 mmol) in MeOH (5 mL) and THF (15 mL) at −78° C. was added sodium borohydride (0.042 g, 1.11 mmol) in one portion. After 5 minutes, the cooling bath was removed, and the mixture allowed to warm and stir for 10 minutes. Concentrated HCl (0.3 mL) was added dropwise, and the volume of the mixture reduced to 2 mL by evaporation. Following the addition of sat. NaHCO$_3$ (10 mL), the mixture was extracted with chloroform, the organics dried over MgSO$_4$, and the solvents evaporated to give alcohol 2-3 as a white solid.

TLC Rf=0.16 (70 chloroform/25 EtOAc/5 MeOH). $^1$H NMR (400 MHz, CDCl$_3$) δ 8.64 (s, 2H), 6.48 (m, 2H), 4.38 (d, 2H, J=4 Hz), 2.73 (s, 3H).

Step C: 3-(2-Methyl-pyrimidin-5-yl)-pent-4-enoic Acid Ethyl Ester (2-4)

A solution of 2-3 (0.49 g, 3.6 mmol), propionic acid (10 μL) and trimethylorthoformate (5 mL) was heated to reflux for 18 hours. Evaporative removal of the solvent and one evaporation from toluene gave 2-4 as a brown oil. p TLC R$_f$=0.725 (silica, 70/25/5 CHCl$_3$/EtOAc/MeOH) $^1$H NMR (400 MHz, CDCl$_3$) δ 8.50 (s, 2H), 5.98 (m, 1H), 5.16 (m, 2H), 4.10 (m, 2H), 3.86 (q, J=7 Hz, 1H), 2.7 (m, 5H), 1.29 (m, 3H).

Step D: 5-Hydroxy-3-(2-methyl-pyrimidin-5-yl)-pentanoic Acid Ethyl Ester (2-5)

To a stirred solution of 2-4 (422 mg, 1.92 mmol) in TBF was added 5.75 mL of 9-BBN (0.5 M/THF). After 18 hours, a slurry of NaBO$_3$ (2.35 g) and NaHCO$_3$ (2.42 g) in H$_2$O (10 mL) was added and the mixture stirred vigorously for 1 hour. The mixture was extracted with CHCl$_3$, washed with brine, and dried over MgSO$_4$. Following evaporative removal of the solvent, the residue was chromatographed (silica gel, 3% EtOH/EtOAc) to give 2-5 as a clear oil.

TLC R$_f$=0.42 (silica, 10% EtOH/EtOAc). $^1$H NMR (400 MHz, CDCl$_3$) δ 8.52 (s, 2H), 4.07 (m, 2H), 3.62 (m, 1H), 3.50 (m, 1H), 3.35 (m, 1H), 2.65 (m, 5H), 2.01 (m, 1H), 1.88 (m, 1H), 1.17 (t, J=7 Hz, 3H).

Step E: 3-(2-Methyl-pyrimidin-5-yl)-5-oxo-pentanoic Acid Ethyl Ester (2-6)

To a solution of oxalyl chloride (73 μL, 0.84 mmol) in CH$_2$Cl$_2$ at −78° C. was added DMSO (80 μL, 1.0 mmol) dropwise. After gas evolution ceased, 2-5 (100 mg, 0.42 mmol) in CH$_2$Cl$_2$ was added. After 30 minutes, the cooling bath was removed and NEt3 (290 μL, 2.1 mmol) was added. After 20 minutes, the reaction mixture was diluted with CH$_2$Cl$_2$ and washed sat. NaHCO$_3$ and brine, dried (MgSO$_4$), and concentrated to give 2-6 as a yellow oil.

TLC R$_f$=0.24 (silica, 70/20/10 CHCl$_3$/EtOAc/MeOH). $^1$H NMR (400 MHz, CDCl$_3$) δ 9.71 (s, 1H), 8.55 (s, 2H), 4.06 (m, 2H), 3.71 (m, 1H), 2.95 (m, 2H), 2.88 to 2.50 (m, 5H), 1.18 (t, J=7 Hz, 3H).

Step F: 3-(5,6,7,8-Tetrahydro-[1,8]naphthyridin-2-yl)-acrylic Acid Ethyl Ester (2-8)

A solution of 5,6,7,8-tetrahydro-[1,8]naphthyridine-2-carbaldehyde (2-7, 2 g, 12.34 mmol) and (carbethoxymethylene)triphenylphosphorane (4.3 g, 12.34 mmol) in toluene (60 mL) was heated to reflux for 4 hours and stirred at ambient temperature for 12 hours. Following evaporative removal of the solvent, the residue was chromatographed (silica gel, 50% EtOAc/hexanes) to give 2-8 as a yellow solid.

TLC R$_f$=0.75 (silica, 70% EtOAc/hexanes). $^1$H NMR (400 MHz, CDCl$_3$) δ 7.46 (d, J=15 Hz, 1H), 7.14 (d, J=8 Hz, 1H), 6.75 (d, J=15 Hz, 1H), 6.62 (d, J=8 Hz, 1H), 4.97 (s, 1H), 4.24 (q, J=7 Hz, 2H), 3.42 (m, 2H), 2.74 (t, J=7 Hz, 2H), 1.91 (m, 2H), 1.30 (m, 3H).

Step G: 3-(5,6,7,8-Tetrahydro-[1,8]naphthyridin-2-yl)-propionic Acid Ethyl Ester (2-9)

A mixture of 2-8 (1.4 g, 6.03 mmol) and 10% Pd/carbon (1 g) in EtOH (30 mL) was stirred under a balloon of hydrogen for 18 h. Filtration and evaporative removal of the solvent gave 2-9 as a white solid.

TLC R$_f$=0.39 (silica, 70% EtOAc/hexanes). $^1$H NMR (400 MHz, CDCl$_3$) δ 7.07 (d, J=7 Hz, 1H), 6.37 (d, J=7 Hz, 1H), 4.12 (m, 2H), 3.40 (m, 2H), 2.87 (m, 2H), 2.67 (m, 4H), 1.91 (t, J=6 Hz, 2H), 1.24 (m, 3H).

Step H: [2-Oxo-4-(5,6,7,8-tetrahydro-[1,8]naphthyridin-2-yl)-butyl]-phosphonic Acid Dimethyl Ester (2-10)

To a stirred solution of dimethyl methylphosphonate (1.9 mL, 17.08 mmol) in THF (20 mL) at −78° C. was added nBuLi (10.94 mL, 17.5 mmol). After 30 minutes, 2-9 (1 g, 4.27 mmol) in THF (5 mL) was added. After 1 hour, the reaction was quenched with saturated NH4Cl (10 mL) and warmed to ambient temperature. The mixture was diluted with ethyl acetate, washed with sat. NaHCO$_3$, brine, and dried over MgSO$_4$. Following evaporative removal of the solvent, the residue was chromatographed (silica gel, 70/25/5 CHCl$_3$/EtOAc/MeOH) to give 2-10 as a yellow oil.

TLC R$_f$=0.33 (silica, 70/20/10 CHCl$_3$/EtOAc/MeOH). $^1$H NMR (400 MHz, CDCl$_3$) δ 7.03 (d, J=7 Hz, 1H), 6.34 (d, J=7 Hz, 1H), 4.93 (s, 1H), 3.77 (d, J=12, 6H), 3.38 (m, 2H), 3.15 (d, J=23, 2H), 2.96 (m, 2H), 2.86 (m, 2H), 2.67 (t, J=6 Hz, 2H), 1.88 (m, 2H).

Step I: 3-(2-Methyl-pyrimidin-5-yl)-7-oxo-9-(5,6,7,8-tetrahydro-[1,8]naphthyridin-2-yl)-non-5-enoic Acid Ethyl Ester (2-11)

To a mixture of 2-10 (100 mg, 0.42 mmol) and 2-6 (160 mg, 0.54 mmol) in DMF (3 mL) was added K$_2$CO$_3$ (87 mg, 0.63 mmol) followed by heating to 50° C. for 18 hours. Following evaporative removal of the solvent, the residue was chromatographed (silica gel, 70:25:5 CHCl$_3$/EtOAc/MeOH) to give 2-11 as a clear oil.

TLC Rf=0.38 (70:20:10 CHCl$_3$/EtOAc/MeOH). $^1$H NMR (400 MHz, CDCl$_3$) δ 8.49 (s, 1H), 7.03 (d, J=7 Hz, 2H), 6.65 (m, 1H), 6.43 (d, J=7 Hz, 1H), 6.07 (d, J=15 Hz, 1H), 4.85 (m, 1H), 4.05 (m, 2H), 3.80 (m, 1H), 3.41 (m, 3H), 2.90–2.54 (m, 13H), 1.88 (m, 4H), 1.18 (m, 3H).

Step J: 3-(2-Methyl-pyrimidin-5-yl)-7-oxo-9-(5,6,7,8-tetrahydro-[1,8]naphthyridin-2-yl)-nonanoic Acid Ethyl Ester (2-12)

A mixture of 2-11 (95 mg, 0.22 mmol) and 10% Pd/carbon (50 mg) in EtOH (3 mL) was stirred under a balloon of hydrogen for 2 h. Following filtration, evaporative removal of the solvent gave 2-12 as a clear oil.

TLC Rf=0.40 (70:20:10 CHCl$_3$/EtOAc/MeOH). $^1$H NMR (400 MHz, CDCl$_3$) δ 8.47 (s, 2H), 7.04 (d, J=7 Hz, 1H), 6.33 (d, J=7 Hz, 1H), 4.03 (m, 2H), 3.78 (m, 1H), 3.38 (m, 2H), 3.01 (m, 1H) 2.74 (m, 10H), 2.54 (m, 1H), 2.40 (t, J=7 Hz, 2H), 1.89 (m, 2H), 1.57 (m, 4H), 1.15 (t, J=7 Hz, 3H).

Step K: 3-(2-Methyl-pyrimidin-5-yl)-7-oxo-9-(5,6,7,8-tetrahydro-[1,8]naphthyridin-2-yl)-nonanoic Acid (2-13)

To a solution of 2-12 (77 mg, 0.18 mmol) in EtOH (2 mL) was added 1N NaOH (272 μl, 0.27 mmol). After stirring for 2 h, the solvents were evaporated and the residue was chromatographed (silica gel, 25:10:1:1 to 15:10:1:1 EtOAc/EtOH/H$_2$O/NH$_4$OH) to give 2-13 as a white solid.

TLC R$_f$=0.29 (12:10:1:1 EtOAc/EtOH/H$_2$O/NH$_4$OH). $^1$H NMR (400 MHz, CD$_3$OD) δ 8.58 (s, 2H) 7.32 (d, J=7 Hz, 1H), 6.46 (d, J=7Hz, 1H), 3.43 (m, 2H), 3.11 (m, 1H), 2.84 (m, 2H), 2.72 (m, 2H), 2.64 (m, 4H), 1.83 (m, 2H) 1.75 (m, 1H), 1.61 (m, 1H), 1.46 (m, 2H).

SCHEME 3

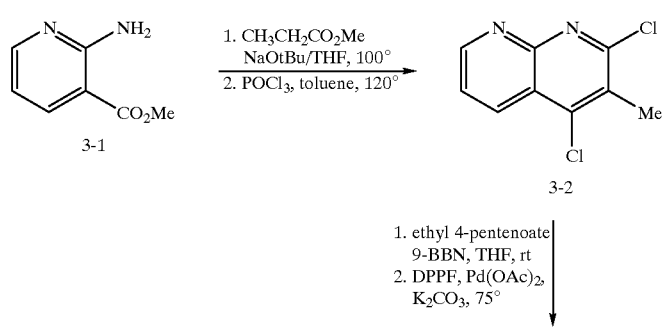

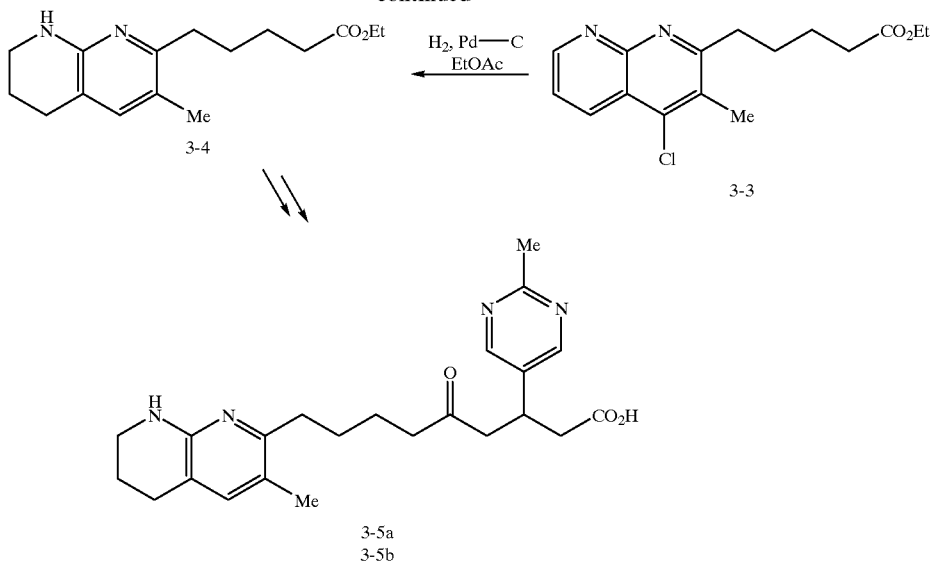

EXAMPLES 4 AND 5

3(R) and 3(S)-(2-Methylpyrimidin-5-yl)-5-oxo-9-(3-methyl-5,6,7,8-tetrahydro[1,8]-naphthyridin-2-yl)-nonanoic Acid (3-5a and 3-5b)

Step A: 2,4-Dichloro-3-methylnaphthyridine (3-2)

To a solution of methyl 2-aminonicotinate 3-1 (13.0 g. 86 mmol) and methyl propionate (200 mL) in 200 mL anhydrous THF was added sodium tert-butoxide (20.5 g, 214 mmol) gradually at room temperature. It was stirred at room temperature for 40 minutes and followed by refluxing at 100° C. for 4 hours. The reaction mixture was then cooled and concentrated. The residue was treated with 200 mL H$_2$O and neutralized to pH=7-8 with 3N HCl. The resulting solid was collected by filtration and dried under vacuum. It was then treated with phosphorus oxychloride (60 mL), refluxed at 120° C. for 3 hours and concentrated. The residue was diluted with 200 mL ice-H$_2$O and treated with Na$_2$CO$_3$ to pH>10. After filtration, the desired product 3-2 was collected as a yellow solid.

$^1$H NMR (300 MHz, CDCl$_3$) δ 9.11 (dd, J=4.2, 1.8 Hz, 1H), 8.56 (dd, J=8.4, 1.8 Hz, 1H), 7.59 (dd, J=8.4, 4.2 Hz, 1H), 2.71 (s, 3H).

Step B: Ethyl 5-(4-chloro-3-methyl-[1,8]-naphthyridin-2-yl)pentanoate (3-3)

To a solution of ethyl 4-pentenoate (2.5 g, 20 mmol) in 60 mL THF was added 9-BBN (0.5 M in THF, 47 mL, 23 mmol) gradually at room temperature. After stirring for 10 hours, it was treated with Pd(OAc)$_2$ (0.4 g, 2.0 mmol), 1,1'-bis(diphenylphosphino)-ferrocene (DPPF) (1.1 g, 2.0 mmol), K$_2$CO$_3$ (powder, 8.1 g, 58 mmol), 2,4-dichloro-3-methyl-naphthyridine (L) (3.6 g, 20 mmol) and 50 mL DMF. The reaction mixture was purged with argon for 5 minutes and then refluxed at 75° C. for 24 hours. It was cooled to room temperature and treated with 10 mL ethanolamine and stirred for 30 minutes. The mixture was diluted with 400 mL H$_2$O and extracted with EtOAc(×3). The combined organic layers were washed with brine and dried. After solvent removal, the residue was purified by silica gel chromatography using EtOAc/hexanes (1:1) to give the desired product 3-3 as a liquid.

$^1$H NMR (400 MHz, CDCl$_3$) δ 9.05 (dd, J=4.4, 2.0 Hz, 1H), 8.54 (dd, J=8.0, 2.0 Hz, 1H), 7.51 (dd, J=8.0, 4.4 Hz, 1H), 4.13 (q, J=7.2, 2H), 3.09 (m, 2H), 2.60 (s, 3H), 2.40 (mn, 2H), 1.96 (m, 3H), 1.82 (m, 3H), 1.25 (t, J=7.2, 3H).

Step C: Ethyl 5-(3-methyl-5,6,7,8-tetrahydro[1,8]-naphthyridin-2-yl)pentanoate (3-4)

A solution of the naphthyridine 3-3 (1.2 g) in EtOAc(100 mL) was degassed with argon, then 10% Pd on carbon (300 mg; wet; 50% water) was added and the mixture placed under an atmosphere of hydrogen gas using a balloon. After 16 hours, the mixture was charged with more catalyst (300 meg) and stirred for a further 6 hours. The mixture was filtered through celite and the solvent removed to yield a gum. This was dissolved in EtOAc, washed with saturated NaHCO$_3$ then brine, dried (MgSO$_4$) and evaporated to give 3-4. Low resolution mass spectrum [M+H] found 277.2.

Step D: 3(R) and 3(S)-(2-Methylpyrimidin-5-yl)-5-oxo-9-(3-methyl-5,6,7,8-tetrahydro[1,8]naphthyridin-2-yl)nonanoic Acid (3-5a and 3-5b)

Following procedures described in Scheme 1 for the conversion of 1-5 into 1-11a and 1-11b, 3-5a and 3-5b were prepared from 3-4 as both the resolved (R)- and (S)-enantiomers, each one a solid. Resolution of the enantiomers was carried out by chiral chromatography of the keto diester intermediate corresponding to 1-8.

$^1$H NMR (300 MHz, CD$_3$OD) δ 8.65 (s, 2H), 7.34 (s, 1H), 3.97 (m, 1H), 3.53–3.21 (m, 4H), 2.90–2.63 (m, 8H), 2.59 (s, 3H), 2.13 (s, 3H), 1.93 (m, 2H), 1.57 (m, 4H).

Scheme 4

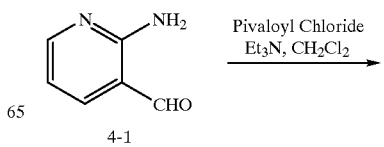

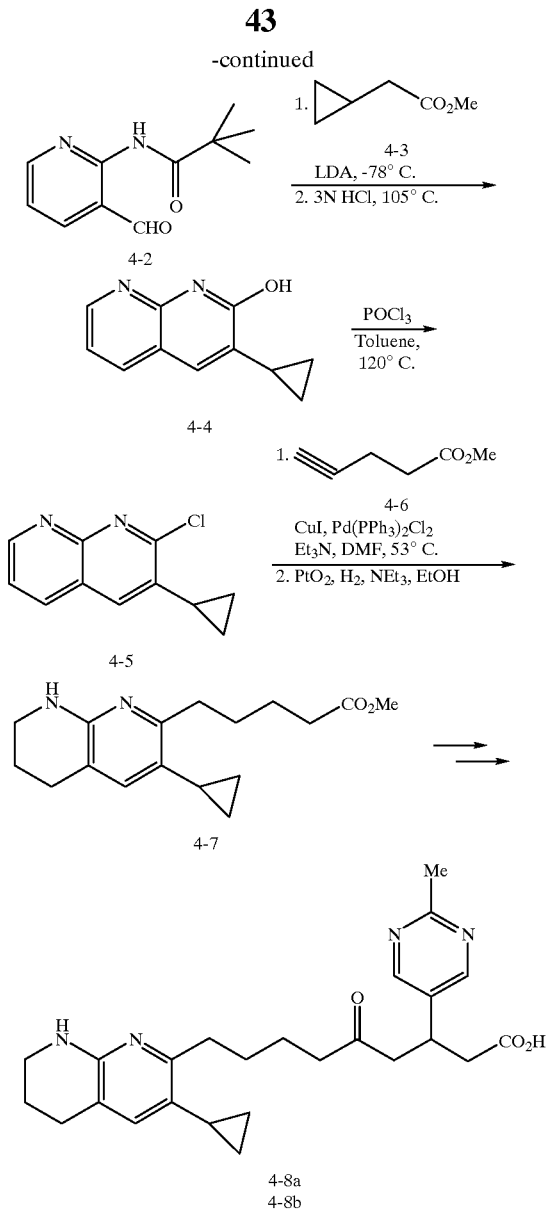

EXAMPLE 6

3(R) and 3(S)-(2-Methylpyrimidin-5-yl)-5-oxo-9-(3-cyclopropyl-5,6,7,8-tetrahydro[8]naphthyridin-2-yl)-nonanoic Acid (4-8a and 4-8b)

Step A: N-(3-Formyl-pyridin-2-yl)-2,2-dimethyl-propionamide (4-2).

To a cooled (0° C.) solution of 2-amino-3-formylpyridine 1-3 (preparation shown in Scheme 1, 50g, 409 mmol) in 700 mL of anhydrous $CH_2Cl_2$ were added $Et_3N$ (80 mL, 532 mmol) in one portion and a solution of trimethylacetyl (pivaloyl) chloride (65 mL, 491 mmol) in 50 mL $CH_2Cl_2$ gradually over 40 min. The reaction mixture was stirred 30 min and concentrated to a syrup, then 200 mL water was added. The mixture was extracted with ethyl acetate (×3). The combined organic layers were washed with water, brine and dried over $MgSO_4$ and concentrated to obtain the desired product 4-2 as a solid.

$^1$H NMR (400 MHz, $CDCl_3$): δ 10.85 (s, 1H), 8.70 (s, 1H), 8.0 (s, 1H), 7.20 (q, 1H), 1.30 (s, 9H).

Step B: 3-Cyclopropyl-[1,8]naphthyridin-2-ol (4-4).

To a cooled solution (−78° C.) of LDA (2.0 M, 251 mmol) in 600 mL THF was added ester 4-3 (prepared from cyclopropylacetic acid and methanolic HCl solution, 15 g, 131 mmol) gradually over 30 min. The reaction mixture was stirred for 30 min at −78° C. Aldehyde 4-2 (22.5 g, 109 mmol) in 40 mL THF was added. The reaction mixture was stirred at −78° C. for 1 hr, then was warmed up to room temperature over 1 hr and quenched with 200 mL $NH_4Cl$ (sat.). The mixture was extracted with ethyl acetate (×3). The combined organic layers were washed with water, brine and dried over $MgSO_4$ and concentrated to give a viscous residue which was subsequently dissolved in 200 mL 3N HCl. The mixture was refluxed at 105° C. for 24 hr. After concentration, the residue was poured into 500 mL ice-water and quenched with $K_2CO_3$ gradually (pH=9) to yield a solid as the desired product 4-4, which was filtered and dried in vacuum.

$^1$H NMR (400 MHz, $CD_3OD$): δ 8.45 (q, 1H), 7.99 (q, 1H), 7.47 (s, 1H), 7.23 (q, 1H), 2.14 (m, 1H), 1.01 (m, 2H), 0.78 (m, 2H).

Step C: 2-Chloro-3-cyclopropyl-[1,8]naphthyridine (4-5).

A mixture of naphthyridine 4-4 (14 g, 77 mmol) and 100 mL $POCl_3$ and 0.1 mL DMF was refluxed at 120° C. for 3 hr and concentrated. The residue was treated with 300 mL ice-water and solid $K_2CO_3$ until pH=9. The mixture was extracted with ethyl acetate (×3), washed with brine and dried over $MgSO_4$. After solvent removal, the desired compound 4-5 was obtained as a yellowish solid.

$^1$H NMR (400 MHz, $CDCl_3$): δ 9.00 (q, 1H), 8.10 (q, 1H), 7.78 (s, 1H), 7.50 (q, 1H), 2.34 (m, 1H), 1.00 (m, 2H), 0.82 (m, 2H).

Step D: 5-(3-Cyclopropyl-5,6,7,8-tetrahydro[1,8]naphthyridin-2-yl)-pentanoic Acid Methyl Ester (4-7).

A mixture of naphthyridine 4-5 (15.8 g, 77.2 mmol), ester 4-6 (prepared from 4-pentynoic acid and methanolic HCl solution, 11.3 g, 100.4 mmol), CuI (0.7 g, 3.9 mmol), 100 mL $Et_3N$ and 100 mL DMF was gently degassed with argon for 10 min. Then $Pd(PPh_3)_2Cl_2$ was added in one portion. The reaction mixture was heated at 53° C. for 20 hr, cooled to room temperature and quenched with 500 mL water and 100 mL $NaHCO_3$ (sat.). The aqueous mixture was extracted with ethyl acetate (×3). The combined organic layer was washed with brine and dried over $MgSO_4$. After solvent removal, the residue was purified by silica gel flash chromatography (EtOAc/Hexane=¼ to 100% EtOAc over 30 min) to obtain an oil, which was subsequently dissolved in 150 mL THF and 50 mL EtOH. $Et_3N$ (15 mL, 104 mmol) and $PtO_2$ (0.7 g) were added. The mixture was degassed under moderate vacuum and subjected to balloon hydrogenation condition for 6 hrs. It was then filtered and concentrated to provide the desired product 4-7 as an oil.

$^1$H NMR (400 MHz, $CDCl_3$): δ 6.80 (s, 1H), 4.75 (s, 1H), 3.62 (s, 3H), 3.36 (m, 2H), 2.76 (t, 2H), 2.64 (t, 2H), 2.36 (t, 2H), 1.88 (m, 2H), 1.78 (m, 5H), 0.86 (m, 2H), 0.50 (m, 2H).

Step E: 3(R) and 3(S)-(2-Methylpyrimidin-5-yl)-5-oxo-9-(3-cyclopropyl-5,6,7,8-tetrahydro[1,8]naphthyridin-2-yl)-nonanoic Acid (4-8a and 4-8b)

Following procedures described in Scheme 1 for the conversion of 1-5 into 1-h1a and 1-11b, 4-8a and 4-8b were prepared from 4-7, each as a solid. Resolution of the enantiomers was carried out by chiral chromatography of the keto diester intermediate corresponding to 1-8.

$^1$H NMR (300 MHz, $CD_3OD$): δ δ 8.65 (s, 2H), 7.22 (s, 1H), 3.74 (m, 1H), 3.40 (t, 2H), 3.10 (m, 1H), 2.90–2.40 (m, 14H), 1.95–1.60 (m, 5H), 0.94 (m, 2H), 0.60 (m, 2H).

Scheme 5

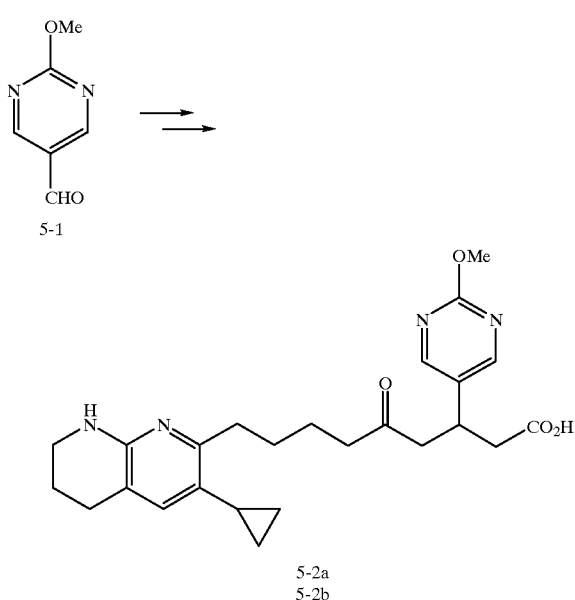

5-2a
5-2b

EXAMPLE 7

3(R) and 3(S)-(2-Methoxy-pyrimidin-5-yl)-5-oxo-9-(3-cyclopropyl-5,6,7,8-tetrahydro[1,8]naphthyridin-2-yl)-nonanoic Acid (5-2a and 5-2b)

Following procedures described in Schemes 1 and 4 but using 5-formyl-2-methoxypyrimidine 5-1 (for preparation, see U.S Pat. No. 5,552,546 and *J. Heterocyclic Chem.*, 28, 1281, 1991) as the starting, material, 5-2a and 5-2b were prepared and obtained as solids. Resolution of the enantiomers was carried out by chiral chromatography of the keto diester intermediate corresponding to 1-8.

$^1$H NMR (300 MHz, CD3OD) δ 8.50 (s, 2H), 7.21 (s, 1H), 3.97 (s, 3H), 3.71 (m, 1H), 3.41 (t, 2H), 3.04 (m, 1H), 2.83–2.46 (m, 10H), 1.95–1.60 (m, 6H), 0.94 (m, 2), 0.60 (m, 2H).

Scheme 6

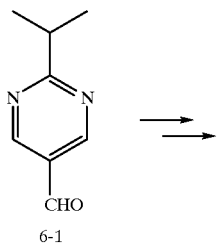

6-1

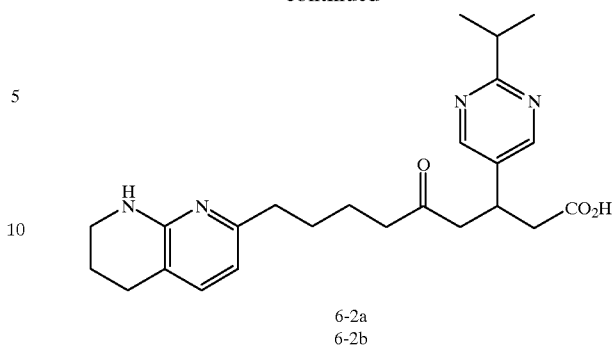

6-2a
6-2b

EXAMPLES 8 AND 9

3(R) and 3(S)-(2-Isopropyl-pyrimidin-5-yl)-5-oxo-9-(5,6,7,8-tetrahydro-[1,8]naphthyridin-2-yl)-nonanoic Acid (6-2a and 6-2b)

Enantiomers 6-2a and 6-2b were obtained from 2-isopropyl-5-formylpyrimidine (6-1) (for preparation, see *J. Heterocyclic Chem.*, 1991, 28,1281) utilizing the same methods described in Scheme 1 for the preparation of 1-11a and 1-11b. Resolution of the enantiomers was carried out by chiral chromatography of the keto diester intermediate corresponding to 1-8.

$^1$H NMR (400 MHz, CH$_3$OD): δ 8.65 (s, 2H), 7.40 (d, 1H, J=7 Hz), 6.47 (d, 1H, J=7 Hz), 3.70 (m, 1H), 3.43 (t, 2H), 3.14 (m, 2H), 2.76 (m,4H), 2.59 (m, 8H), 1.91 (m, 2H), 1.59 (m, 3H), 1.30 (d, 6H). Low resolution mass spectrum: calculated 424.6; found M+1: 425.3.

Scheme 7

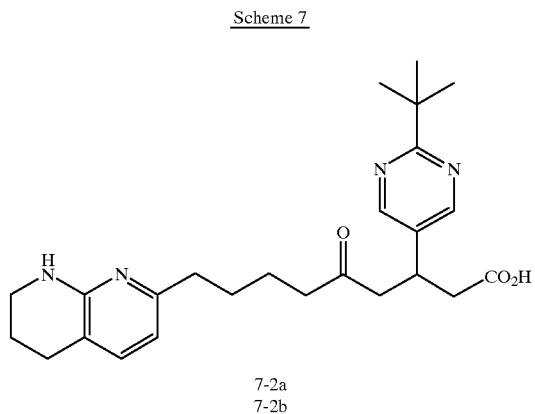

7-2a
7-2b

EXAMPLES 10 AND 11

3(R) and 3(S)-(2-tert-Butyl-pyrimidin-5-yl)-5-oxo-9-(5,6,7,8-tetrahydro-[1,8]naphthyridin-2-yl)-nonanoic Acid (7-2a and 7-2b)

Enantiomers 7-2a and 7-2b were obtained from 2-tert-butyl-5-formylpyrimidine (for preparation, see *J. Heterocy* clic Chem., 1991, 28,1281) utilizing the same methods described in Scheme 1 for the preparation of 1-11a and 1-11b. Resolution of the enantiomers was carried out by chiral chromatography of the keto diester intermediate corresponding to 1-8.

$^1$H NMR (400 MHz, CH$_3$OD) δ 8.63 (s, 2H), 7.40 (d, 1H, J=7 Hz), 6.47 (d, 1H, J=7 Hz), 3.70 (m, 1H), 3.43 (m, 2H), 3.14 (m, 1H), 2.76 (m, 2H), 2.59 (m, 8H), 1.91 (m, 2H), 1.59 (m, 3H), 1.36 (s, 9H). Low resolution mass spectrum: calculated: 438.6; found M+1: 439.3.

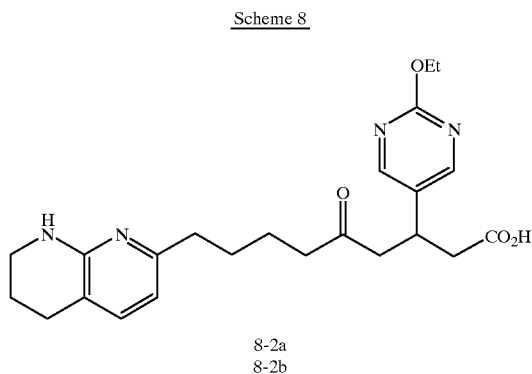

Scheme 8

8-2a
8-2b

EXAMPLES 12 AND 13

3(R) and 3(S)-(2-Ethoxy-pyrimidin-5-yl)-5-oxo-9-(5,6,7,8-tetrahydro-[1,8]naphthyridin-2-yl)-nonanoic Acid (8-2a and 8-2b)

Enantiomers 8-2a and 8-2b were obtained from 5-formyl-2-ethoxypyrimidine (for preparation, see U.S. Pat. No. 5,552,546 and *J. Heterocyclic Chem.*, 1991, 28,1281) utilizing the same methods described in Scheme 1 for the preparation of 1-11a and 1-11b. Resolution of the enantiomers was carried out by chiral chromatography of the keto diester intermediate corresponding to 1-8.

$^1$H NMR (400 MHz, CH$_3$OD): δ 8.48 (s, 2H), 7.40 (d, 1H, J=7 Hz), 6.47 (d, 1H, J=7 Hz), 4.37 (q, 2H), 3.67 (m, 1H), 3.39 (m, 2H), 3.07 (m, 1H), 2.75 (m, 3H), 2.50 (m, 7H) 1.94 (m, 2H), 1.64 (m, 4H), 1.37 (t, 3H). Low resolution mass spectrum: calculated: 426.5; found M+1: 427.0.

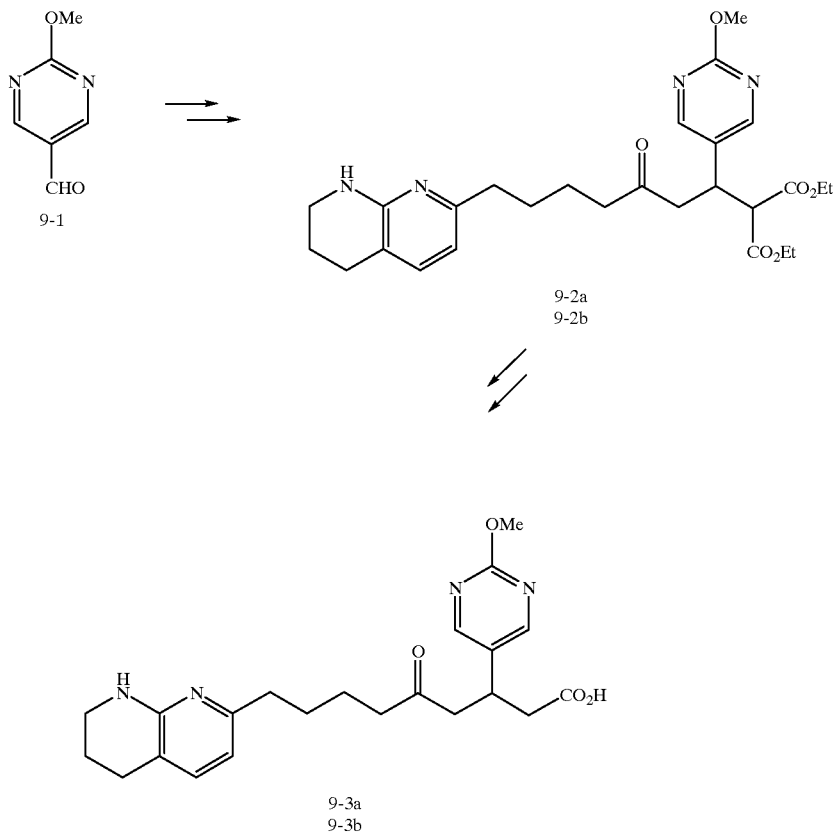

Scheme 9

EXAMPLES 13 AND 14
3(R) and 3(S)-(2-Methoxy-pyrimidin-5-yl)-5-oxo-9-(5,6,7,8-tetrahydro-[1,8]naphthyridin-2-yl)-nonanoic Acid (9-3a and 9-3b)

The 2-methoxy-pyrimidine-5-carboxaldehyde (9-1) (Gupton, J. T.; Gall, J. E.; Riesinger, S. W.; Smith, S. Q.; Bevirt, K. M.; Sikorski, J. A.; Dahl, M. L.; Arnold, Z., *J. Heterocyclic Chem.* 1991, 28, 1281) was converted into keto-diesters 9-2 as per Scheme 1. Separation of the enantiomers of racemic keto-diesters 9-2 was accomplished by HPLC (Chiralcel AD; 50×500 mm column; 70/20 isopropanol/hexanes/0.1% diethylamine over 60 minutes at a flow rate of 80.0 mL/min) to give two enantiomers ($R_T$=20–29 min and 32–40 min). Monohydrolysis, decarboxylation, and hydrolysis of diesters 9-2a and 9-2b as per Scheme 1 provided acids 9-3a and 9-3b.

TLC $R_f$=0.1 (15:15:0.5 EtOAc/EtOH/aq. NH$_4$OH). $^1$H NMR (300 MHz, CD$_3$OD): δ 8.50 (s, 2H), 7.41 (d, J=7.2 Hz, 1H), 6.47 (d, J=7.2 Hz, 1H), 3.96 (s, 3H), 3.67 (m, 1H), 3.43 (m, 2H), 3.01 (m, 1H), 2.76 (m, 3H), 2.50 (m, 6H), 1.96 (m, 2H), 1.62 (m, 4H) ppm.

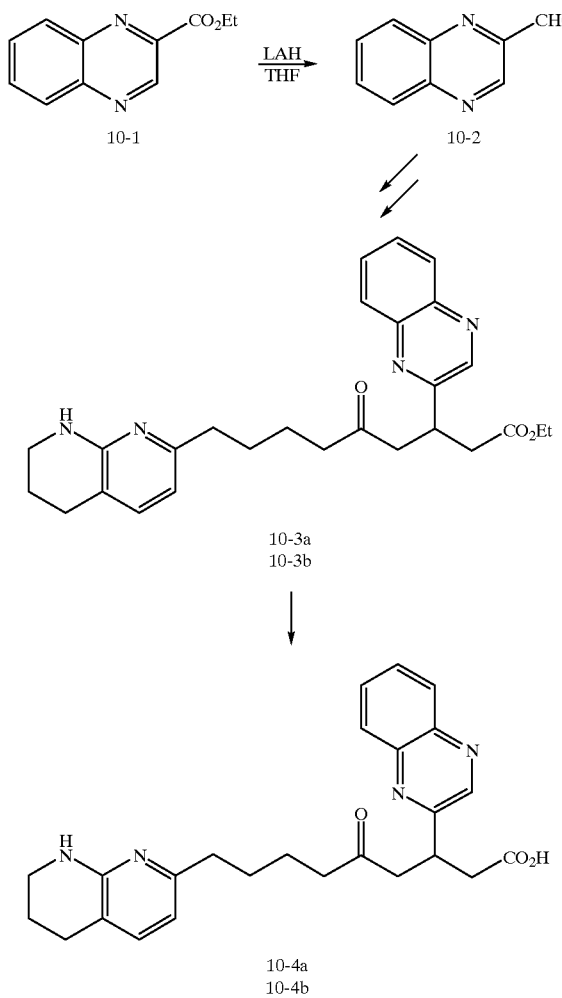

Scheme 10

10-4a
10-4b

EXAMPLE 15
3(R) and 3(S)-(Quinoxalin-2-yl)-5-oxo-9-(5,6,7,8-tetrahydro[1,8]naphthyridin-2-yl)-nonanoic Acid (10-3a and 10-3b)

Step A: 2-Quinoxalinecarboxaldehyde (10-2)

A solution of ethyl 2-quinoxalinecarboxylate (10-1) (2.34 g, 11.6 mmol) in tetrahydrofuran (22 mL) was cooled to −78° C. This solution was treated with a 1.0 molar THF solution of lithium aluminum hydride (5.80 mL, 5.80 mmol) added over a period of 6 min. After 30 min, the reaction was quenched with glacial acetic acid (1.30 mL, 22.71 mmol). The reaction mixture was warmed to room temperature and diluted with water (14 mL). The water was extracted five times with ethyl acetate and the combined organics washed with brine and dried (Na$_2$SO$_4$). The solvent was removed in vacuo. Preparative centrifugal TLC (SiO$_2$, 5 mm, CH$_2$Cl$_2$) afforded solid 10-2 (874 mg).

$^1$H NMR (CDCl$_3$, 400 MHz): δ 10.30 (s, 1H), 9.44 (s, 1H), 8.28–8.21 (m, 2H), 7.98–7.89 (mn, 2H). FABLRMS m/e 159 (M$^+$+H, C$_{15}$H$_{13}$NO$_6$=159).

Step B: 3(R) and 3(S)-(Quinoxalin-2-yl)-5-oxo-9-(5,6,7,8-tetrahydro-[1,8]naphthyridin-2-yl)-nonanoic Acid Ethyl Esters (10-3a and 10-3b)

Compound 10-3a and 10-3b were obtained from 2-quinoxalinecarboxaldehyde (10-2) utilizing the same methods described in Scheme 1 for the preparation of 1-10a and 1-11b. except that resolution of the enantiomers was carried out by chiral chromatography at this stage. Using a Chiralpak AS column and eluting with (hexanes w/0.4% diethylamine/MeOH/EtOH 70:15:15) at 7.0 ml/min the enantiomers 10-3a (faster eluting isomer) and 10-3b were separated.

$^1$H NMR (CDCl$_3$, 400 MHz) δ 8.87 (s, 1H), 8.08–8.05 (m, 1H), 7.97–7.94 (m, 1H), 7.72–7.67 (m, 2H), 7.02 (d, 1H, J=7.3 Hz), 6.26 (d, 1H, J=7.3 Hz), 4.84 (s, 1H), 4.10–4.00 (m, 3H), 3.40–3.36 (m, 2H), 3.24 (dd, 1H, J=17.8, 8.6 Hz), 2.93–2.87 (m, 2H), 2.74 (dd, 1H, J=16.2, 6.3 Hz), 2.67 (t, 2H, J=6.3 Hz), 2.47 (t, 2H, J=7.2 Hz), 2.41–2.38 (m, 2H), 1.92–1.86 (m, 2H), 1.60–1.50 (m, 4H), 1.14 (t, 3H, J=7.2 Hz),

Step C: 3(R) and 3(S)-(Quinoxalin-2-yl)-5-oxo-9-(5,6,7,8-tetrahydro-[1,8]naphthyridin-2-yl)-nonanoic Acid (104a and 104b) $^1$H NMR (CDCl$_3$, 400 MHz): δ 10.93 (br s, 1H), 8.08–8.02 (m, 2H), 7.75–7.68 (m, 2H), 7.19 (d, 1H, J=7.1 Hz), 6.24 (d, 1H, J=7.2 Hz), 4.31–4.24 (m, 1H), 3.44 (t, 2H, J=5.6 Hz), 3.31 (dd, 1H, J=16.0 Hz, 8.2 Hz), 3.01 (dd, 1H, J=16.1, 3.2 Hz), 2.92–2.48 (m, 2H), 2.76–2.65 (m, 5H), 1.95–1.70 (m, 4H), 1.61–1.52 (m, 1H0, 1.25 (s, 1H). FABLRMS m/e 433 (M$^+$+H, C$_{25}$H$_{28}$N4O$_3$=433).

Scheme 11

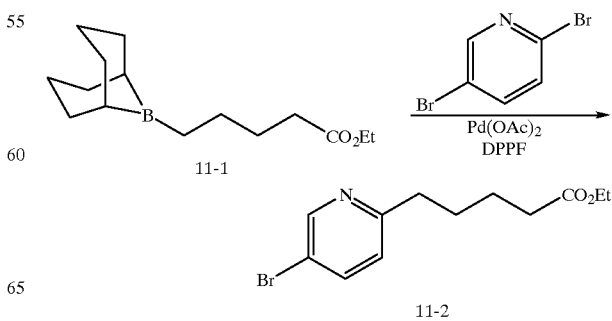

11-1

11-2

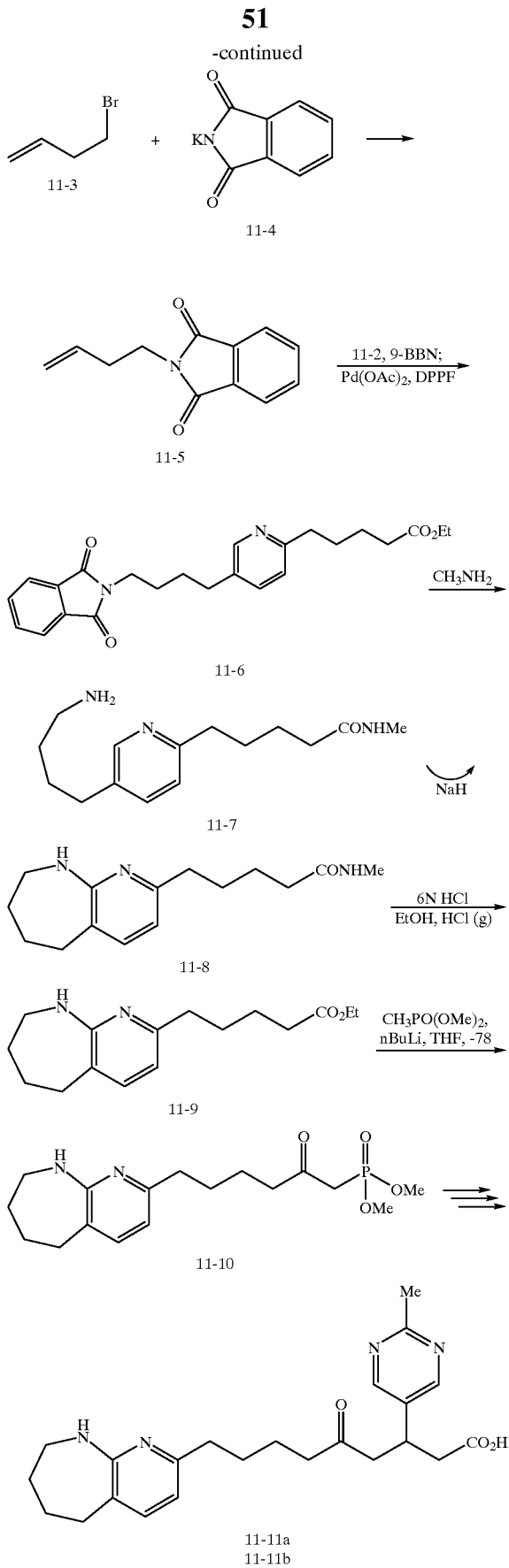

EXAMPLE 16

3(R) and 3(S)-(2-Methyl-pyrimidin-5-yl)-5-oxo-9-(6,7,8,9-tetrahydro-5H-pyrido[2,3-b]azepin-2-yl)-nonanoic Acid (11-11a and 11-11b)

Step A: 5-(5-Bromo-pyridin-2-yl)-Dentanoic Aacid Ethyl Ester (11-2)

To a stirred solution of ethyl-1-pentenoic acid (10 g, 78 mmol) in degassed TBF (80 mL) at 0° C. was added dropwise a solution of 9-BBN (187 mL of 0.5 M in TBF, 94 mmol) and the mixture stirred for 18 hours at ambient temperature to produce 11-1. $K_2CO_3$ (18.4 g, 133 mmol) and 2,5-dibromopyridine (18.5 g, 78 mmol) were added, followed by a premixed and aged (70° C. for 30 min) suspension of $Pd(OAc)_2$ (2.0 g, 8.9 mmol) and DPPF (5.4 g, 9.8 mmol) in degassed DMF (80 mL). The resulting mixture was stirred for 18 hours at 70° C., cooled, diluted with ethyl acetate, washed with water and brine, dried over $MgSO_4$, and concentrated. To the stirring residue dissolved in TBF (400 mL) was added water (150 mL) and $NaHCO_3$ (33 g) and after 10 minutes, $NaBO_3.H_2O$ (48 g). After vigorous stirring for 30 minutes, the mixture was diluted with ethyl acetate, washed with water and brine, dried over $MgSO_4$, and concentrated to an oil. The residue was chromatographed on silica gel (10–20% EtOAc/hexane) to give 11-2 as a colorless oil.

TLC $R_f$=0.75 (silica, 40% EtOAc/hexane). $^1$H NMR (400 MHz, $CDCl_3$): δ 8.57 (s, 1H), 7.70 (m, 1H), 7.05 (d, 1H, J=8 Hz), 4.15 (q, 2H, J=6 Hz), 2.77 (t, 2H, J=7 Hz), 2.34 (t, 2H, J=7 Hz), 1.7 (m, 4H), 1.26 (t, 3H, J=6 Hz).

Step B: 2-But-3-enyl-isoindole-1,3-dione (11-5)

To a stirred solution of 4-bromo-1-butene (11-3, 20 g, 148 mmol) in DMF (150 mL) was added potassium phthalimide (11-4, 25 g, 133 mmol) and the mixture stirred for 18 hours at 70° C. After cooling to RT, the mixture was diluted with ether, washed with water and brine, dried over $MgSO_4$, and concentrated to give 11-5 as a white solid.

$^1$H NMR (400 MHz, $CDCl_3$): δ 7.85 (m, 2H), 7.72 (m, 2H), 5.82 (m, 1H), 5.08 (m, 2H), 3.77 (t, 2H, J=7 Hz), 2.44 (m, 2H).

Step C: 5-{5-[4-(1,3-Dioxo-1,3-dihydro-isoindol-2-yl)-butyl]-pyridin-2-yl}-pentanoic Acid Ethyl Ester (11-6)

To a stirred solution of 11-5 (4.23 g, 21 mmol) in degassed THF (20 mL) at 0° C. was added dropwise a solution of 9-BBN (50.4 mL of 0.5 M in THF, 25.2 mmol) and the mixture stirred for 18 hours at ambient temperature. $K_2CO_3$ (5.0 g, 35.8 mmol) and 11-2 (5.0 g, 17.4 mmol) were added, followed by a premixed and aged (70° C. for 30 min) suspension of $Pd(OAc)_2$ (0.54 g, 2.4 mmol) and DPPF (1.45 g, 2.6 mmol) in degassed DMF (20 mL). The resulting mixture was stirred for 18 hours at 70° C., cooled, diluted with ethyl acetate, washed with water and brine, dried over $MgSO_4$, and concentrated. To the stirring residue dissolved in THF (200 mL) was added water (75 mL) and $NaHCO_3$ (16.5 g) and after 10 minutes, $NaBO_3.H_2O$ (24 g). After vigorous stirring for 30 minutes, the mixture was diluted with ethyl acetate, washed with water and brine, dried over $MgSO_4$, and concentrated to an oil. The residue was chromatographed on silica gel (20–40% EtOAc/hexane) to give 11-6 as a yellow solid.

TLC $R_f$=0.31 (silica, 50% EtOAc/hexane). $^1$H NMR (400 MHz, $CDCl_3$): δ 8.37 (s, 1H), 7.84 (m, 2H), 7.75 (m, 2H), 7.40 (m, 1H), 7.05 (m, 1H), 4.12 (q, 2H, J=7 Hz), 3.71 (m, 2H), 2.78 (t, 2H, J=7 Hz), 2.62 (t, 2H, J=7 Hz), 2.33 (t, 2H, J=7 Hz), 1.64 (m, 8H), 1.23 (t, 3H, J=6 Hz).

Step D: 5-[5-(4-Amino-butyl)-pyridin-2-yl]-pentanoic Acid Methylamide (11-7)

A mixture of 11-6 (45 g, 110 mmol) and a saturated solution of methylamine in methanol (300 mL) in a sealed tube was heated at 70° C. for 12 hours. The mixture was-cooled and concentrated to an oil. The residue was chromatographed on silica gel (10:10:1:1 EtOAc/EtOH/NH₄OH/H₂O) to give 11-7 as a yellow oil.

TLC R_f=0.16 (silica, 10:10:1:1 EtOAc/EtOH/NH4OH/H₂O). ¹H NMR (400 MHz, CDCl₃): δ 8.32 (s, 1H), 7.41 (m, 1H), 7.07 (m, 1H), 2.74 (m, 7H), 2.59 (t, 2H, J=6 Hz), 2.21 (t, 2H, J=6 Hz), 1.69 (m, 6H), 1.48 (m, 2H).

Step E: 5-(6,7,8,9-Tetrahydro-5H-pyrido[2,3-b]azepin-2-yl)-pentanoic Acid Methylamide (11-8)

A mixture of 11-7 (24 g, 91.2 mmol) and NaH (10.9 g of a 60% weight dispersion in mineral oil, 273 mmol) in xylenes (500 mL) was purged with argon for 30 min, and then heated at reflux for 72 hours. The mixture was cooled, quenched with ethanol, diluted with 10% aqueous potassium carbonate and extracted with ethyl acetate. The organics were dried over MgSO₄, and concentrated to an oil. The residue was chromatographed on silica gel (70:25:5 CHCl₃/EtOAc/MeOH/H₂O) to give 11-8 as a white solid.

TLC R_f=0.15 (silica, 70:25:5 CHCl₃/EtOAc/MeOH). ¹H NMR (400 MHz, CDCl₃): δ 7.24 (d, 1H, J=7 Hz), 6.53 (d, 1H, J=7 Hz), 5.43 (br s, 1H), 4.62 (br s, 1H), 3.12 (m, 2H), 2.79 (d, 3H, J=5 Hz), 2.63 (m, 4H), 2.18 (m, 2H), 1.81 (m, 2H), 1.68 (m, 6 Hz).

Step F: 5-(6,7,8,9-Tetrahydro-5H-pyrido[2,3-b]azepin-2-yl)-pentanoic Acid Ethyl Ester (11-9)

A mixture of 11-8 (3 g, 11.5 mmol) and 6 M HCl (100 mL) in a sealed tube was heated at 70° C. for 12 hours. The mixture was cooled and concentrated to an oil. The residue was azeotroped from ethanol (50 mL) twice, then dissolved in 4 M HCl in ethanol (100 mL) and heated at 70° C. for 1 hour. The mixture was cooled and concentrated to an oil. The residue was diluted with ethyl acetate, washed with 10% aqueous potassium carbonate and brine, dried over MgSO₄, and concentrated to give 11-9 as a brown oil.

TLC R_f=0.44 (silica, 70:25:5 CHCl₃/EtOAc/MeOH). ¹H NMR (400 MHz, CDCl₃): δ 7.22 (d, 1H, J=7 Hz), 6.53 (d, 1H, J=7 Hz), 4.63 (br s, 1H), 4.11 (q, 2H, J=7 Hz), 3.12 (m, 2H), 2.66 (m, 2H), 2.62 (t, 2H, J=6Hz), 2.33 (t, 2H, J=6 Hz), 1.70 (m, 2H), 1.63 (m, 6H), 1.27 (t, 3H, J=7 Hz).

Step G: 3(R) and 3(S)-(2-Methyl-pyrimidin-5-yl)-5-oxo-9-(6,7,8,9-tetrahydro-5H-pyrido[2,3-b]azepin-2-yl)-nonanoic Acid (11-11a and 1-11b)

Utilizing the procedures for the conversion of 1-5 into 1-11a and 1-11b, 11-9 was converted into l-11a and 11-11b by way of 11-10. Resolution of the enantiomers was carried out by chiral chromatography of the keto diester intermediate corresponding to 1–8 on a Chiralcel AD column (10 cm×50 cm) using 70% A/30% B (A=2-propanol; B=0.1% diethylamine in hexanes) at a flow rate of 250 mL/min.

TLC R_f=0.21 (silica, 10:10:1:1 EtOAc/EtOH/NH4OH/H2O). ¹H NMR (400 MHz, CDCl₃): δ 8.63 (s, 2H), 7.42 (d, 1H, J=7 Hz), 6.55 (d, 1H, J=7 Hz), 3.64 (m, 1H), 3.31 (m, 2H), 3.05 (m, 1H), 2.87 (m, 1H), 2.77 (m, 2H), 2.58 (m, 9H), 1.84 (m, 4H), 1.57 (m, 4H).

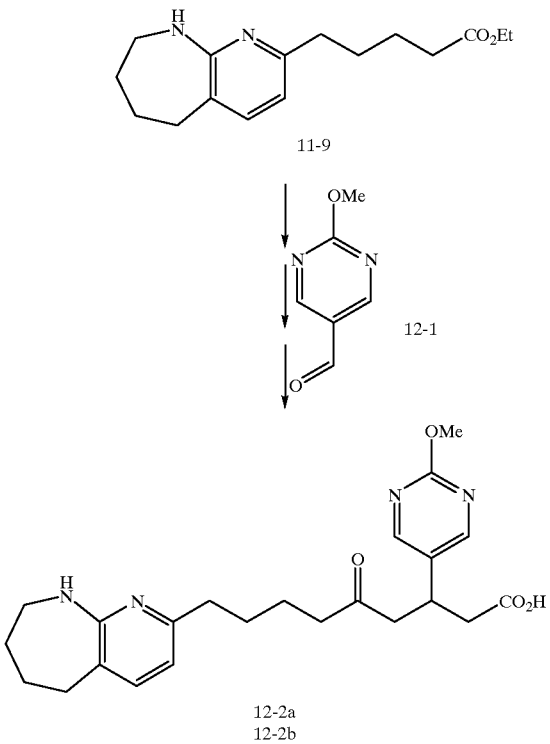

Scheme 12

12-1

12-2a
12-2b

EXAMPLE 17

3(R) and 3(S)-(2-Methoxy-pyrimidin-5-yl)-5-oxo-9-(6,7,8,9-tetrahydro-5H-pyrido[2,3-b]azepin-2-yl)-nonanoic Acid (12-2a and 12-2b)

Utilizing the procedures for the conversion of 1-5 into 1-11a and 1-11b, 11-9 and 2-methoxy-pyrimidine-5-carbaldehyde (12-1, for preparation, see *J. Heterocycl. Chem.* (1991), 28, 1281) were converted into 12-2a and 12-2b. 10 Resolution of the enantiomers was carried out by chiral chromatography of the keto diester intermediate corresponding to 1–8 on a Chiralcel AD column (10 cm×50 cm) using 70% A/30% B (A=2-propanol; B=0.1% diethylamine in hexanes) at a flow rate of 250 mL/min.

TLC R_f=0.21 (silica, 10:10:1:1 EtOAc/EtOH/NH4OE/H₂O). ¹H NMR (400 MHz, CDCl₃): δ 8.48 (s, 2H), 7.42 (d, 1H, J=7 Hz), 6.56 (d, 1H, J=7 Hz), 3.94 (s, 3H), 3.62 (m, 1H), 3.29 (m, 2H), 2.98 (m, 1H), 2.85 (m, 1H), 2.79 (m, 2H), 2.58 (m, 2H), 1.84 (m, 4H), 1.57 (m, 4H).

Scheme 13

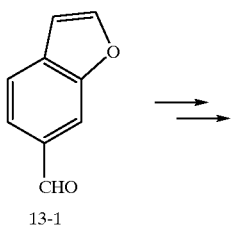

13-1

EXAMPLE 18

3(R) and 3(S)-(2,3-Dihydro-benzofuran-6-yl)-5-oxo-9-(5,6,7,8-tetrahydro-[1,8]naphthyridin-2-yl)-nonanoic Acid (13-4a and 134b)

Step A: 3(R) and 3(S)-(Benzofuran-6-yl)-5-oxo-9-(5,6,7,8-tetrahydro-[1,8]naphthyridin-2-yl)-nonanoic acid ethyl ester (13-2a and 13-2b)

Utilizing the procedures for the conversion of 1-5 into 1-10a and 1-10b, benzofuran-6-carbaldehyde (13-1, prepared as described in Askew, B., et. al., PCT Int. Appl. (1999) WO 99/31061) was converted into 13-2a and 13-2b. Resolution of the enantiomers was carried out by chiral chromatography of the keto diester intermediate corresponding to 1-8 on a Chiralcel OD column.

$^1$H NMR (400 MHz, CDCl$_3$): δ 7.57 (s, 1H), 7.48 (d, 1H, J=8 Hz), 7.36 (s, 1H), 7.10 (d, 1H, J=7 Hz), 7.02 (d, 1H, J=7 Hz), 6.70 (s, 1H), 6.26 (d, 1H, J=7 Hz), 7.47 (br s, 1H), 4.02 (q, 2H, J=6 Hz), 3.79 (m, 1H), 3.37 (m, 2H), 2.82 (d, 2H, J=7 Hz ), 2,68 (m, 4H), 2.47 (m, 2H), 2.33 (m, 2H), 1.88 (m, 2H), 1.52 (m, 4H), 1.13 (t, 2H, J=6 Hz).

Step B: 3(R) and 3(S)-(2,3-Dihydro-benzofuran-6-yl)-5-oxo-9-(5,6,7,8-tetrahydro-[1,8]naphthyridin-2-yl)-nonanoic Acid Ethyl Ester (13-3a and 13-3b)

A mixture of 13-2a or 13-2b (0.4 g, 0.89 mmol) and 20% Pd(OH)$_2$ on charcoal (200 mg) in ethanol (20 mL) was stirred under a balloon of hydrogen for 18 hours, then filtered and concentrated to give 13-3a or 13-3b as a yellow oil.

$^1$H NMR (400 MHz, CDCl$_3$): δ 7.08 (m, 2H), 6.67 (m, 1H), 6.62 (s, 1H), 6.29 (d, 1H), J=7 Hz), 4.51 (t, 2H, J=9 Hz), 4.03 (m, 2H), 3.61 (m, 1H), 3.42 (m, 2H), 3.13 (t, 2H, J=7 Hz), 2.66 (m, 4H), 2.56 (m, 4H), 2.33 (m, 2H), 1.86 (m, 2H), 1.52 (m, 2H), 1.18 (t, 3H, J=7 Hz).

Step C: 3(R) and 3(S)-(2,3-Dihydro-benzofuran-6-yl)-5-oxo-9-(5,6,7,8-tetrahydro-[1,8]naphthyridin-2-yl)-nonanoic Acid (13-4a and 13-4b)

Utilizing the procedures for the conversion of 1-10a into 1-11a, 13-3a and 13-3b were converted into 13-4a and 13-4b, respectively.

$^1$H NMR (400 MHz, CDCl$_3$): δ 7.38 (d, 1H, J=7 Hz), 7.08 (d, 1H, J=7 Hz), 6.71 (d, 1H, J=7 Hz), 6.63 (s, 1H), 6.44 (d, 1H, J=7 Hz), 4.48 (t, 2H, J=9 Hz), 3.62 (m, 1H), 3.41 (t, 2H, J=5 Hz), 3.12 (t, 2H, J=8 Hz), 2.91 (m, 1H), 2.75 (t, 2H, J=5 Hz), 2.62 (m, 5H), 2.42 (m, 2H), 1.91 (m, 2H), 1.63 (m, 3H), 1.51 (m, 1H).

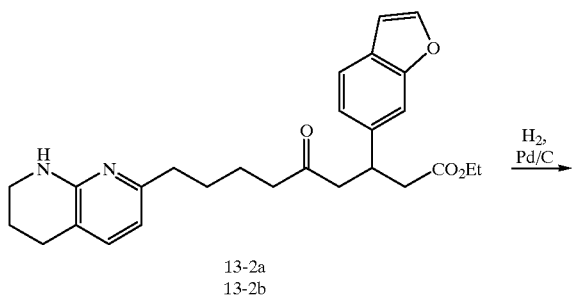

13-2a
13-2b

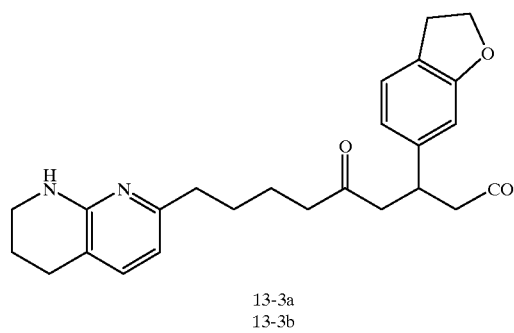

13-3a
13-3b

| NaOH

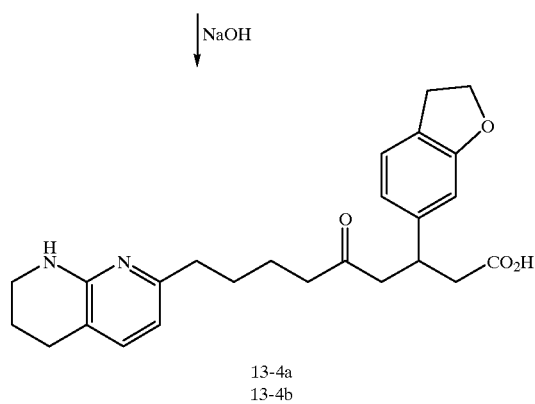

13-4a
13-4b

Scheme 14

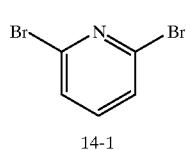

14-1

→ 4-methoxy-benzylamine / DIPEA, dioxane, Δ, 91%

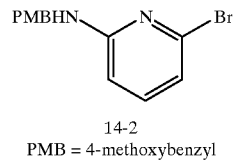

14-2
PMB = 4-methoxybenzyl

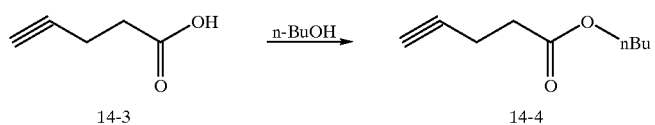

14-3 → n-BuOH → 14-4

14-2 + 14-4 → [(C$_6$H$_5$)$_3$P]$_2$PdCl$_2$ / CuI, Et$_3$N, 76%

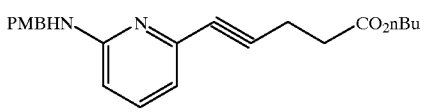

14-5

→ H$_2$, PtO$_2$, Et$_3$N, 94%

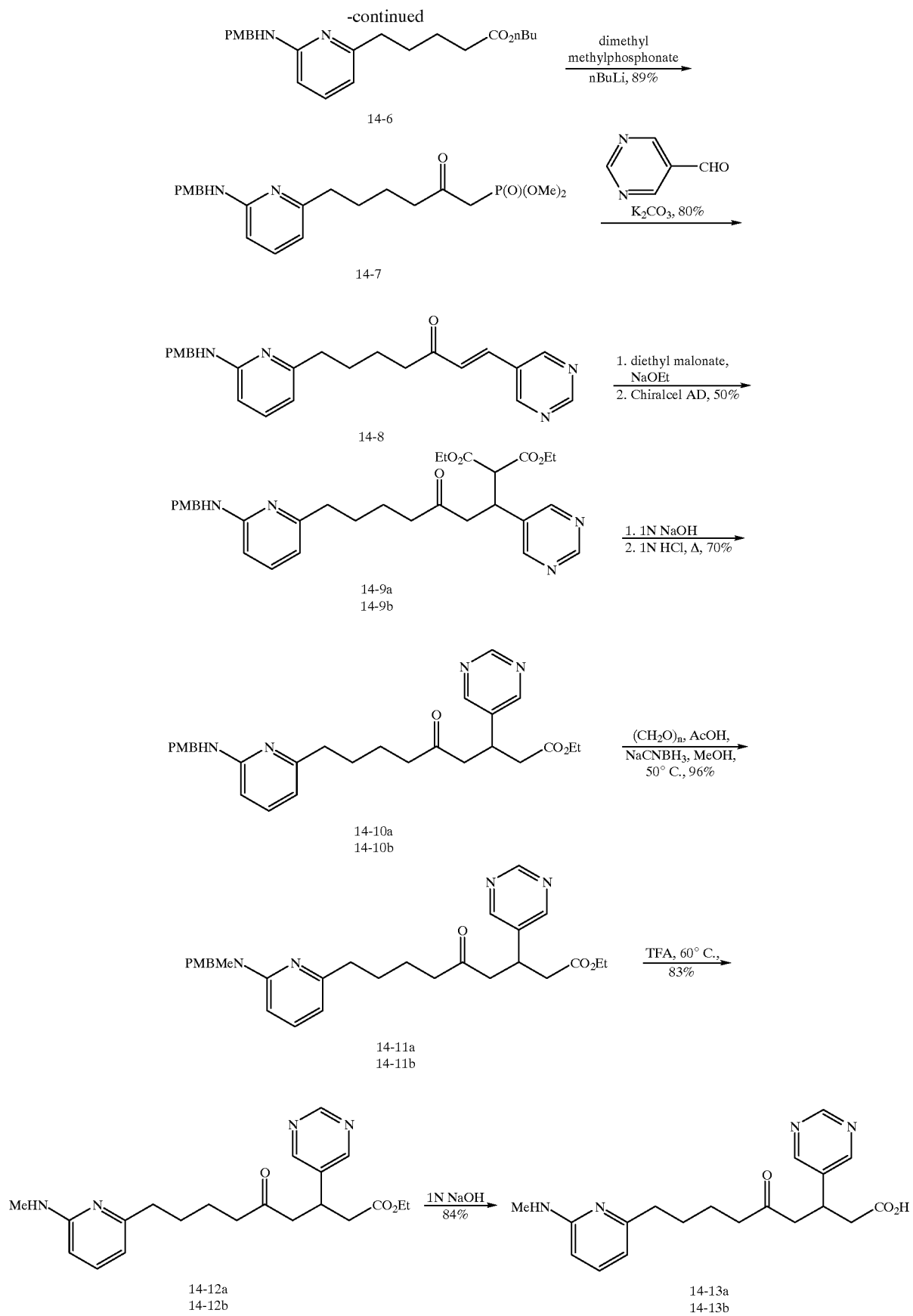

EXAMPLES 19 and 20

3(R) and 3(S)-9-(6-Methylamino-pyridin-2-yl)-5-oxo-3-(pyrimidin-5-yl)-nonanoic Acid (14-13a and 14-13b)

Step A: (6-Bromo-pyridin-2-yl)-(4-methoxy-benzyl)-amine (14-2)

A solution of 2,6-dibromopyridine (14-1) (37.3 g, 157 mmol), 4-methoxybenzylamine (21.6 g, 157 mmol), and diisopropylethylamine (22.4 g, 173 mmol) in 1,4-dioxane (150 mL) was heated at reflux for 24 h. The reaction mixture was cooled, concentrated in vacuo, and the residue was partitioned between EtOAc (100 mL) and saturated aqueous $NaHCO_3$ (125 mL). The organic layer was washed with water (100 mL) followed by brine (100 mL) and dried ($Na_2SO_4$). The organic layer was filtered, concentrated in vacuo, and purified by flash chromatography (silica, 10% to 40% EtOAc/hexanes) affording 42 g of amine 14-2 as a white solid in 91% yield. $^1$H NMR (300 Mz, $CDCl_3$): δ 8 7.26–7.22 (m, 3H), 6.88–6.86 (m, 2H), 6.75–6.73 (d 1H), 6.27–6.25 (d, 1H), 4.98–4.96 (br s, 1H), 4.39–4.37 (d, 2H), 3.80 (s, 3H).

Step B: Pent-4-ynoic acid butyl ester (14-4)

HCl was bubbled into a n-butanol solution (200 mL) of pent4-ynoic acid 14-3 (10 g, 102 mmol) for ten minutes. The solution stirred overnight at room temperature. The solvent was removed in vacuo providing the crude ester 14-4 as a yellow liquid in quantitative yield.

$^1$H NMR (400 MHz, $CDCl_3$): δ 4.12–4.09 (t, 2H), 2.55–2.50 (m, 4H), 1.98–1.96 (t, 1H), 1H), 1.63–1.60 (m, 2H), 1.41–1.35 (m, 2H), 0.95–0.91 (t, 3H).

Step C: 5-[6-(4-Methoxy-benzylamino)-pyridin-2-yl]-pent-4-ynoic acid butyl ester (14-5)

To a mixture of 14-2 (8.64 g, 29.48 mmol) and 14-4 (5.0 g, 32.4 mmol) in $Et_3N$ (50 mL) at 0° was added CuI (0.14 g, 0.74). The solution was purged with argon and $[(C_6H_5)_3P]_2PdCl_2$ (0.52 g, 0.74 mmol) was added. After 1 h the cooling bath was removed and the solution was stirred for an additional 12 h. The solution was diluted with diethyl ether (250 mL) and washed with water (4×100 ml) followed by brine (100 mL). The ethereal layer was dried ($Na_2SO_4$), concentrated, and chromatographed (silica gel, 30% ethyl acetate/hexanes) to give 8.6 g of 14-5.

$^1$H NMR (400 MHz, $CDCl_3$): δ 7.34–7.30 (t, 1H), 7.26–7.24 (m, 2H), 6.87–6.85 (m, 2H), 6.72–6.70 (d, 1H), 6.29–6.27 (d, 1H), 4.91–4.88 (t, 1H), 4.40–4.38 (d, 2H), 4.13–4.11 (t, 2H), 3.79 (s, 3H), 2.74–2.72 (m, 2H), 2.66–2.64 (m, 2H), 1.66–1.5 (m, 2H), 1.42–1.34 (m, 2H), 0.94–0.90 (t, 3H).

Step D: 5-[6-(4-Methoxy-benzylamino)-pyridin-2-yl]-pentanoic acid butyl ester (14-6)

A mixture of 14-5 (6.54 g, 17.8 mmol), $Et_3N$ (1.85 mL, 13.3 mmol), and $PtO_2$ (0.405 g, 1.78) in EtOH (150 mL) was stirred under a balloon of hydrogen for 6 h. Filtration through celite and evaporative removal of the solvent afforded 6.23 g of 14-6 as a colorless oil. The crude product was used directly in the next step without purification.

$^1$H NMR (400 MHz, $CDCl_3$): δ 7.34–7.27 (m, 3H), 6.87–6.85 (m, 2H), 6.45–6.43 (d, 1H), 6.19–6.17 (d, 1H), 4.79–4.76 (t, 1H), 4.38–4.37 (d, 2H), 4.07–4.05 (t, 2H), 3.79 (s, 3H), 2.64–2.59 (m, 2H), 2.35–2.31 (m, 2H), 1.76–1.68 (m, 4H), 1.62–1.55 (m, 2H), 1.42–1.33 (m, 2H), 0.94–0.92 (t, 3H).

Step E: {[6-r6-(4-Methoxy-benzylamino)-pyridin-2-yl]-2-oxo-hexyl}-phosphonic acid dimethyl ester (14-7)

A solution of dimethyl methylphosphonate (2.48 g, 20 mmol) in anhydrous THF (30 mL) was cooled to −78° and treated dropwise with 2.5 M n-BuLi (8.0 mL). After stirring at −78° for 45 min, a solution of ester 14-6 (1.85 g, 5.0 mmol) in THF (10 rnL) was added dropwise and the resulting solution stirred for 30 min at −78°, quenched with sat. $NH_4Cl$ (25 mL), then extracted with ethyl acetate (3×75 mL). The combined organic extracts were dried ($Na_2SO4$), filtered, and concentrated to afford a yellow oil. Chromatography on silica gel (5% $MeOH/CH_2Cl_2$) afforded 14-7 as a yellow oil in 89% yield.

$^1$H NMR (400 MHz, $CDCl_3$): δ 7.33–7.26 (m, 3H), 6.87–6.85 (m, 2H), 6.44–6.43 (d, 1H), 6.19–6.17 (d, 1H), 4.834.79 (t, 1H), 4.38–4.37 (d, 2H), 3.79 (s, 3H), 3.78 (s, 3H), 3.76 (s, 3H), 3.13–3.04 (m, 2H), 2.66–2.58 (m, 4H), 1.70–1.64 (m, 4H).

Step F: 7-[6-(4-Methoxy-benzylamino)-pyridin-2-yl]-1-pyrimidin-4-yl-hept-1-en-3-one (14-8)

To a solution of 14-7 (1.87 g, 4.44 mmol), pyrimidine-5-carbaldehyde (0.480 g, 4.44 mmol) in 15 mL DMF was added $K_2CO_3$ (0.922 g, 6.67 mmol). The mixture was stirred at ambient temperature for 15 hr, and concentrated to a paste. The residue was diluted with water, extracted with ethyl acetate, and dried over sodium sulfate. Following concentration, the residue was chromatographed on silica gel (5% $MeOH/CH_2Cl_2$) to give 1.44 g of 14-8 as a white solid.

$^1$H NMR (300 MHz, $CDCl_3$): δ 9.19 (s, 1H), 8.88(s, 2H), 7.47–7.29 (m, 4H), 6.87–6.82 (m, 3H), 6.47–6.45 (d, 1H), 6.21–6.18 (d, 1H), 4.82–4.78 (t, 1H), 4.39–4.37 (d, 2H), 3.79 (s, 3H), 2.73–2.62 (m, 4H), 1.77–1.74 (m, 4H).

Step G: 3(S or R)-2-{7-[6-(4-Methoxy-benzylamino)-pyridin-2-yl]-3-oxo-1-pyrimidin-4-yl-heptyl}-malonic acid diethyl ester (14-9a and 14-9b)

To a solution of 14:8 (0.719 g, 1.78 mmol) and diethyl malonate (0.326 ml, 2.14 mmol) in ethanol (10 nL) and THF (10 mL) was added sodium ethoxide (0.01 mL of a 30% w/w solution in ethanol). After 1 hr, the mixture was diluted with EtOAc (75 rnL) and washed with sat'd $NaHCO_3$ (75 mL) followed by brine (75mL). The organic layer was dried, concentrated, and purified on a 5×50 cm Chiralcel OD column (flow=100 mL/min, A:B=10:90) (A=0.1% diethylamine/ethanol, B=2-propanol). Product 14-9a (0.246 g) eluted at 35 minutes; its enantiomer, 14-9b, (0.260 g) eluted at 47 minutes.

$^1$H NMR (400 MHz, $CDCl_{13}$): δ 9.05 (s, 1H), 8.67 (s, 2H), 7.33–7.26 (m, 3H), 6.87–6.85 (d, 2H), 6.42–6.38 (d, 1H), 6.19–6.17 (d, 1H), 4.88–4.84 (br s, 1H), 4.37–4.36 (d, 2H), 4.21–4.16 (m, 2H), 4.05–3.95 (m, 4H), 3.79 (s, 3H), 3.74–3.72 (d, 1H), 3.06–2.91 (m, 2H), 2.57–2.53 (t, 2H), 2.44–2.27 (m, 2H), 1.26–1.20 (m, 6H), 1.10–1.06 (t, 3H).

Step H: 3(S or R)-9-[6-(4-Methoxy-benzylamino)-pyridin-2-yl]-5-oxo-3-pyrimidin-5-yl-nonanoic acid ethyl ester (14-10a)

To a solution of 14–9a (0.240 g, 0.426 mmol) in ethanol (5 mL) was added NaOH (0.469 mL of 1N solution in water, 0.469 mmol). After stirring at 40° C. for 30 minutes, the mixture was treated with HCl (0.469 mL of 1N solution in water, 0.469 mmol) and concentrated. The residue was suspended in toluene (15 mL) and heated at reflux. After 1 h, evaporation of the solvent and purification on silica gel (70 chloroform/20 ethyl acetate/10 methanol) afforded 14-10a as a yellow oil in 70% yield.

$^1$H NMR (400 MHz, $CDCl_3$): δ 9.06 (s, 1H), 8.63 (s, 2H), 7.32–7.26 (m, 3H), 6.87–6.85 (d, 2H), 6.42–6.38 (d, 1H), 6.19–6.17 (d, 1H), 4.88–4.84 (br s, 1H), 4.05–4.03 (q, 2H), 3.79 (s, 3H), 3.73–3.65 (m, 1H) 2.93–2.70 (m, 3H), 2.63–2.54 (m, 3H), 2.44–2.15 (m, 4H), 1.17–1.13 (t, 3H).

Step I: 3(S or R)-9{6-[(4-Methoxy-benzyl)-methyl-amino]-pyridin-2-yl -5-oxo-3-pyrimidin-5-yl-nonanoic acid ethyl ester (14-11a)

To a solution of 14-10a (0.145 g, 0.295 mmol) in methanol (5 mL) was added paraformaldehyde (0.075 ng) and acetic acid (0.085 mL, 1.47 mmol). After stirring at 50° C. for 15 minutes, NaCNBH₃ (0.024 g, 0.384 mmol) was added and the mixture stirred for an additional 12 h at 50° C. Evaporation of the solvents and purification on silica gel (5% MeOH/CHCl₃) afforded 14-11a in 96% yield.

1H NMR (400 MHz, CDCl₃): δ 9.06 (s, 1H), 8.63 (s, 2H), 7.35–7.31 (t, 1H), 7.16–7.14 (d, 2H), 6.83–6.81 (d, 2H), 6.37–6.35 (d, 1H), 6.30–6.28 (d, 1H), 4.74 (s, 2H), 4.07–4.02 (q, 2H), 3.78 (s, 3H), 3.71–3.64 (m, 1H) 2.97 (s, 3H), 2.90–2.69 (m, 3H), 2.62–2.56 (m, 3H), 2.43–2.28 (m, 2H), 1.70–1.52 (m, 4H), 1.17–1.13 (t, 3H).

Step J: 3(S or R)-9-(6-Methylamnino-pyridin-2-yl)-5-oxo-3-(pyrimidin-5-yl)-nonanoic acid ethyl ester (14-12a)

A solution of 14-11a (0.140 g, 0.277 mmol) in trifluoroacetic acid (1 mL) was stirred at 60° C. for 15 minutes. The solvent was evaporated and the residue was azeotroped (2×25 ml toluene). Purification on silica gel (90:10:1 CHCl₃:MeOH:NH₄OH) gave 14-12a.

¹H NMR (400 MHz, CDCl₃): δ 8 9.07 (s, 1H), 8.64 (s, 21H), 7.38–7.35 (t, 1H), 6.41–6.39 (d, 1H), 6.20–6.18 (d, 1H), 4.54–4.50 (br s, 1H), 4.05–4.03 (q, 2H), 3.73–3.65 (m, 1H), 2.93–2.87 (m, 4H) 2.83–2.70 (m, 2H), 2.64–2.53 (m, 3H), 2.42–2.35 (m, 2H 1.64–1.56 (m, 4H), 1.17–1.13 (t, 3H).

Step K: 3(S or R)-9-(6-Methylamino-pyridin-2-yl)-5-oxo-(3-pyrimidin-5-yl)-nonanoic acid (14-13a)

To a solution of 14-12a (0.0899 g, 0.233 mmol) in THF/MeOHEH₂O 3:1:1 (5 mL)) was added NaOH (0.534 nL of 1N solution in water, 0.534 mmol). After 30 minutes, the mixture was neutralized with HCl (0.534 mL of 1N solution in water, 0.534 mmol) and the solvents were evaporated. The residue chromatographed on silica gel (10% MeOH/CHCl₃) to give 14-13a as a white solid. p ¹H NMR (400 MHz, CDCl₃): δ 9.08 (s, 1H), 8.66 (s, 2H), 7.63–7.59 (m, 1H), 6.45–6.40 (m, 2H), 3.88–3.82 (m, 1H), 3.17–3.11 (m, 1H), 2.88 (s, 3H), 2.75–2.55 (m, 8H), 1.88–1.70 (m, 3H), 1.61–1.54 (m, 1H).

Enantiomer 14-13b was obtained from 14-9b utilizing the same methods described for the preparation of 14-13a. Its 400 MHz NMR spectrum in CDCl₃ was identical to that of its enantiomer 14-13a.

Scheme 15

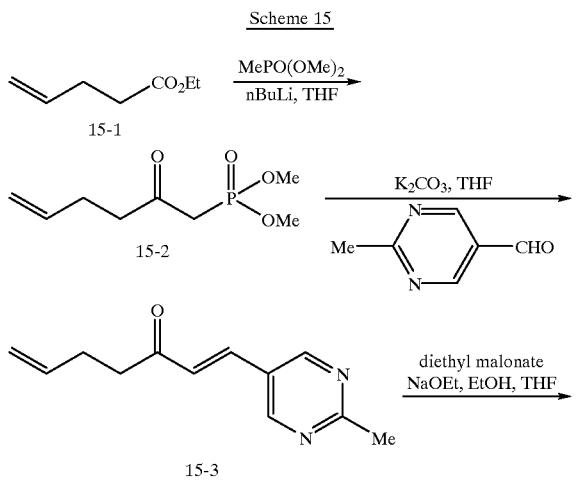

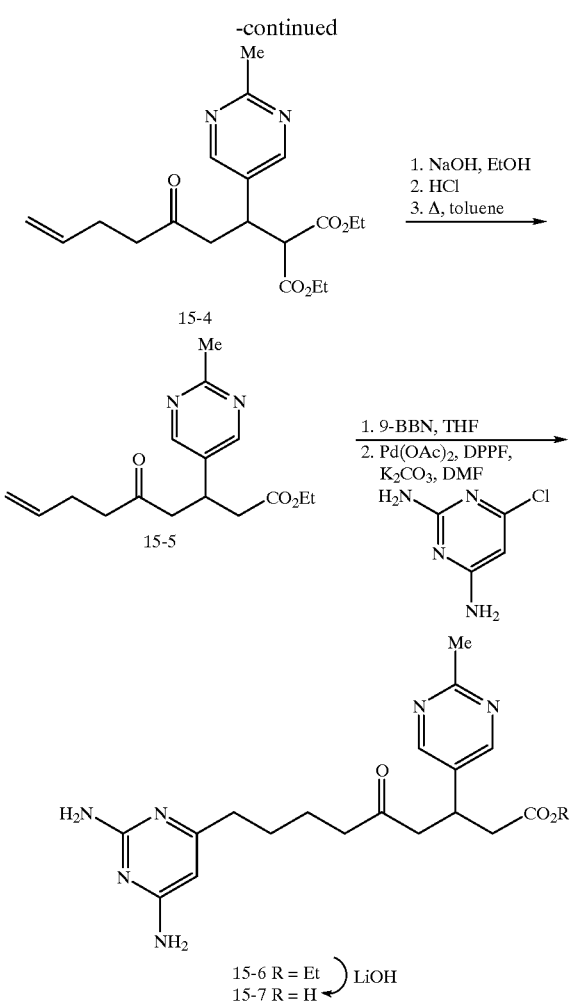

EXAMPLE 21

9-(2,4-Diaminopyrimidin-6-yl)-3-(2-methyl-pyrimidin-5-yl)-5-oxo-nonanoic acid (15-7)

Step A: 1-Dimethylphosphonate-2-oxo-hex-5-ene (15-2)

Dimethyl methylphosphonate (20.3 g, 164 mmol) in THF (250 mL) at −78° C. was treated with n-butyllithium (1.6 M in hexanes; 102 mL, 164 mmol) dropwise over 1 hour. To this was added ethyl 4-pentenoate (7 g, 54.6 mmol) in THF (25 mL) over 30 minutes and the solution stirred a further 30 minutes at −78° C. before being quenched with saturated NH₄Cl.

The mixture was partitioned between water and EtOAc. After extraction with EtOAc (4×), the organic layers were washed with water then brine, dried (MgSO₄) and filtered through celite. Concentration in vacuo afforded the title compound 15-2 as an oil which was used as such.

¹H NMR (300 Mz, CDCl₃) δ 5.8 (m, 1H), 5.0 (m, 2H), 3.81 (s, 3H), 3.77 (s, 3H), 3.10 (d, 2H), 2.74 (m, 2H), 2.35 (m, 2H) ppm.

Step B: 1-(2-Methylpyrimidin-5-yl)-3-oxo-hepta-1,6-diene (15-3)

The phosphonate 15-2 (10 g, 49 mmol), 2-methyl-pyrimidin-5-yl-carbaldehyde (J. Heterocyclic Chem.; 1991, 28, 1281; 5 g, 41 mmol) and K₂CO₃ (6.22 g, 45 mmol) in THF (100 mL) was stirred at room temperature for 16 hours then at 50° C. for 2 hours. The mixture was partitioned between water and EtOAc. After extraction with EtOAc, the organic layers were washed with water then brine, dried (MgSO₄) and filtered through celite. Concentration in vacuo afforded an orange solid. Purification by silica gel chromatography (hexane:EtOAc 1:1 then 1:2) yielded the title compound 15-3 as a white solid.

¹H NMR (300 MHz, CDCl₃) δ 8.8 (s, 2H), 7.5 (d, 1H), 6.84 (d, 1H), 5.88 (m, 1H), 5.1 (m, 2H), 2.8 (m, 2H), 2.79 (s, 3H), 2.45 (m, 2H) ppm.

Step C: 2-(Carboethoxy)-3-(2-methylpyrimidin-5-yl)-5-oxo-non-8-enoic acid ethyl ester (15-4)

The enone 15-3 (5.73 g, 28.4 mmol) was dissolved in TBF (200 mL) and EtOH (80 mL) at room temperature. To this was added diethyl malonate (6.46 mL, 42.5 mmol) and NaOEt (1 mL, 2.8 mmol) and the mixture stirred for 1.5 hours. The solution was partitioned between saturated NaHCO₃ solution and EtOAc, washed with water, brine, dried (MgSO₄) and concentrated in vacuo. The residue was purified by silica gel chromatography (eluting with EtOAc) to give the diester 15-4 as an oil.

¹H NMR (300 MHz, CDCl₃) δ 8.57 (s, 2H), 5.72 (m, 1H), 4.95 (m, 2H), 4.2 (m, 2H), 4.05 (q, 2H), 3.95 (m, 1H), 3.72 (d, 1H), 3.04 (dd, 1H), 2.96 (dd, 1H), 2.69 (s, 3H), 2.42 (m, 2H), 2.25 (m, 2H), 1.26 (t, 3H), 1.10 (t, 3H) ppm.

Step D: 3-(2-Methyl-pyrimidin-5-yl)-5-oxo-non-8-enoic acid ethyl ester (15-5)

The diester 15-4 (11.2 g, 31.1 mmol) was dissolved in EtOH (100 mL) at room temperature. To this was added 1N NaOH (31.1 mL, 31.1 mmol), the mixture stirred at 40° C. for 2 hours then overnight at room temperature. The mixture was concentrated in vacuo, dissolved in toluene (100 mL) and heated at reflux for 5 hours. After removal of the solvent, the residue was partitioned between water and CHCl₃ washed with brine, dried (MgSO₄) and concentrated in vacuo. The residue was purified by silica gel chromatography (eluting with EtOAc) to give the ester 15-5 as an oil.

¹H NMR (300 MHz, CDCl₁₃) δ 8.55 (s, 2H), 5.73 (m, 1H), 4.95 (m, 2H), 4.17 (q, 2H), 3.68 (m, 1H), 2.9 (dd, 1H), 2.82 (dd, 1H), 2.74 (dd, 1H), 2.7 (s, 3H), 2.64 (dd, 1H), 2.42 (m, 2H), 2.25 (m, 2H), 1.18 (t, 3H) ppm Step E: 9-(2,4-Diaminopyrimidin-6-yl)-3-(2-methyl-pyrimidin-5-yl)-5-oxo-nonanoic acid ethyl ester (15-6)

The ester 15-5 (400 mg, 1.38 mmol) was treated with 9-BBN (8.28 mL, 4.14 mmol; 0.5M in TBF) at room temperature for 16 hours. To this solution was added Pd(OAc)₂ (31 mg, 0.14 mmol), 6-chloro-2,4-diaminopyrimidine (219 mg, 1.52 mmol), K₂CO₃ (381 mg, 2.75 mmol), 1,1'-bis(diphenylphosphino)-ferrocene (76 mg, 0.14 mmol) and DMF (15 mL). The mixture was degassed with argon for 10 minutes then heated to 80° C. for 24 hours. The reaction mixture was cooled and stirred with ethanolarnine (5 mL) for 2 hours. The mixture was partitioned between 1N HCl and EtOAc. The aqueous layer was made basic with K₂CO₃ and extracted with EtOAc (5×). The organic layers were washed with brine, dried (MgSO₄) and concentrated. Purification by silica gel chromatography (20% MeOH in CHCl₃) afforded the title compound 15-6 as an oil.

Mass spectrum: calculated for C₂₀H₂₉N₆O₃(M+H) is 401.2; found 401.1.

Step F: 9-(2,4-Diaminopyrimidin-6-yl)-3-(2-methyl-pyrimidin-5-yl)-5-oxo-nonanoic acid (15-7)

The ester 15-6 (20 mg, 0.05 mmol) in THF (10 mL) and water (10 mL) was treated with 1 N LiOH (1.0 mL, 1.0 mmol). After stirring at room temperature for 1 hour, the solution was concentrated to 5 mL and purified by reverse phase HPLC (preppak C-18 column; water/acetonitrile/ 0.1% TFA gradient). After lyophilization, the title compound 15-7 (TFA salt) was obtained as a white powder.

¹H NMR (300 MHz, CD₃OD) δ 8.66 (s, 2H), 5.90 (s, 1H), 3.61 (m, 1H), 5.1 (m, 1H), 5.1 (m, 1H), 3.00 (d, 2H), 2.6–2.8 (m, 2H), 2.64 (s, 3H), 2.4–2.6 (m, 2H), 1.5 (m, 4H) ppm; Mass spectrum: exact mass calculated for C₁₈H₂₄N₆O₃ (M+H) is 373.1983; found 373.1974.

Scheme 16

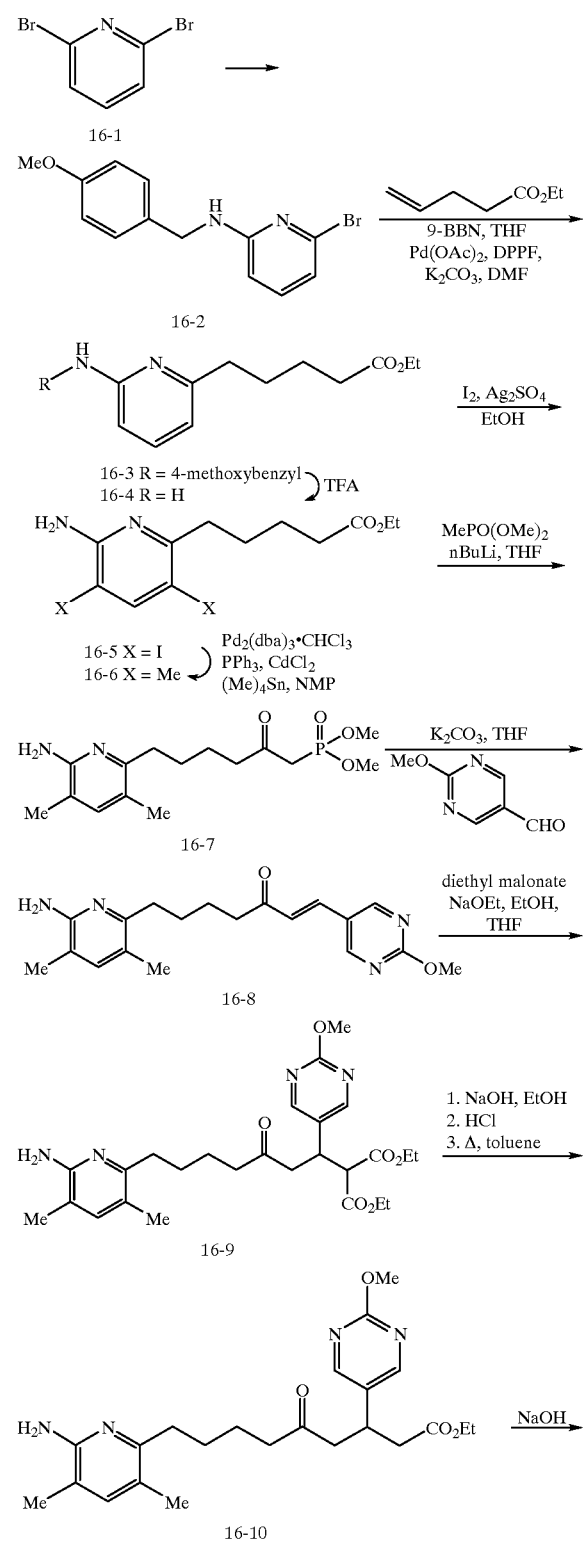

-continued

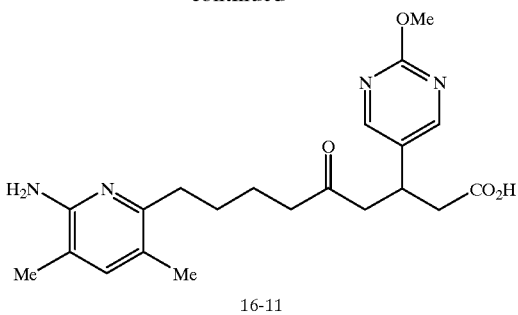

16-11

EXAMPLE 22

9-(2-Amino-3,5-dimethylpyridin-6-yl)-3-(2-methoxypyrimidin-5-yl)-5-oxo-nonanoic acid (16-11)

Step A: 2-Bromo-6-(4-methoxybenzylamino)pyridine (16-2)

A mixture of 2,6-dibromopyridine 16-1 (15 g, 70 mmol), 4-methoxybenzylamine (25 mL, 191 mmol) and butanol (25 mL) was heated at 100° C. for 6 days. After cooling, EtOAc was added, the solids removed by filtration and the solution concentrated in vacuo. Purification of the residue by silica gel chromatography (Hexane:EtOAc 4:1) afforded the title compound 16-2 as a white solid.

$^1$H NMR (300 MHz, CDCl$_3$) δ 7.25 (d, 2H), 7.21 (t, 1H), 6.88 (d, 2H), 6.73 (d, 1H), 6.26 (d, 1H), 5.02 (bt, 1H), 4.38 (d, 2H), 3.79 (s, 3H) ppm.

Step B: 5-[2-(4-methoxybenzylamino)pyridin-6-yl]pentanoic acid ethyl ester (16-3)

Ethyl 4-pentenoate (8.95 g, 69.8 mmol) was treated with 9-BBN (167 mL, 83.7 mmol; 0.5M in THF) at 0° C. then warmed to room temperature and stirred for 16 hours. To this solution was added Pd(OAc)2 (1.57 g, 6.98 mmol), pyridine 16-2 (18.4 g, 62.8 mmol), K$_2$CO$_3$ (14.4 g, 105 mmol), 1,1'-bis(diphenylphosphino)-ferrocene (3.87 g, 6.98 mmol) and DMF (200 mL). The mixture was degassed with argon for 10 minutes then heated to 80° C. for 24 hours. The reaction mixture was cooled and stirred with ethanolamine (20 mL) for 2 hours. The mixture was partitioned between water and EtOAc, extracted with EtOAc (3×), washed with water (3×), then brine, dried (MgSO$_4$) and concentrated. Purification by silica gel chromatography (hexane:EtOAc 3:2) afforded the title compound 16-3 as an oil.

$^1$H NMR (300 MHz, CDCl$_3$) δ 7.32 (t, 1H), 7.28 (d, 2H), 6.88 (d, 2H), 6.45 (d, 1H), 6.19 (d, 1H), 4.89 (bt, 1H), 4.38 (d, 2H), 4.12 (q, 2H), 3.80 (s, 3H), 2.63 (t, 2H), 2.23 (t, 2H), 1.6 (m, 4H), 1.26 (t, 3H) ppm.

Step C: 5-(2-Aminopyridin-6-yl)pentanoic acid ethyl ester (16-4)

The ester 16-3 (5.7 g) in TFA (75 mL) was heated at 60° C. for 2 hours then cooled and the excess TFA removed in vacuo. The residue was diluted with water, made basic with NaHCO$_3$ and extracted with ether (3×). After washing the ether layer with saturated NaHCO$_3$ then brine, it was dried (Na$_2$SO$_4$) and concentrated to give a viscous oil. Purification by silica gel chromatography (hexane:EtOAc 3:7) afforded the title compound 16-4 as an oil.

$^1$H NMR (300 MHz, CDCl$_3$) δ 7.34 (t, 1H), 6.50 (d, 1H), 6.32 (d, 1H), 4.35 (bs, 2H), 4.12 (q, 2H), 2.61 (t, 2H), 2.33 (t, 2H), 1.7 (m, 4H), 1.25 (t, 3H) ppm.

Step D: 5-(2-Amino-3,5-diiodopyridin-6-yl)pentanoic acid ethyl ester (16-5)

To a solution of the ester 16-4 (1.11 g, 5 mmol) in EtOH (20 mL) was added Ag$_2$SO$_4$ (1.87 g, 6 mmol) and I$_2$ (1.52 g, 6 mmol) and the mixture was stirred for 1 hour. The mixture was diluted with CH$_2$Cl$_2$ (50 mL), filtered and concentrated. The residue was dissolved in EtOAc, washed with aqueous sodium thiosulfate followed by brine, dried (Na$_2$SO$_4$) and the solvent removed. Purification by silica gel chromatography (hexane:EtOAc 4:1) afforded the title compound 16-5 as a solid.

$^1$H NMR (300 MHz, CDCl$_3$) δ 8.09 (s, 1H), 4.86 (bs, 2H), 4.12 (q, 2H), 2.75 (t, 2H), 2.35 (t, 2H), 1.7 (m, 4H), 1.25 (t, 3H) ppm.

Step E: 5-(2-Amino-3,5-dimethylpyridin-6-yl)pentanoic acid ethyl ester (16-6)

A mixture of the ester 16-5 (1.44 g, 3 mmol), Pd(dba)$_3$.CHCl$_3$ (0.124 g, 0.12 mmol), CdCl$_2$ (0.55 g, 3 mmol), Ph$_3$P (0.226 g, 0.86 mmol), (CH$_3$)$_4$Sn (0.873 mL, 6 mmol) and NMP (10 mL) in a pressure tube was degassed with argon and heated to 100° C. for 20 hours. The mixture was cooled, diluted with water (100 mL) and filtered through celite. After removing the solvent in vacuo, the residue was dilited with 10% aqueous KHSO$_4$, extracted with EtOAc and the aqueous layers then basified with K$_2$CO$_3$. Extracted with EtOAc (3×), washed with brine, dried (Na$_2$SO$_4$) and the solvent removed. Purification by silica gel chromatography (3% MeOH in CHCl$_3$) afforded the title compound 16-6 as an oil.

$^1$H NMR (300 MHz, CDCl$_3$) δ 7.01 (s, 1H), 4.17 (bs, 2H), 4.12 (q, 2H), 2.85 (s, 6H), 2.61 (t, 2H), 2.33 (t, 2H), 1.7 (m, 4H), 1.25 (t, 3H) ppm.

Step F: 6-(2-Amino-3,5-dimethylpyridin-6-yl)-1-dimethylphosphonate-hexan-2-one (16-7)

Following the procedure for the synthesis of 1-6 but using 16-6 as starting material, the title compound 16-7 was prepared as an oil.

$^1$H NMR (300 MHz, CDCl$_3$) δ 7.01 (s, 1H), 4.26 (bs, 2H), 3.80 (s, 3H), 3.76 (s, 3H), 3.10 (d, 2H), 2.62 (m, 4H), 2.14 (s, 3H), 2.07 (s, 3H), 1.64 (m, 4H) ppm.

Step G: Step 7-(2-Amino-3,5-dimethylpyridin-6-yl)-1-(2-methoxypyrimidin-5-yl)-3-oxo-hept-1-ene (16-8)

Following the procedure for the synthesis of 1-7, but using 16-7 and 2-methoxypyrimidin-5-yl-carboxaldehyde (Gupton et al., *J. Heterocyclic Chem.*, 1991, 28, 1281) as starting material, the title compound 16-8 was obtained as a solid.

$^1$H NMR (300 MHz, CDCl$_3$) δ 8.69 (s, 2H), 7.44 (d, 1H), 7.02 (s, 1H), 6.74 (d, 1H), 4.18 (bs, 2H), 4.07 (s, 3H), 2.70 (t, 2H), 2.64 (t, 2H), 2.16 (s, 3H), 2.07 (s, 3H), 1.7 (m, 4H) ppm.

Step H: 9-(2-Amino-3,5-dimethylpyridin-6-yl)-2-(carboethoxy)-3-(2-methoxypyrimidin-5-yl)-5-oxo-nonanoic acid ethyl ester (16-9)

Following the procedure for the synthesis of 1-8, but using 16-8 as starting material, the title compound 16-9 was obtained as an oil.

1HNMR (300 MHz, CDCl$_3$) δ 8.44 (s, 2H), 7.01 (s, 1H), 4.2 (m, 6H), 4.04 (q, 2H), 3.97 (s, 3H), 3.71 (m, 1H), 3.69 (d, 2H), 2.97 (dd, 1H), 2.87 (dd, 1H), 2.54 (m, 2H), 2.36 (m, 2H), 2.11 (s, 3H), 2.06 (s, 3H), 1.55 (m, 4H), 1.25 (t, 3H), 1.11 (t, 3) ppm Step I: 9-(2-Amino-3,5-dimethylpyridin-6-yl)-3-(2-methoxypyrimidin-5-yl)-5-oxo-nonanoic acid ethyl ester (16-10)

Following the procedure for the synthesis of 1-10, but using 16-9 as starting material, the title compound 16-10 was obtained as an oil.

$^1$H NMR (300 MHz, CDCl$_3$) δ 8.41 (s, 2H), 7.02 (s, 1H), 4.26 (bs, 2H), 4.05 (q, 2H), 3.98 (s, 3H), 3.65 (m, 1H), 2.87

(dd, 1H), 2.77 (dd, 1H), 2.69 (dd, 1H), 2.56 (m, 3H), 2.4 (m, 2H), 2.12 (s, 3H), 2.07 (s, 3H), 1.58 (m, 4H), 1.18 (t, 3H) ppm.

Step J: 9-(2-Amino-3,5-dimethylpyridin-6-yl)-3-(2-methoxypyrimidin-5-yl)-5-oxo-nonanoic acid (16-11)

The ester 16-10 (0.12 g, 0.28 mmol), 1N NaOH (1 mL, 1 mmol) and EtOH (4 mL) were stirred at room temperature for 16 hours. 1N HCl (1 mL) was added and the solvent was removed in vacuo to give a viscous residue. Purification on silica gel eluting with EtOAc:EtOH:conc. $NH_4OH:H_2O$ 15:10:1:1 gave an oil which was taken up in water and lyophilized to give the title compound 16-11 as a powder.

1H NMR (300 MHz, $CDCl_3OD$) δ 8.50 (s, 2H), 7.51 (s, 1H), 3.95 (s, 3H), 3.70 (m, 1H), 3.05 (dd, 1H), 2.78 (dd, 1H), 2.65 (m, 5H), 2.47 (dd, 1H), 2.17 (s, 3H), 2.15 (s, 3H), 1.68 (m, 4H) ppm. Mass spectrum: calculated for $C_{22}H_{31}N_4O_4$ (M+H) is 401.5; found 401.1.

Scheme 17

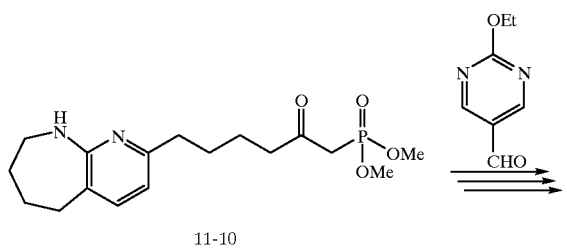

11-10

-continued

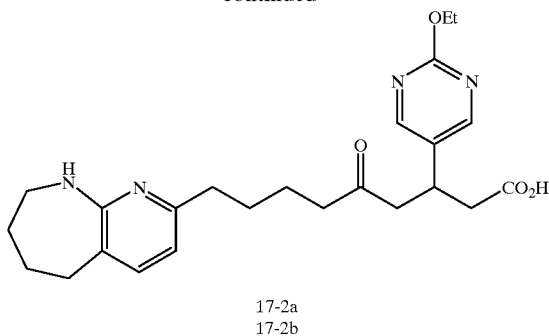

17-2a
17-2b

EXAMPLE 23
3(R) and 3(S)-(2-Ethoxy-pyrimidin-5-yl)-5-oxo-9-(6,7,8,9-tetrahydro-5H-pyrido2,3-b]azepin-2-yl)-nonanoic Acid (17-2a and 17-2b)

Utilizing the procedures for the conversion of 1-6 into 1-11a and 1-11b, 11-10 and 2-ethoxy-pyrimidine-5-carbaldehyde were converted into 17-2a and 17-2b. Resolution of the enantiomers was carried out by chiral chromatography of the keto diester intermediate corresponding to 1-8.

TLC $R_f$=0.24 (silica, 10:10:1:1 EtOAc/EtOH/$NH_4OH$/$H_2O$). $^1H$ NMR (400 MHz, $CD_3OD$) δ 8.48 (s, 2H), 7.43 (d, 1H, J=7 Hz), 6.55 (d, 1H, J=7 Hz), 4.38 (q 2H, J=7 Hz), 3.63 (m, 1H), 2.98 (m, 1H), 2.79 (m, 3H), 2.55 (m, 6H), 1.84 (m, 4H), 1.57 (m, 4H), 1.38 (t, 3H, J=7 Hz).

The following additional but non-limiting examples were prepared using the procedures detailed in the Examples and Schemes above and are accompanied by their mass spectral characterization data:

| Compound No. | Compound Name | Mass Spectrum* |
|---|---|---|
| (1) | 3(R) and 3(S)-(pyrazin-2-yl)-5-oxo-9-(5,6,7,8-tetrahydro-[1,8]naphthyridin-2-yl)-nonanoic acid | 383 |
| | 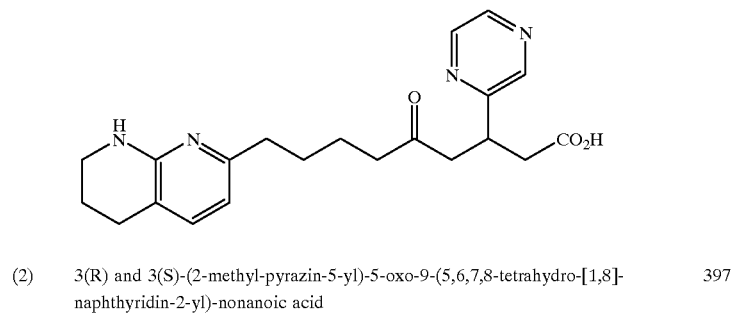 | |
| (2) | 3(R) and 3(S)-(2-methyl-pyrazin-5-yl)-5-oxo-9-(5,6,7,8-tetrahydro-[1,8]-naphthyridin-2-yl)-nonanoic acid | 397 |
| | 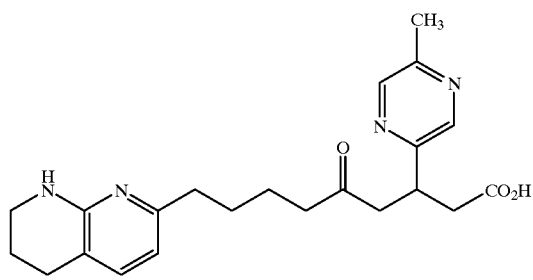 | |

-continued

| Compound No. | Compound Name | Mass Spectrum* |
|---|---|---|
| (3) | 3(R) and 3(S)-(6-methoxy-pyridazin-3-yl)-5-oxo-9-(5,6,7,8-tetrahydro-[1,8]-naphthyridin-2-yl)-nonanoic acid | 413 |

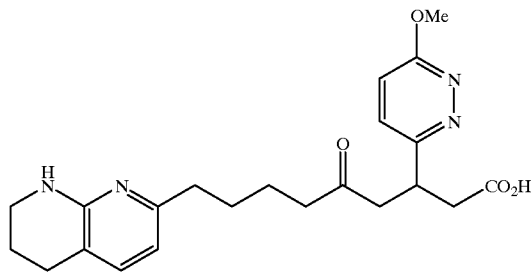

| | | |
|---|---|---|
| (4) | 3(R) and 3(S)-(2-methylamino-pyrimidin-5-yl)-5-oxo-9-(5,6,7,8-tetrahydro-[1,8]naphthyridin-2-yl)-nonanoic acid | 412 |

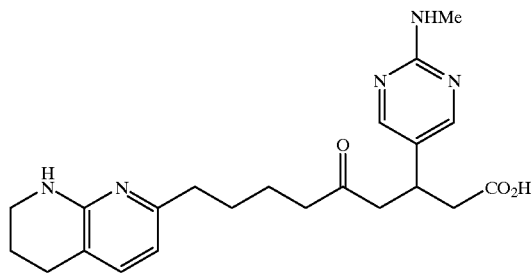

| | | |
|---|---|---|
| (5) | 3(R) and 3(S)-(3,4-dihydro-2H-1,4-dioxa-5-aza-naphthalen-7-yl)-5-oxo-9-(5,6,7,8-tetrahydro-[1,8]naphthyridin-2-yl)-nonanoic acid | 440 |

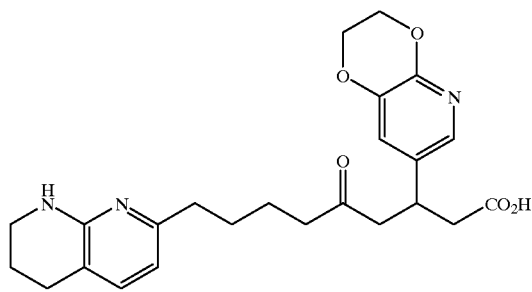

| | | |
|---|---|---|
| (6) | 3(R) and 3(S)-(2-methyl-pyrimidin-5-yl)-5-oxo-9-[6(R or S)-methyl-5,6,7,8-tetrahydro-[1,8]naphthyridin-2-yl]-nonanoic acid | 411 |

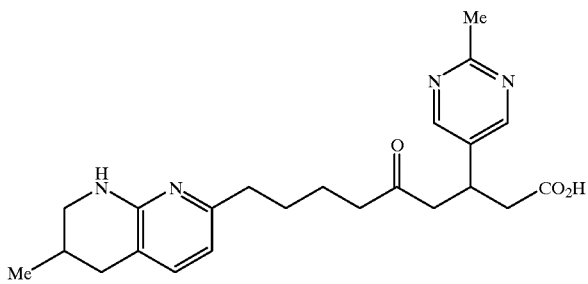

-continued
| Compound No. | Compound Name | Mass Spectrum* |
|---|---|---|
| (7) | 3(R) and 3(S)-(benzofuran-6-yl)-5-oxo-9-(5,6,7,8-tetrahydro-[1,8]-naphthyridin-2-yl)-nonanoic acid | 421 |
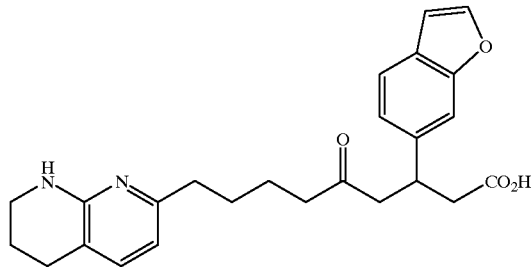
| (8) | 3(R) and 3(S)-(5-methoxy-pyridin-3-yl)-5-oxo-9-(5,6,7,8-tetrahydro-[1,8]-naphthyridin-2-yl)-nonanoic acid | 412 |
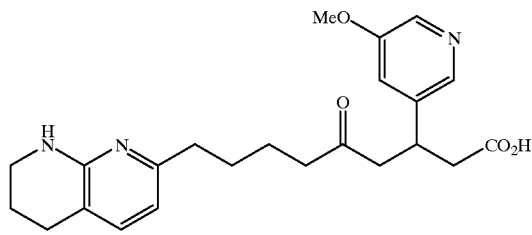
| (9) | 3(R) and 3(S)-(2-dimethylamino-pyrimidin-5-yl)-5-oxo-9-(5,6,7,8-tetrahydro-[1,8]naphthyridin-2-yl)-nonanoic acid | 426 |
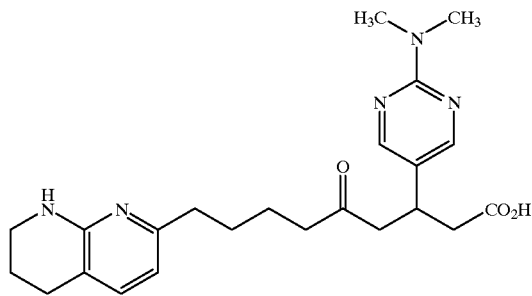
| (10) | 3(R) and 3(S)-(2-methyl-pyrimidin-5-yl)-5-oxo-9-(3-vinyl-5,6,7,8-tetrahydro-[1,8]naphthyridin-2-yl)-nonanoic acid | 423 |
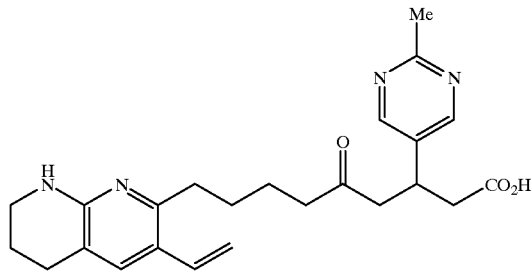

-continued

| Compound No. | Compound Name | Mass Spectrum* |
|---|---|---|
| (11) | 3(R) and 3(S)-(pyrimidin-5-yl)-5-oxo-9-(3-cyclopropyl-5,6,7,8-tetrahydro-[1,8]naphthyridin-2-yl)-nonanoic acid | 423 |

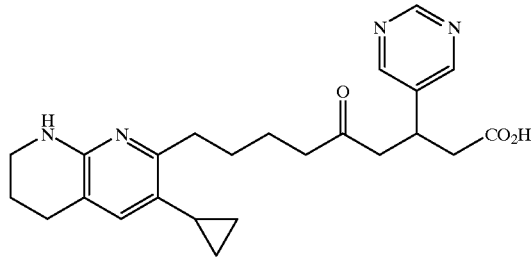

| | | |
|---|---|---|
| (12) | 3(R) and 3(S)-(2-methyl-pyrimidin-5-yl)-5-oxo-9-(3-chloro-5,6,7,8-tetrahydro-[1,8]naphthyridin-2-yl)-nonanoic acid | 431 |

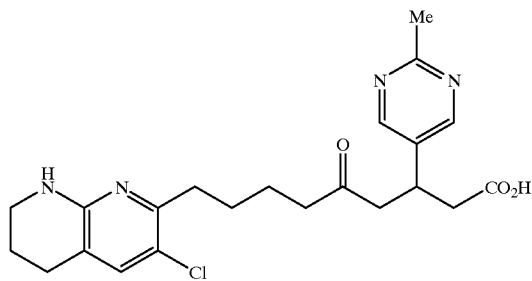

| | | |
|---|---|---|
| (13) | 3(R) and 3(S)-(2-methyl-pyrimidin-5-yl)-5-oxo-9-(3-bromo-5,6,7,8-tetrahydro-[1,8]naphthyridin-2-yl)-nonanoic acid | 473 |

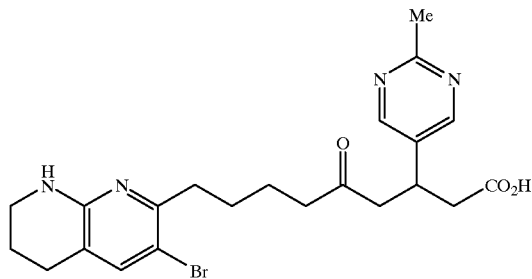

| | | |
|---|---|---|
| (14) | 3(R) and 3(S)-(2-methoxy-pyrimidin-5-yl)-5-oxo-9-(3-methyl-5,6,7,8-tetrahydro-[1,8]naphthyridin-2-yl)-nonanoic acid bis-trifluoroacetate salt | 428 |

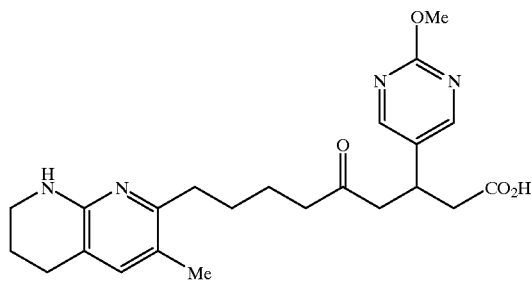

-continued

| Compound No. | Compound Name | Mass Spectrum* |
|---|---|---|
| (15) | 3(R) and 3(S)-(quinolin-3-yl)-5-oxo-9-(3-methyl-5,6,7,8-tetrahydro[1,8]-naphthyridin-2-yl)-nonanoic acid | 446 |
| (16) | 3(R) and 3(S)-(2-methyl-pyrimidin-5-yl)-5-oxo-7,7-dimethyl-9-(5,6,7,8-tetrahydro-[1,8]naphthyridin-2-yl)-nonanoic acid | 425 |
| (17) | 3(R) and 3(S)-(2-ethoxy-pyrimidin-5-yl)-5-oxo-9-(3-cyclopropyl-5,6,7,8-tetrahydro-[1,8]naphthyridin-2-yl)-nonanoic acid | 467 |
| (18) | 3(R) and 3(S)-(6-methoxy-pyridin-3-yl)-5-oxo-9-(3-cyclopropyl-5,6,7,8-tetrahydro-[1,8]naphthyridin-2-yl)-nonanoic acid | 452 |

*m/e, M⁺ or (M + 1)⁺

SCHEME A
Synthesis of Radioligand for SPAV3 Assay
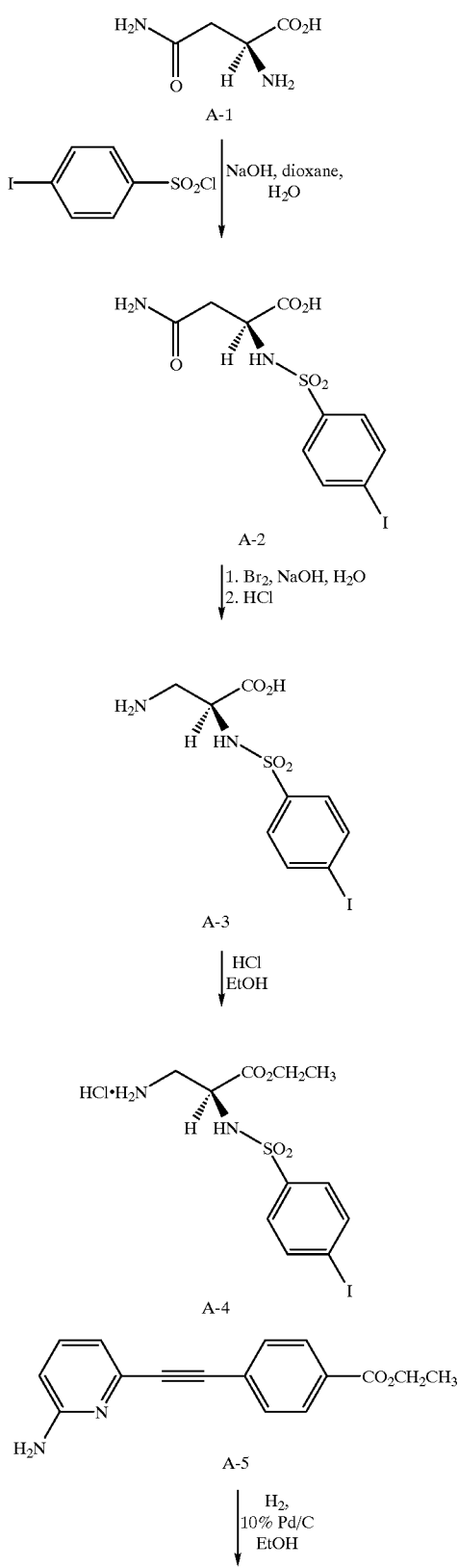
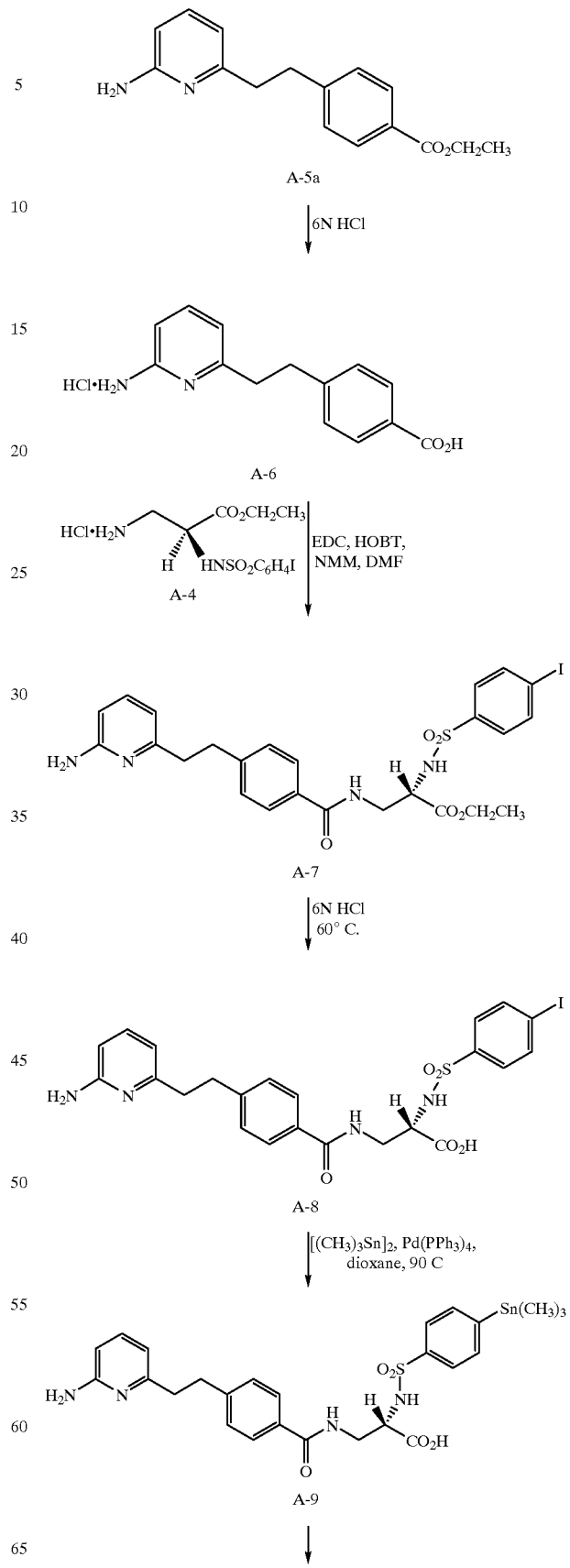

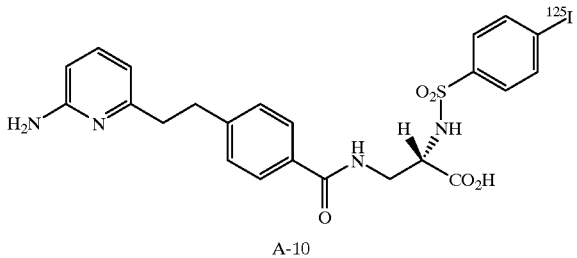

A-10

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and $H_2O$ (30 ml) at 0° C. was added pipsyl chloride (10.34 g, 34.2 mmol). After ~5 minutes, NaOH (1.49, 37.2 mmol) dissolved in 15 ml $H_2O$, was added followed by the removal of the cooling bath. After 2.0 h, the reaction mixture was concentrated. The residue was dissolved in $H_2O$ (300 ml) and then washed with EtOAc. The aqueous portion was cooled to 0° C. and then acidified with concentrated HCl. The solid was collected and then washed with $Et_2O$ to provide acid A-2 as a white solid.

$^1$H NMR (300 MHz, $D_2O$) δ 7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and $H_2O$ (40 ml) at 0° C. was added $Br_2$ (1.30 ml, 24.9 mmol) dropwise over a ten minute period. After ~5 minutes, acid A-2 (9.9 g, 24.9 mmol), NaOH (2.00 g, 49.8 mmol) and $H_2O$ (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, $D_2O$) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, $CD_3OD$) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester A-5a as a brown oil.

TLC $R_f$=0.23 (silica, 40% EtOAc/hexanes). $^1$H NMR (300 MHz, $CDCl_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, $CD_3OD$) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-βalanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. $NaHCO_3$, brine, dried ($MgSO_4$) and concentrated. Flash chromatography (silica, EtOAc then 5% isopropanol/EtOAc) provided amide A-7 as a white solid.

TLC $R_f$=0.4 (silica, 10% isopropanol/EtOAc).

$^1$H NMR (300 MHz, $CD_3OD$) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid A-8 as a white solid.

TLC $R_f$=0.45 (silica, 20:20:1:1 EtOAc/EtOH/$NH_4OH$/$H_2O$). $^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m 2H).

4-[2-(2-Aminopyridin-6-yl)ethyl)benzoyl-2(S)-(4-trimethylstannyl-phenylsulfonylamino-β-alanine (A-9)

A solution of iodide A-8 (70 mg, 0.1178 mmol), $[(CH_3)_3Sn]_2$ (49 μl, 0.2356 mmol), $Pd(PPh_3)_4$ (5 mg) and dioxane (7 ml) was heated to 90° C. After 2 h, the reaction was concentrated and then purified by preparative HPLC (Delta-Pak $C_{18}$ 15 μM 100A°, 40×100 mm; 95:5 then 5:95 $H_2O$/$CH_3CN$) to provide the trifluoroacetate salt. The salt was suspended in $H_2O$ (10 ml), treated with $NH_4OH$ (5 drops) and then lyophilized to provide amide A-9 as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

diluted with ethyl acetate, washed with water, saturated aqueous NaHCO$_3$, and brine, dried over MgSO$_4$, and concentrated. The residue was chromatographed on silica gel (70:25:5 CHCl$_3$/EtOAc/MeOH) to give B-2 as a white solid.

TLC R$_f$=0.22 (silica, 70:25:5 CHCl$_3$/EtOAc/MeOH). $^1$H NMR (300 MHz, CDCl$_3$) δ 7.79 (d, 2H, J=8 Hz), 7.63 (d, 2H, J=8 Hz), 7.54 (d, 2H, J=8 Hz), 7.27 (d, 2H, J=8 Hz), 7.04 (d, 1H, J=7 Hz), 6.60 (m, 1H), 6.29 (d, 1H J=7 Hz), 4.83 (br s, 1H), 4.09 (m, 3H), 3.84 (m, 1H), 3.68 (m, 1H), 3.42 (m, 2H), 3.01 (m, 4H), 2.86 (m, 4H), 2.69 (t, 2H, J=6 Hz), 1.88 (m, 2H).

SCHEME B
Synthesis of Radioligand for SPAV5 Assay

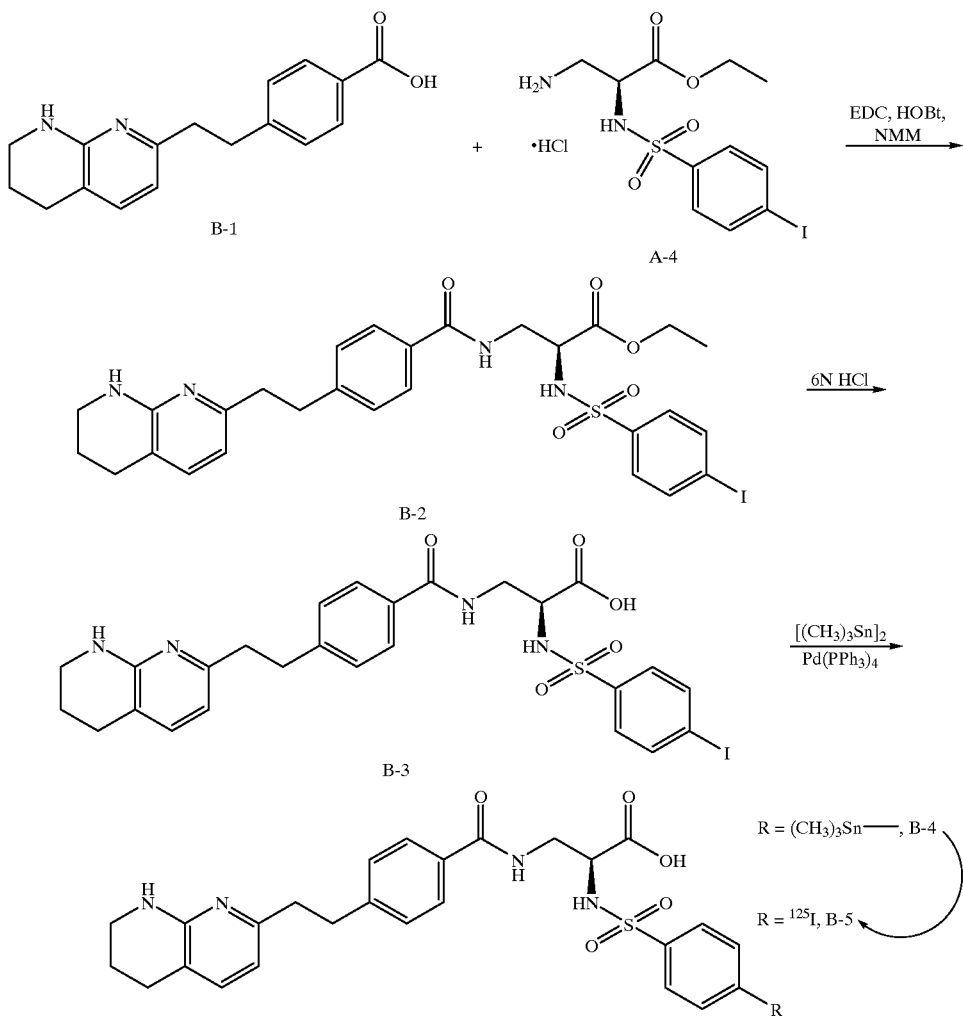

2(S)-(4-Iodo-benzenesulfonylamino)-3-{4-[2-(5,6,7, 8-tetrahydro-[1,8]naphthyridin-2-yl)-ethyl]-benzoylamino}-propionic Acid Ethyl Ester (B-2)

A mixture of B-1 (0.23 g, 0.72 mmol; for preparation see U.S. Pat. No. 5,741,796), A-4 (0.343 g, 0.792 mmol), EDC (0.179 g, 0.93 mmol), HOBT (0.126 g, 0.93 mmol), NMM (0.316 mL, 2.86 mmol) in acetonitrile (3 mL) and DMF (3 mL) was stirred for 2 hours at ambient temperature then 2(S)-(4-Iodo-benzenesulfonylamino)-3-{4-[2-(5,6,7, 8-tetrahydro-[1,8]naphthyridin-2-yl)-ethyl]-benzoylamino}-propionic Acid (B-3)

A mixture of B-2 (0.38 g, 0.573 mmol) and 6N HCl (50 mL) was stirred for 14 hours at 60° C. After cooling to room temperature, the mixture was concentrated, and the residue chromatographed on silica gel (25:10:1:1 to 15:10:1:1 EtOAc/EtOH/NH$_4$OH/H$_2$O) to give B-3 as a white solid.

TLC $R_f$=0.43 (silica, 10:10:1:1 EtOAc/EtOH/NH$_4$OH/H$_2$O). $^1$H NMR (300 MHz, DMSO-d$_6$) δ 8.42 (m, 1H), 7.79 (d, 2H, J=8 Hz), 7.63 (d, 2H, J=8 Hz), 7.44 (d, 2H, J=8 Hz), 7.27 (d, 2H, J=8 Hz), 7.10 (d, 1H, J=7 Hz), 6.58 (br s, 1H), 6.32 (d, 1H, J=7 Hz), 3.96 (m, 1H), 3.51 (m, 1H), 3.30 (m, 5H), 2.96 (m, 2H), 2.78 (m, 2H), 2.62 (m, 2H), 1.77 (m, 2H). HRMS: For $C_{26}H_{27}IN_4O_5S$, expected 635.0818, found 635.0831.

3-{4-[2-(5,6,7,8-Tetrahydro-[1,8]naphthyridin-2-yl)-ethyl]-benzoylamino}-2(S)-(4-trimethylstannanyl-benzenesulfonylamino)-propionic Acid (B-4)

A mixture of B-3 (0.10 g, 0.16 mmol), hexamethyldistannane (0.065 mL, 0.32 mmol), Pd(PPh$_3$)$_4$, and dioxane (10 mL) was stirred for one hour at 90° C. After cooling to room temperature, the mixture was concentrated, and the residue chromatographed on silica gel (50:10: 1:1 to 25:10:1:1 EtOAc/EtOH/NH$_4$OH/H$_2$O) to give B-4 as a white solid.

TLC $R_f$=0.48 (silica, 15:10:1:1 EtOAc/EtOH/NH$_4$OH/H$_2$O). $^1$H NMR (300 MHz, DMSO-d$_6$) δ 8.38 (m, 1H), 8.14 (m, 1H), 7.63 (m, 4H), 7.28 (d, 2H, J=8 Hz), 7.08 (d, 1H, J=7 Hz), 6.50 (br s, 1H), 6.28 (d, 1H, J=7 Hz), 3.96 (m, 1H), 3.48 (m, 1H), 3.31 (m, 5H), 2.96 (m, 2H), 2.78 (m, 2H), 2.62 (m, 2H), 1.77 (m, 2H), 0.28 (s, 9H). High resolution mass spectrum: For $C_{29}H_{36}N_4O_5SSn$, expected 665.1533 ($^{112}$Sn) and 673.1507 ($^{120}$Sn), found 665.1510 and 673.1505.

2(S)-(4-$^{125}$Iodo-benzenesulfonylamino)-3-{4-[2-(5,6,7,8-tetrahydro-[1,8]naphthyridin-2-yl)-ethyl]-benzoylamino}-propionic Acid (B-5)

A stir bar, methanol (0.05 mL) and an iodobead (Pierce) were added to a shipping vial of Na$^{125}$I (10 mCi, Amersham, IMS300) and stirred for five minutes at room temperature. A solution of B-4 (~0.1 mg) in methanol (0.04 mL) was made and a portion (0.02 mL) was added to a mixture of H$_2$SO$_4$ (0.005 mL) in methanol (0.025 mL), and this solution was added immediately to the Na$^{125}$I/iodobead vial. After stirring for two minutes at room temperature, the reaction was quenched with NH$_4$OH (0.04–0.05 mL) and the entire reaction mixture was injected onto the HPLC for purification [Vydac peptide-protein C-18 column, 4.6×250 mm, linear gradient of 10% acetonitrile:H$_2$O (0.1% TFA) to 90% acetonitrile:H$_2$O (0.1% TFA) over 20 minutes, 1 ml/min]. The retention time of B-5 is 16 minutes under these conditions. Fractions containing the majority of the radioactivity were pooled, lyophilized and diluted with ethanol to give approximately 1 mCi of B-5, which coeluted on HPLC analysis with an authentic sample of B-3.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure $α_vβ3$ and $αvβ5$ binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur dialysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in H$_2$O. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7-14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~2×10$^7$ cells/ml). A cell suspension consisting of 5×10$^6$/ml in αMEM containing 5% fetal bovine serum, 10 nM 1,25(OH)$_2$D$_3$, and pencillin-streptomycin is prepared. 200 ml aliquots are added to bovine bone slices (200 mm×6 mm) and incubated for 2 hrs. at 37° C. in a humidified 5% CO$_2$ atmosphere. The medium is removed gently with a micropipettor and fresh medium containing test compounds is added. The cultures are incubated for 48 hrs., and assayed for c-telopeptide (fragments of the a1 chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of H$_2$O, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M NH$_4$OH followed by 2×15 min ultrasonication in H$_2$O. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting IC$_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8: S378 (1993), describes a system for expressing the human integrin $\alpha_v\beta3$. It has been suggested that the integrin stimulates attachment of osteoclasts to bone matrix, since antibodies against the integrin, or RGD-containing molecules, such as echistatin (European Patent 382,451), can effectively block bone resorption.

Reaction Mixture:
1. 175 µl TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 µl).
3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound $\alpha_v\beta3$ were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPAV3 ASSAY

MATERIALS:
1. Wheat germ agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: $\alpha_v\beta3$ was purified from 293 cells overexpressing $\alpha_v\beta3$ (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer PROCEDURE:
1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 µl (40 mg/ml) of pretreated beads were suspended in 97.5 µl of binding buffer and 20 ml of 50-OG buffer. 5 ml (~30 ng/µl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 µl of binding buffer and 25 µl of 50-OG buffer.
3. Reaction
   The following were sequentially added into Optiplate in corresponding wells:
   (i) Receptor/beads mixture (75 µl)
   (ii) 25 µl of each of the following: compound to be tested, binding buffer for total binding or A-8 for non-specific binding (final concentration 1 µM)
   (iii) A-10 in binding buffer (25 µl, final concentration 40 pM)
   (iv) Binding buffer (125 µl)
   (v) Each plate was sealed with plate sealer from PACKARD and incubated overnight with rocking at 4° C.
4. Plates were counted using PACKARD TOPCOUNT
5. % inhibition was calculated as follows:
   A=total counts
   B=nonspecific counts
   C=sample counts
   % inhibition=[{(A−B)−(C−B)}/(A−B)]/(A−B)×100

Representative compounds of the present invention were tested and found to bind to human $\alpha_v\beta3$ integrin. These compounds were generally found to have $IC_{50}$ values less than about 100 nM in the SPAV3 assay.

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1\times10^6$ cells/mL. 50 mL was added to each well of 1.8 cells to yield 50,000 cells/well and 1,25-dihydroxy-vitamin D3 (D3) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing D3 to quadruplicate wells. Compounds were added again after 48 h with fresh medium containing D3. After an additional 48 h., the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

SPAV5 ASSAY

MATERIALS:
1. Wheat germ agglutinin Scintillation Proximity Beads (SPA): Amersham
2. Octylglucopyranoside and Phorbo-12-myristate-13-acetate (PMA): Calbiochem 3. Tris-HCl, NaCl and $CaCl_2$: Fisher
4. Minimum Essential Media (MEM): Gibco/BRL
5. Fetal bovine serum (FBS): Hyclone
6. $MgCl_2$, $MnCl_2$, and Phenylmethylsulfonylfluoride (PMSF): SIGMA
7. Protease inhibitor cocktail tablets: Boehringer Mannheim.
8. Optiplate-96 wells: PACKARD
9. B-5 was used as radiolabeled ligand (specific activity 500–1000 Ci/mmole) and B-3 (2.5 $\mu M$) was used to achieve 100% inhibition.
10. Test compound.
11. HEK293 cells overexpressing $\alpha_v\beta_5$ integrins (Simon et al., J. Biol. Chem. 272, 29380–29389, 1997) are cultured in 150 mm dishes in 10% FBS/MEM media (Gibco/BRL).
12. Lysis buffer: 100 mM octylglucopyranoside, 50 mM Tris, pH 7.5, 100 mM NaCl, 1 mM $CaCl_2$, 1 mM $MgCl_2$, 0.5 mM PMSF and protease inhibitors (1 tablet/50 ml buffer).
13. Binding buffer: 50 mM Tris, pH 7.5, 100 mM NaCl, 1 mM $CaCl_2$ 1 mM $MgCl_2$ and 1 mM $MnCl_2$.
14. 50 mM octylglucopyranoside in binding buffer: 50-OG buffer PROCEDURE:
1. $\alpha_v\beta_5$-cell lysates: HEK 293 cells expressing $\alpha_v\beta_5$ integrins were cultured until confluent. Cells were then starved overnight in media containing 0.5% FBS, followed by treatment with 100 nM PMA for 20 min. Cells were washed 2 times with cold phosphate buffer saline (4° C.) and solubilized in lysis buffer for 30 min on ice. Lysates were clarified using a Beckman JA-20 at 20,000× g. Protein concentration of clarified lysates was determined using a micro BCA kit (Pierce) and stored in aliquots at 80° C.
2. Pretreatment of SPA beads:
    500 mg of lyophilized SPA beads were first washed four times with 200 ml of 50-OG buffer and once with 100 ml of binding buffer, and then resuspended in 12.5 ml of binding buffer.
3. Preparation of SPAV5 binding reaction
    To each assay well, the following were sequentially added into Optiplate plates:
        (i) Binding buffer to make up final volume of 125 $\mu l$ per well.
        (ii) 3 $\mu l$ (120 $\mu g$/well) of pretreated beads diluted with 22 $\mu l$ of 50-OG Buffer
        (iii) 15 $\mu g$ of $\alpha_v\beta_5$-cell lysate proteins.
        (iv) B-5 at 50,000 cpm.
        (v) 25 $\mu l$ of graded concentrations of test compound.
        (vi) Each plate was sealed with plate sealer from PACKARD and incubated overnight with rocking at 4° C.
4. Plates were counted using PACKARD TOPCOUNT microplate scintillation counter.
5. % Inhibition was calculated as follows:
A=total counts (binding of receptor to B-5)
B=nonspecific counts (binding of receptor to B-5 in the presence of 2.5 $\mu M$ cold ligand)
C=counts from receptor binding to test compound
% inhibition =$[\{(A-B)-(C-B)\}/(A-B)]/(A-B)\times 100$
$IC_{50}$ of test compound was calculated as 50% of inhibition.

Representative compounds of the present invention were tested and generally found to have $IC_{50}$ values less than 1 $\mu M$ in the SPAV5 assay.

EXAMPLE OF A PHARMACEUTICAL FORMULATION

As a specific embodiment of an oral composition, 100 mg of any of the compounds of the present invention are formulated with sufficient finely divided lactose to provide a total amount of 580 to 590 mg to fill a size O hard gel capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:
1. A compound of the Formula (I)

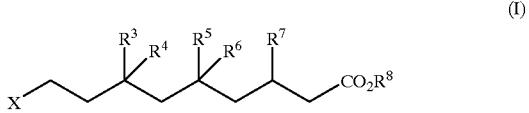

(I)

or a pharmaceutically acceptable salt thereof, wherein:
X is

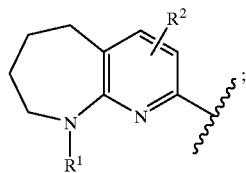

$R^1$ is hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of
    halogen, $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino, amino-$C_{1-6}$ alkyl, $C_{1-3}$ acylamino, $C_{1-3}$ acylamino-$C_{1-6}$ alkyl, ($C_{1-6}$ alkyl)$_{1-2}$ amino, $C_{3-6}$ cycloalkyl-$C_{0-2}$ alkylamino, ($C_{1-6}$ alkyl)$_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-$S(O)_{0-2}$, ($C_{1-8}$ alkyl)$_{0-2}$ aminocarbonyl, $C_{1-8}$ alkyloxycarbonylamino, ($C_{1-8}$ alkyl)$_{1-2}$ aminocarbonyloxy, (aryl $C_{1-3}$ alkyl)$_{1-2}$ amino, (aryl)$_{1-2}$ amino, aryl-$C_{1-3}$ alkylsulfonylamino, and $C_{1-8}$ alkylsulfonylamino;

or two $R^2$ substituents, when on the same non-aromatic carbon atom, are taken together with the carbon atom to which they are attached to form a carbonyl group;

$R^3$ and $R^5$ are each independently hydrogen, hydroxy, or $C_{1-6}$ alkoxy;

$R^4$ and $R^6$ are each independently hydrogen or $C_{1-3}$ alkyl; or $R^3$ and $R^4$ taken together or $R^5$ and $R^6$ taken together are carbonyl oxygen, with the proviso that both $R^3$ and $R^5$ are not simultaneously hydrogen;

$R^7$ is aryl wherein the aryl group is selected from the group consisting of
(1) phenyl,
(2) naphthyl,
(3) pyridyl,
(4) furyl,
(5) thienyl,
(6) pyrrolyl,
(7) oxazolyl,
(8) thiazolyl,
(9) imidazolyl,
(10) pyrazolyl,
(11) isoxazolyl,
(12) isothiazolyl,
(13) pyrimidinyl,
(14) pyrazinyl,
(15) pyridazinyl,
(16) tetrazolyl,
(17) quinolyl,
(18) isoquinolyl,
(19) benzirnidazolyl,
(20) benzofuryl,
(21) benzothienyl,
(22) indolyl,
(23) benzthiazolyl,
(24) benzoxazolyl,
(25) dihydrobenzofuryl,
(26) benzo(1,3)dioxolanyl,
(27) benzo(1,4)dioxanyl,
(28) quinazolyl,
(29) quinoxalyl, and
(30) 3,4-dihydro-2H-1,4-dioxa-5-aza-naphthalenyl;

wherein the aryl group as defined above in items (1) to (30) is unsubstituted or substituted with one to three substituents independently selected from the group consisting of hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfonyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and $R^8$ is hydrogen or $C_{1-3}$ alkyl.

2. The compound of claim 1 wherein X is $R^3$ is hydroxy and $R^5$ is hydrogen or $R^5$ is hydroxy and $R^3$ is hydrogen; and $R^4$ and $R^6$ are each independently hydrogen or methyl; or $R^3$ and $R^4$ taken together or $R^5$ and $R^6$ taken together are carbonyl oxygen.

3. The compound of claim 2 wherein $R^7$ is aryl wherein the aryl group is selected from the group consisting of
phenyl,
pyridyl,
quinolyl,
pyrimidinyl,
pyrazinyl,
pyridazinyl,
benzofuryl,
dihydrobenzofuryl, and
3,4-dihydro-2H-1,4-dioxa-5-aza-naphthalenyl;

wherein the aryl group is unsubstituted or substituted with one to two substituents independently selected from the group consisting of hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino-$C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino $C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl $C_{1-6}$ alkyl, $C_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl.

4. The compound of claim 3 wherein $R^7$ is
quinolyl,
pyridyl, or
pyrimidinyl;
unsubstituted or substituted with one to two substituents independently selected from halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, and trifluoroethoxy.

5. The compound of claim 4 wherein $R^2$ is selected from the group consisting of
halogen,
amino,
$C_{1-4}$ alkylamino,
$C_{3-6}$ cycloalkyl-$C_{0-2}$ alkylamino,
cyano,
$C_{1-4}$ alkyl,
cyclopropyl,
aryl $C_{1-3}$ alkyl, C$_{1-3}$ acylamino, C$_{1-4}$ alkoxy, C$_{1-4}$ alkylthio, aminocarbonyl, (C$_{1-6}$ alkyl)$_{1-2}$ aminocarbonyl, C$_{1-3}$ alkoxycarbonyl, trifluoromethyl, and trifluoromethoxy.

6. The compound of claim 5 wherein R$^2$ is selected from the group consisting of halogen, amino, C$_{1-3}$ alkylamino, C$_{3-6}$ cycloalkylmethylamino, C$_{1-4}$ alkyl, cyclopropyl, trifluoromethyl, and trifluoromethoxy.

7. The compound of claim 2 having the formula (II):

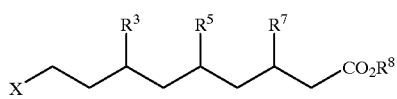

(II)

or a pharmaceutically acceptable salt thereof, wherein

X is

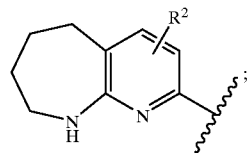

R$^3$ is hydroxy and R$^5$ is hydrogen or R$^5$ is hydroxy and R$^3$ is hydrogen;

R$^2$ is hydrogen, C$_{1-4}$ alkyl, cyclopropyl, amino, C$_{1-3}$ alkylamino, or cyclopropylmethylamino;

R$^7$ is quinolyl, pyridyl, or pyrimidinyl, unsubstituted or substituted with one substituent selected from C$_{1-4}$ alkyl, C$_{3-6}$ cycloalkyl, C$_{1-3}$ alkoxy, amino, C$_{1-3}$ alkylamino, di(C$_{1-3}$) alkylamino, cyano, trifluoromethyl, and trifluoromethoxy; and R$^8$ is hydrogen or C$_{1-3}$ alkyl.

8. The compound of claim 2 having the formula (III):

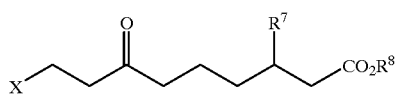

(III)

or a pharmaceutically salt thereof, wherein X is

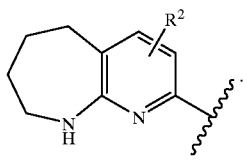

9. The compound of claim 8 wherein R$^7$ is aryl wherein the aryl group is selected from the group consisting of phenyl, pyridyl, quinolyl, pyrimidinyl, pyrazinyl, pyridazinyl, benzofuryl, dihydrobenzofuryl, and 3,4-dihydro-2H-1,4-dioxa-5-aza-naphthalenyl;

wherein the aryl group is unsubstituted or substituted with one to two substituents independently selected from hydroxy, hydroxy C$_{1-6}$ alkyl, halogen, C$_{1-8}$ alkyl, C$_{3-8}$ cycloalkyl, aryl, aryl C$_{1-3}$ alkyl, amino, amino C$_{1-6}$ alkyl, C$_{1-3}$ acylamino, C$_{1-3}$ acylamino C$_{1-6}$ alkyl, C$_{1-6}$ alkylamino, di(C$_{1-6}$)alkylamino, C$_{1-6}$ alkylamino C$_{1-6}$ alkyl, di(C$_{1-6}$) alkylamino C$_{1-6}$ alkyl, C$_{1-4}$ C$_{1-4}$ alkylthio, C$_{1-4}$ alkylsulfinyl, C$_{1-4}$ alkylsulfonyl, C$_{1-4}$ alkoxy C$_{1-6}$ alkyl, hydroxycarbonyl, hydroxycarbonyl C$_{1-6}$ alkyl, C$_{1-5}$ alkoxycarbonyl, C$_{1-3}$ alkoxycarbonyl C$_{1-6}$ alkyl, C$_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or C$_{1-3}$ alkyl.

10. The compound of claim 9 wherein R$^7$ is quinolyl, pyridyl, or pyrimidinyl;

unsubstituted or substituted with one to two substituents independently selected from halogen, phenyl, C$_{1-4}$ alkyl, C$_{3-6}$ cycloalkyl, C$_{1-3}$ alkoxy, amino, C$_{1-3}$ alkylamino, di(C$_{1-3}$) alkylarnino, hydroxy, cyano, trifluoromethyl, 1,1,1-trifluoroethyl, trifluoromethoxy, and trifluoroethoxy.

11. The compound of claim 10 wherein R$^2$ is selected from the group consisting of halogen, amino, C$_{1-4}$ alkylamino, C$_{3-6}$ cycloalkyl-C$_{0-2}$ alkylamino, cyano, C$_{1-4}$ alkyl, cyclopropyl, aryl C$_{1-3}$ alkyl, C$_{1-3}$ acylamino, C$_{1-4}$ alkoxy, C$_{1-4}$ alkylthio, aminocarbonyl, (C$_{1-6}$ alkyl)$_{1-2}$ aminocarbonyl, $C_{1-3}$ alkoxycarbonyl,
trifluoromethyl, and
trifluoromethoxy.

12. The compound of claim 11 wherein $R^2$ is selected from the group consisting of
halogen,
amino,
$C_{1-3}$ alkylamino,
$C_{3-6}$ cycloalkylmethylamino,
$C_{1-4}$ alkyl,
cyclopropyl,
trifluoromethyl, and
trifluoromethoxy.

13. The compound of claim 8 having the formula (III):

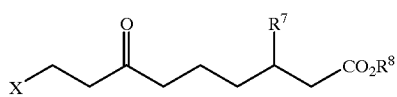

(III)

or a pharmaceutically salt thereof, wherein X is

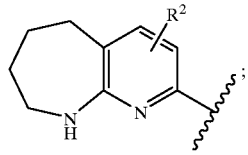

$R^2$ is $C_{1-4}$ alkyl or cyclopropyl;
$R^7$ is quinolyl, pyridyl, or pyrinudinyl, unsubstituted or substituted with one substituent selected from $C_{1-4}$ alkyl, $C_{3-6}$ cycloalkyl, $C_{1-3}$ alkoxy, amino, $C_{1-3}$ alkylamino, di($C_{1-3}$) alkylamino, cyano, tifluoromethyl, and tnfluoromethoxy; and
$R^8$ is hydrogen or $C_{1-3}$ alkyl.

14. The compound of claim 2 having the formula (IV):

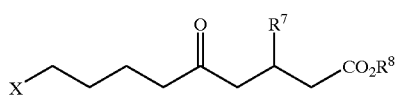

(IV)

or a pharmaceutically salt thereof, wherein X is

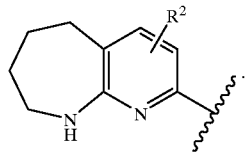

15. The compound of claim 14 wherein $R^7$ is aryl wherein the aryl group is selected from the group consisting of
phenyl,
pyridyl,
quinolyl,
pyriridinyl,
pyrazinyl,
pyridazinyl,
benzofuryl,
dihydrobenzofuryl, and
3,4-dihydro-2H-1,4-dioxa-5-aza-naphthalenyl;
wherein the aryl group is unsubstituted or substituted with one to two substituents independently selected from hydroxy, hydroxy $C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, di($C_{1\ 6}$)alkylamino, $C_{1-6}$ alkylamino $C_{1-6}$ alkyl, di($C_{1-6}$) alkylamino $C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, $C_{1-5}$ alkylcarbonyloxy, cyano, trifluoromethyl, 1,1,1-trifluoroethyl, trifluoromethoxy, trifluoroethoxy, and nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl.

16. The compound of claim 15 wherein $R^7$ is
quinolyl,
pyridyl, or
pyrimidinyl;
unsubstituted or substituted with one to two substituents independently selected from halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino hydroxy, cyano, trifluoromethyl, 1,1,1-trifluoroethyl, trifluoromethoxy, and trifluoroethoxy.

17. The compound of claim 16 wherein $R^2$ is selected from the group consisting of
halogen,
amino,
$C_{1-4}$ alkylamino,
$C_{3-6}$ cycloalkyl-$C_{0-2}$ alkylamino,
cyano,
$C_{1-4}$ alkyl,
cyclopropyl,
aryl $C_{1-3}$ alkyl,
$C_{1-3}$ acylamino,
$C_{1-4}$ alkoxy,
$C_{1-4}$ alkylthio,
aminocarbonyl,
($C_{1-6}$ alkyl)$_{1-2}$ aminocarbonyl,
$C_{1-3}$ alkoxycarbonyl,
trifluoromethyl, and
trifluoromethoxy.

18. The compound of claim 17 wherein $R^2$ is selected from the group consisting of
halogen,
amino,
$C_{1-3}$ alkylamino,
$C_{3-6}$ cycloalkylmethylamino,
$C_{1-4}$ alkyl,
cyclopropyl,
trifluoromethyl, and
trifluoromethoxy.

19. The compound of claim 14 having the formula (IV):

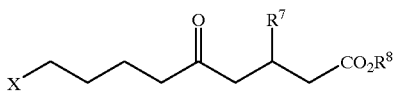

(IV)

or a pharmaceutically acceptable salt thereof, wherein X is

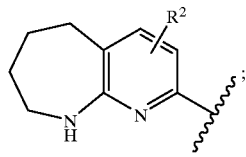

$R^2$ is $C_{1-4}$ alkyl or cyclopropyl;
$R^7$ is quinolyl, pyridyl, or pyrimidinyl, unsubstituted or substituted with one substituent selected from $C_{1-4}$ alkyl, $C_{3-6}$ cycloalkyl, $C_{1-3}$ alkoxy, amino, $C_{1-3}$ alkylamino, di($C_{1-3}$) alkylamino, cyano, trifluoromethyl, and trifluoromethoxy; and
$R^8$ is hydrogen or $C_{1-3}$ alkyl.

20. The compound of claim 19 selected from the group consisting of:

3-(2-Methyl-pyrimidin-5-yl)-5-oxo9-(6,7,8,9-tetrahydro-5H-pyrido[2,3-b]azepin-2-yl)-nonanoic acid;

3(R)-(2-Methyl-pyramidin-5-yl)-5-oxo-9-(6,7,8,9-tetrahydro-5H-pyrido[2,3-b]azepin-2-yl)-nonanoic acid;

3(S)-(2-Methyl-pyrimidin-5-yl)-5-oxo-9-(6,7,8,9-tetrahydro-5H-pyrdo[2,3-b]azepin-2-yl)-nonanoic acid;

3-(2-Methoxy-pyrimidin-5-yl)-5-oxo-9-(6,7,8,9-tetrahydro-5H -pyrido[2,3-b]azepin-2-yl)-nonanoic acid;

3(R)-(2-Methoxy-pyrimidin-5-yl)-5-oxo-9-(6,7,8,9-(tetrahydro-5H-pyrido[2,3-b]azepin-2-yl)-nonanoic acid;

3(S)-(2-Methoxy-pyrimidin-5-yl)-5-oxo-9-(6,7,8,9-tetrahydro-5H-pyrido[2,3-b]azepin-2-yl)-nonanoic acid;

3-(2-Ethoxy-pyrimidin-5-yl)-5-oxo-9-(6,7,8,9-tetrahydro-5H-pyrido[2,3-b]azepin-2-yl)-nonanoic acid;

3(R)-(2-Ethoxy-pyrimidin-5-yl)-5-oxo-9-(6,7,8,9-tetrahydro-5H-pyrido[2,3-b]azepin-2-yl)-nonanoic acid; and 3(S)-(2-Ethoxy-pyrimidin-5-yl)-5-oxo-9-(6,7,8,9-tetrahydro-5H-pyrido[2,3-b]azepin-2-yl)-nonanoic acid;

or a pharmaceutically acceptable salt thereof.

21. The compound of claim 20 selected from the group consisting of:

3(R)-(2-Methyl-pyrimidin-5-yl)-5-oxo-9-(6,7,8,9-tetrahydro-5H-pyrido[2,3-b]azepin-2-yl)-nonanoic acid;

3(S)-(2-Methyl-pyrimidin-5-yl)-5-oxo-9-(6,7,8,9-tetrahydro-5H-pyrido[2,3-b]azepin-2-yl)-nonanoic acid;

3(R)-(2-Methoxy-pyrimidin-5-yl)-5-oxo-9-(6,7,8,9-tetrahydro-5H-pyrido[2,3-b]azepin-2-yl)-nonanoic acid;

3(S)-(2-Methoxy-pyrimidin-5-yl)-5-oxo-9-(6,7,8,9-tetrahydro-5H-pyrido[2,3-b]azepin-2-yl)-nonanoic acid;

3(R)-(2-Ethoxy-pyrimidin-5-yl)-5-oxo-9-(6,7,8,9-tetrahydro-5H-pyrido[2,3-b]azepin-2-yl)-nonanoic acid; and 3(S)-(2-Ethoxy-pyrimidin-5-yl)-5-oxo-9-(6,7,8,9-tetrahydro-5H-pyrido [2,3-b]azepin-2-yl)-nonanoic acid;

or a pharmaceutically acceptable salt thereof.

22. The compound of claim 21 which is

3(S)-(2-Methyl-pyrimidin-5-yl)-5-oxo-9-(6,7,8,9-tetrahydro-5H-pyrido[2,3-b]azepin-2-yl)-nonanoic acid;

or a pharmaceutically acceptable salt thereof.

23. The compound of claim 21 which is

3(S)-(2-Methoxy-pyrimidin-5-yl)-5-oxo-9-(6,7,8,9-tetrahydro-5H-pyrido[2,3-b]azepin-2-nonanoic acid;

or a pharmaceutically acceptable salt thereof.

24. The compound of claim 21 which is

3(S)-(2-Ethoxy-pyrimidin-5-yl)-5-oxo-9-(6,7,8,9-tetrahydro-5H-pyrido[2,3-b]azepin-2-yl)-nonanoic acid;

or a pharmaceutically acceptable salt thereof.

25. A pharmaceutical composition comprising a compound according to claim 1 and a pharmaceutically acceptable carrier.

26. A method of inhibiting a condition selected from the group consisting of bone resorption, restenosis, angiogenesis, diabetic retinopathy, macular degeneration, and inflammatory arthritis, comprising administering to a mammal in need thereof a therapeutically effective amount of a compound according to claim 1.

27. A method of treating or preventing osteoporosis which comprises administering to a mammal in need of such treatment or prevention a therapeutically or prophylactically effective amount of a compound of claim 1.

28. A method of treating or preventing osteoporosis which comprises administering to a mammal in need of such treatment or prevention a therapeutically or prophylactically effective amount of a compound of claim 1 in combination with an effective amount of an organic bisphosphonate or a pharmaceutically acceptable salt or ester thereof.

* * * * *